(12) United States Patent
Audonnet et al.

(10) Patent No.: US 6,387,376 B1
(45) Date of Patent: *May 14, 2002

(54) RECOMBINANT VACCINE CONTAINING FELINE HERPES VIRUS TYPE 1 PARTICULARLY FOR TREATING FELINE INFECTIOUS PERITONITIS

(75) Inventors: Jean-Christophe Francis Audonnet; Philippe Guy Nicolas Baudu, both of Lyons; Michel Albert Emile Riviere, Ecully, all of (FR)

(73) Assignee: Merial, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/531,857

(22) Filed: Mar. 21, 2000

Related U.S. Application Data

(62) Division of application No. 09/080,044, filed on May 15, 1998, now Pat. No. 6,074,649, which is a continuation of application No. PCT/FR96/01830, filed on Nov. 19, 1996.

(30) Foreign Application Priority Data

Nov. 30, 1995 (FR) .............................. 95 14450

(51) Int. Cl.$^7$ ...................... A61K 39/12; A61K 39/245; C12N 15/00
(52) U.S. Cl. ................ 424/199.1; 424/229.1; 424/184.1; 424/205.1; 435/235.1; 435/320.1; 435/236; 435/351; 536/23.72; 536/24.1
(58) Field of Search .......................... 424/199.1, 229.1, 424/184.1, 205.1; 435/235.1, 320.1, 236; 536/23.72, 24.1

(56) References Cited

FOREIGN PATENT DOCUMENTS

WO    WO90/01547    *  2/1990

OTHER PUBLICATIONS

Nunberg et al. Vaccines 91, Cold Springs Harbor Laboratory Press, pp. 191–195, 1991.*
Lowery et al. Herpesvirus Workshop Secretariat, 1994, abstrcat only.*
Willemse et al. Vaccine. 1996, vol. 14, No. 16, pp. 1511–1516.*

* cited by examiner

Primary Examiner—Ali R. Salimi
(74) Attorney, Agent, or Firm—Frommer Lawrence & Haug, LLP; William S. Frommer; Thomas J. Kowalski

(57) ABSTRACT

The recombinant live vaccine comprises, as vector, a feline herpesvirus comprising and expressing at least one nucleotide sequence encoding a polypeptide, this sequence being inserted into the ORF5 and/or ORF2 sites. Polyvalent vaccine formula and feline herpesvirus DNA fragments.

45 Claims, 22 Drawing Sheets

PstI
1 CTGCAGAATTTCAACAAAAAACTGTCTAAGGAATGTACAAAGGGTGTGCTTCCCCTTTTGAAG
1▶ LeuGlnAsnPheAsnLysLysLeuSerLysGluCysThrLysGlyValLeuProLeuLeuLys
64 CTACTCGATCCCATGACAATAGCCATCAACAGCGACACAGACCGTCCCACTGGTGTATGTATA
22▶ LeuLeuAspProMetThrIleAlaIleAsnSerAspThrAspArgProThrGlyValCysIle
127 TACGTAGAACCCTGGCATGCCGATATCAGATCGATATTAAATATGCGGGGAATGCTCGCATCG
43▶ TyrValGluProTrpHisAlaAspIleArgSerIleLeuAsnMetArgGlyMetLeuAlaSer
190 GATGAAAACTCCAGATGTGATAATATATTTAGCTGTTTATGGACCCCGGACCTATTCTTCGAT
64▶ AspGluAsnSerArgCysAspAsnIlePheSerCysLeuTrpThrProLeuPhePheAsp
253 AGGTATCAACGGCACCTAGGCGGAGAGGTAAATGTCATTTGGACTCTATTTGATGATGCCGCA
85▶ ArgTyrGlnArgHisLeuGlyGlyGluValAsnValIleTrpThrLeuPheAspAspAlaAla
316 TCCCATCTTTCGAAGCTTTATGGAAAGGAATTTAATGAGGAATATGAACGTCTGGAGGCGGCT
106▶ SerHisLeuSerLysLeuTyrGlyLysGluPheAsnGluGluTyrGluArgLeuGluAlaAla
379 GGTATGGGTGTTGACAGCCTGCCTATTCAAGAGATGGCCTATCTTATTGTGAGAAGTGCAATA
127▶ GlyMetGlyValAspSerLeuProIleGlnGluMetAlaTyrLeuIleValArgSerAlaIle
442 ATGACCGGGAGTCCCTTCTTAATGTTCAAGGACGCGTGTAACGTGCACTATCACTTCGATACA
148▶ MetThrGlySerProPheLeuMetPheLysAspAlaCysAsnValHisTyrHisPheAspThr
505 CGTGGGGATGCGCTCACAACATCAAACCTATGTACTGAAATCATTCAGAAGGCTACAGACACT
169▶ ArgGlyAspAlaLeuThrThrSerAsnLeuCysThrGluIleIleGlnLysAlaThrAspThr
568 AAACATGGCGTTTGTAACTTGATAAGTATAAATCTACCGCAATGTTTACGCGCATCGGCTCAT
190▶ LysHisGlyValCysAsnLeuIleSerIleAsnLeuProGlnCysLeuArgAlaSerAlaHis
631 GATCAGAGCTTGTATTTCAGTATCCCATTACTCATTCGCGCAGCATATACCGCTACGATATTT
211▶ AspGlnSerLeuTyrPheSerIleProLeuLeuIleArgAlaAlaTyrThrAlaThrIlePhe
694 GTCAACGCAATGATGCGTGCTGGAAATTTCCCCACAGAAGCGGCCATGCGGGGTGTAGAAGAA
232▶ ValAsnAlaMetMetArgAlaGlyAsnPheProThrGluAlaAlaMetArgGlyValGluGlu
757 AATCGCTCTCTTGGATTGGGTATACAGGGGCTCCATACCACGTTTTTGGCCCTAGAGATGGAT
253▶ AsnArgSerLeuGlyLeuGlyIleGlnGlyLeuHisThrThrPheLeuAlaLeuGluMetAsp
820 ATGGTTTCTTATGAAGCCCGTCGCTTAAACCGCCAAATTTTAGAGAGTCTGCTCCTGGGAGCA
274▶ MetValSerTyrGluAlaArgArgLeuAsnArgGlnIleLeuGluSerLeuLeuLeuGlyAla
HindIII
883 ATCCACGCTAGCACATCCCTATGCAAGCTTGGTATGACACCATTTAAAAACTTCAGAGAGAGT
295▶ IleHisAlaSerThrSerLeuCysLysLeuGlyMetThrProPheLysAsnPheArgGluSer
946 ATCTATGGACGTGGTTTATTACCCTTTGATGCATACCCAAACACCCCCCTTATACATTTTAAA
316▶ IleTyrGlyArgGlyLeuLeuProPheAspAlaTyrProAsnThrProLeuIleHisPheLys
1009 AAATGGCAGCAATTGAGAGTAGTTATGATGAAATACGGACTTTACAATTCTCAATTTGTAGCA
337▶ LysTrpGlnGlnLeuArgValValMetMetLysTyrGlyLeuTyrAsnSerGlnPheValAla
1072 TTAATGCCAACGGTGTCCTCGTCCCAGGTCACTGAGAGTAGCGAGGGGTTCTCTCCAATTTTT
358▶ LeuMetProThrValSerSerSerGlnValThrGluSerSerGluGlyPheSerProIlePhe
1135 ACTAATCTGTTTAGTAAAGTCACTAGTACCGGGGAGATCTTACGACCAAACTTACAGTTGATG
379▶ ThrAsnLeuPheSerLysValThrSerThrGlyGluIleLeuArgProAsnLeuGlnLeuMet
1198 CGGACGATACGACGCCTATTTCCCAGGGAATGCGCGCGTCTCTCTGTTATATCAACCCTGGAA
400▶ ArgThrIleArgArgLeuPheProArgGluCysAlaArgLeuSerValIleSerThrLeuGlu
1261 GCTGCCCAATGGTCCATACGTGGTGCATTCGGGGATCTCGGGGATTATCACCCCCTAGCAAAA
421▶ AlaAlaGlnTrpSerIleArgGlyAlaPheGlyAspLeuGlyAspTyrHisProLeuAlaLys
1324 TTCAAAACCGCATTCGAATATGATCAACGACAGTTGATAGATATGTGTGCGGACAGGGCCCCC
442▶ PheLysThrAlaPheGluTyrAspGlnArgGlnLeuIleAspMetCysAlaAspArgAlaPro
1387 TTTGTAGATCAAAGCCAGTCCATGTCTCTGTTTATCTCTGAACCGGCTGATGGCAAATTACCC
463▶ PheValAspGlnSerGlnSerMetSerLeuPheIleSerGluProAlaAspGlyLysLeuPro
1450 GCCTCTAGGATTATGAACCTCCTTGTACATGCATATAAATGTGGACTGAAGACCGGTATGTAT
484▶ AlaSerArgIleMetAsnLeuLeuValHisAlaTyrLysCysGlyLeuLysThrGlyMetTyr
1513 TATTGTAAGCTCAAAAAGGCTACCAACAGTGGTGTCTTCTCCGGAGGCGAACTCATTTGTACT
505▶ TyrCysLysLeuLysLysAlaThrAsnSerGlyValPheSerGlyGlyGluLeuIleCysThr
1576 AGTTGCCACCTTTAAACGATTGTATATCATGTCTGCTAACGGATCTACCCCCAATACCGGTCTCCACTCCAA
526▶ SerCysHisLeu···

| FIG. 1A |
| FIG. 1B |
| FIG. 1C |
| FIG. 1D |
| FIG. 1E |
| FIG. 1F |
| FIG. 1G |

1648 TACCAAAATGCCGGTATCCATAGACTCTGATTGTAGCGCCTCGCGATACTTTTACACCCTGGAA
   1▶ MetProValSerIleAspSerAspCysSerAlaSerArgTyrPheTyrThrLeuGlu
1712 TGTCCAGATATAAACATGTTGCGGTCTCTCAGTATCGCGAATAGGTGGTTAGAAACCGATTTG
  20▶ CysProAspIleAsnMetLeuArgSerLeuSerIleAlaAsnArgTrpLeuGluThrAspLeu
1775 CCAATCGGTGATGATATAAAGGACATTACTACACTATCCGAATCGGAGTTGGACTTTTATCGT
  41▶ ProIleGlyAspAspIleLysAspIleThrThrLeuSerGluSerGluLeuAspPheTyrArg
                                                    SacII
1838 TTTCTATTTACATTTCTATCTGCCGCGGACGATCTGGTTAACCTGAATCTCGGCAATCTATCT
  62▶ PheLeuPheThrPheLeuSerAlaAlaAspAspLeuValAsnLeuAsnLeuGlyAsnLeuSer
1901 GAGCTCTTCACCCAAAAAGATATTTTACATTATTACATTGAACAGGAATGTATAGAGGTCGTC
  83▶ GluLeuPheThrGlnLysAspIleLeuHisTyrTyrIleGluGlnGluCysIleGluValVal
1964 CATTCGCGTGAATATAGCGCAATACAACTCCTCCTTTTTAAATGTGATGCGGAGGCGCGTACG
 104▶ HisSerArgGluTyrSerAlaIleGlnLeuLeuLeuPheLysCysAspAlaGluAlaArgThr
2027 GCCTATGTGGATTCTATGATTACAAAGCCGGAGCTTGCGAGGAAGGTTGAATGCGTCCGCACG
 125▶ AlaTyrValAspSerMetIleThrLysProGluLeuAlaArgLysValGluCysValArgThr
2090 CGAATTGGTGAATGTGAATCCATAGCCGAGAAGGATATTCTCATGATCTTAATAGAAGGTATC
 146▶ ArgIleGlyGluCysGluSerIleAlaGluLysAspIleLeuMetIleLeuIleGluGlyIle
2153 TTTTTTGTTGCATCCTTCGCTGCTATAGCTTATCTGAGAACCCACAACATATTCATCGTAACT
 167▶ PhePheValAlaSerPheAlaAlaIleAlaTyrLeuArgThrHisAsnIlePheIleValThr
2216 TGTCAAACCAACGATCTTATCAGCCGCGATGAGGCCATACATACAAACGCATCCTGCTGTATC
 188▶ CysGlnThrAsnAspLeuIleSerArgAspGluAlaIleHisThrAsnAlaSerCysCysIle
2279 TACAACAACTACCTCCCGGCTCAAATTAAACCATCCACGGAGAGGATTCACTCGTTATTTCGA
 209▶ TyrAsnAsnTyrLeuProAlaGlnIleLysProSerThrGluArgIleHisSerLeuPheArg
                                                    PstI
2342 GAGGCTGTGGAACTTGAGTGTGAGTTTATCTAACATGCGCTCCGCGCTGCAGTAATCTACTC
 230▶ GluAlaValGluLeuGluCysGluPheIleSerThrCysAlaProArgCysSerAsnLeuLeu
2405 AACGTGGCGGATATTTGTAATTATGTTCGGTATAGTGCGGACCGGTTGCTCGGTATTATCAAA
 251▶ AsnValAlaAspIleCysAsnTyrValArgTyrSerAlaAspArgLeuLeuGlyIleIleLys
2468 GTGGCTCCTATTTTCAACGTCCCGCCTCCTCATCCCGATTTTCCCTTAGCCTTTATGGTAATT
 272▶ ValAlaProIlePheAsnValProProProHisProAspPheProLeuAlaPheMetValIle
2531 GAAAAACATACCAATTTTTTCGAGAGACATAGCACTACATACAGTGGCACTGTTATCAATGAT
 293▶ GluLysHisThrAsnPhePheGluArgHisSerThrThrTyrSerGlyThrValIleAsnAsp
2594 CTATAAACAATGTCTTAATAATAAATTTAATTTAAGCTAACGTGTATCTGGATTCGTCCCTTTTTTCAAAAA
 314▶ Leu•••
2667 TAACTACACATGAGTCATTAGTAGCGTTCAACCGGTCTGTTTCCCGATACATCCACTGGTTCTTTAGTTATA
                                                    455◀•••AsnTyr
2739 ACGCCGTCGCGAATCACAATCATCCCAATAGGTAACCAGAACAACATAATAGTCGGGCGGGT
 452◀ArgArgArgSerAspCysAspAspTrpTyrThrValLeuValValTyrTyrAspProProThr
2802 TGAGATATGCTTCCAGAATAAGTTAGTTATATGTTTGGCATTGGCGGCATCCCCTATAAAATG
 431◀SerIleHisLysTrpPheLeuAsnThrIleHisLysAlaAsnAlaAlaAspGlyIlePheHis
2865 TTTTAGTGTTTCGAACACCAGGTTAAAATTAGCCTTCTCTTGGAGGATGGGAACGCGCTTTAA
 410◀LysLeuThrGluPheValLeuAsnPheAsnAlaLysGluGlnLeuIleProValArgLysLeu
2928 TATTGATAAGCGACCCCTTGTCTCCGGGGTCATTCTAGCGATAAGGTGTTTGATAAATTTCCG
 389◀IleSerLeuArgGlyArgThrGluProThrMetArgAlaIleLeuHisLysIlePheLysArg
2991 CTCGAGGACCATCATGTTTTGTCTGTGGCGGGGGTAAAAATGAGAGAGTCTGTGACGCGGTTT
 368◀GluLeuValMetMetAsnGlnArgHisArgProTyrPheHisSerLeuArgHisArgProLys
3054 CATTATCGGTGGGTATCGAGATGTGTATTTTAGAGTCAGACTCTGCTCTTCTATCATGGTCAG
 347◀MetIleProProTyrArgSerThrTyrLysLeuThrLeuSerGlnGluGluIleMetThrLeu
3117 CTGTTTAGACGATCCACGAATTTGAGATGGGCTGATCCTATATGTGTCTGTGGACATACATTC
 326◀GlnLysSerSerGlyArgIleGlnSerProSerIleArgTyrThrAspThrSerMetCysGlu
3180 AATATCCCGTTCTTCTGACGATGAAGCATCACTGCTGGTATCCCGGCATATACTAGTAGAGGA
 305◀IleAspArgGluGluSerSerSerAlaAspSerSerThrAspArgCysIleSerThrSerSer

| | FIG. 1A |
| | FIG. 1B |
| | FIG. 1C |
| FIG. 1B | FIG. 1 | FIG. 1D |
| | FIG. 1E |
| | FIG. 1F |
| | FIG. 1G |

```
3243 TTTTAGATTAATTACCTTTTCTTTTACCTTAGTTTTGCTCTGATGTCGTTGATTAGATCGTAG
 284◀LysLeuAsnIleValLysGluLysValLysThrLysSerGlnHisArgGlnAsnSerArgLeu
3306 ATTTTGTACGGATTTTAATATAGGTGTCTGGTGTAGATCTGTATGACAGCGAACAAATCGCGC
 263◀AsnGlnValSerLysLeuIleProThrGlnHisLeuAspThrHisCysArgValPheArgAla
                                                                EcoRI
3369 CACGAATTCCGAGTATGTCAGATTAAGCGACGCAAGGACGTCCCTACATCGTATTGTTGGTGG
 242◀ValPheGluSerTyrThrLeuAsnLeuSerAlaLeuValAspArgCysArgIleThrProPro
3432 GAAAAGTGGAATTATATCTAATATAATATCACACCCCATTAATATAAGATCGGTATCGGTTGT
 221◀PheLeuProIleIleAspLeuIleIleAspCysGlyMetLeuIleLeuAspThrAspThrThr
3495 ATAGATCTGCGCGACCGTATTTGTATGATATAGATTAGCACATACATCATCAGCCTCCATATC
 200◀TyrIleGlnAlaValThrAsnThrHisTyrLeuAsnAlaCysValAspAspAlaGluMetAsp
3558 ACTGACATTTACATATGGGTACCCTAGATAGCGGATGAGGTTTACACATAATCTATAACATAA
 179◀SerValAsnValTyrProTyrGlyLeuTyrArgIleLeuAsnValCysLeuArgTyrCysLeu
3621 ACGTGGGGTATAAGCTAATGAACTCCATCTCGCTGATATACGTTCTTGGATATCTACTTTGCA
 158◀ArgProThrTyrAlaLeuSerSerTrpArgAlaSerIleArgGluGlnIleAspValLysCys
3684 ATCTTTCGGGTTTCCACCATCTGGTTCCGAAGTATCTTCACACGGCCCTCCATGTGGAATGGA
 137◀AspLysProAsnGlyGlyAspProGluSerThrAspGluCysProGlyGlyHisProIleSer
3747 AAATTCCCCCAAGCGTCCAGATCCACCCTGTAAACACATCGTCTGTGTCACTATAGCCTTGGC
 116◀PheGluGlyLeuArgGlySerGlyGlyGlnLeuCysMetThrGlnThrValIleAlaLysAla
3810 TCCATATTTTACCTGTCCATCACCATAGATACCTCTATCCGAAACGAAGATCGGAAAGTATGA
  95◀GlyTyrLysValGlnGlyAspGlyTyrIleGlyArgAspSerValPheIleProPheTyrSer
3873 TCGCTTCTGTAACAGTTTAAGAAGCGAAAAGAAACACTCGGCAGTCACCGTTGCATTATCACT
  74◀ArgLysGlnLeuLeuLysLeuLeuSerPhePheCysGluAlaThrValThrAlaAsnAspSer
3936 TGTATATCTTTCTCTGGAAAGAATTTCTCCCATAAGTGTGTACATAACATTCCATAAATCTAT
  53◀ThrTyrArgGluArgSerLeuIleGluGlyMetLeuThrTyrMetValAsnTrpLeuAspIle
3999 AGCGATGGGTGTATAAATACCAGGTGGTGTAGTGATGGCATCATGTTTTACCAAACGGTTGCA
  32◀AlaIleProThrTyrIleGlyProProThrThrIleAlaAspHisLysValLeuArgAsnCys
4062 GTAGGCGTATTTTAACATCCCAAATAAGCCCATTCTGACACTATTGATTATATCTCGTTTCCTAGAGCA
  11◀TyrAlaTyrLysLeuMetGlyPheLeuGlyMet
4131 GAGTCGTATTAATTGGCGAGGTAAACAATCGCTCCGGTGAAGGCAGTTCCCCAACTAGATTAACCCCTAGTTGA
4205 TTATGGACATTATAATGCGCTGGGTGGCGGAATCATCGCCGCACCCAACTCAAAGCACGACCAAATATGAGCGG
4279 GTCTGTGGAACCTCAAAATCCTATTGGTGATCATGAACAATAAAAATGAAACCAAAATACATGGTAGATAATTA
4353 ATCCTCTCCCCCACTCTGGCGTCATAGCGCGGCGGTGAAGCCTATAAAGAATACAGGTGCGAGGAAATTGTCTT
4427 ACTTTTCCCTTTGTGAGTTTTAATTTGTGTGTAAAACTAGCTCTCTACGATGGCATTTCCACCGTCGAGA
                                                               1▶MetAlaPheProProSerArg
4497 TTAGAGGTTGGAATAAATAAAGCTATTAACCATCCGGCACAAGTTGTCCACGCGGGACCTCTT
   8▶LeuGluValGlyIleAsnLysAlaIleAsnHisProAlaGlnValValHisAlaGlyProLeu
4560 CCCGGTGGTGTCGAATCTAACACTATCTTCGGAAACGCTGTCCTCGAAGAAGACAAGCTACGC
  29▶ProGlyGlyValGluSerAsnThrIlePheGlyAsnAlaValLeuGluGluAspLysLeuArg
4623 GAGGTAATGACCATATTGACACCGATATCGACCAGTCTTAAAAACTCATTTTTGGTTTTTAGT
  50▶GluValMetThrIleLeuThrProIleSerThrSerLeuLysAsnSerPheLeuValPheSer
4686 GCCGATGGGATGTTGATTCATACGAGTGTATGTCACGAACAGATATATATACCAATATCAAAG
  71▶AlaAspGlyMetLeuIleHisThrSerValCysHisGluGlnIleTyrIleProIleSerLys
4749 AATCAGTTTTCATCATATAGATGGACATATGGACAGCCTGCGGTATTTTAGCGAAATGCAC
  92▶AsnGlnPheSerSerTyrArgTrpThrTyrGlyGlnProAlaValPheLeuAlaAsnMetHis
4812 GGACGTCGTAGCTTGTTGGACGTATTTAAAACTACTGGGAGAAAAAGTGCAACCAAGAAGGTA
 113▶GlyArgArgSerLeuLeuAspValPheLysThrThrGlyArgLysSerAlaThrLysLysVal
4875 ATTTTCGAGATAACTAATGTTCATCCGGGTAGAATGTTAAACCAAGTAGTTTTTAACTTAGAC
 134▶IlePheGluIleThrAsnValHisProGlyArgMetLeuAsnGlnValValPheAsnLeuAsp
4938 CTCGATGGTGGACTATCTTCTTCACAACTTATAAAATCAGAATTTAATAATTATTGTGTTATG
 155▶LeuAspGlyGlyLeuSerSerSerGlnLeuIleLysSerGluPheAsnAsnTyrCysValMet
5001 TTACCCACGAGAGTACCCGATTTGACGCTTGAGTTTTCAAAACCTCAACTAAACAAAATATTG
 176▶LeuProThrArgValProAspLeuThrLeuGluPheSerLysProGlnLeuAsnLysIleLeu
```

FIG. 1C

| | FIG. 1A |
|---|---|
| | FIG. 1B |
| | FIG. 1C |
| FIG. 1 | FIG. 1D |
| | FIG. 1E |
| | FIG. 1F |
| | FIG. 1G |

```
                                    SpeI
5064  GACCTTGGAAAACGCATAAAATCTACACTAGTGTTTGAATCTACGGTGAGAGAAACCATCAAT
197▶  AspLeuGlyLysArgIleLysSerThrLeuValPheGluSerThrValArgGluThrIleAsn
5127  ATTATATCCGACGTCGGGAGAGTAACATTTACCACGACTCATGAATCGGCTGATGGAAATCAA
218▶  IleIleSerAspValGlyArgValThrPheThrThrThrHisGluSerAlaAspGlyAsnGln
5190  GATAGCCGCTGTATTTTACGCAGTCTCCCAAGGTCCCACATACTTGGTAATGTATCATCAACC
239▶  AspSerArgCysIleLeuArgSerLeuProArgSerHisIleLeuGlyAsnValSerSerThr
5253  GTTAATTTCTCTGGGGTTTTGAAACCCTTCCGCCTAGCTTTGGAATCCCCCGTAAACTTTTTT
260▶  ValAsnPheSerGlyValLeuLysProPheArgLeuAlaLeuGluSerProValAsnPhePhe
5316  CAACTTCTTCGTAAATTGAAACTTACACATACCGACGTCAGCCTCAATTTCTTCTTCACTCCA
281▶  GlnLeuLeuArgLysLeuLysLeuThrHisThrAspValSerLeuAsnPhePhePheThrPro
5379  AGTACTACACCCATGTTAAGTCTGACTACCAGAAAACCCGTTGGTGTAATGATGTTTTTCTTC
302▶  SerThrThrProMetLeuSerLeuThrThrArgLysProValGlyValMetMetPhePhePhe
5442  TGTACCACGGAATGTCTAGGATCATCCGAGTCAATTAAAACCGGGGATATGGATGATCCCTCG
323▶  CysThrThrGluCysLeuGlySerSerGluSerIleLysThrGlyAspMetAspAspProSer
5505  ACAACCGAGGAGGAAAGTATCCCCAGGTTAAAGCGGCGAGTGTTAGAAGAGTTCCGTGATTCT
344▶  ThrThrGluGluGluSerIleProArgLeuLysArgArgValLeuGluGluPheArgAspSer
5568  GAAGGACCCAGTAAAAAACTTTGTACTTTTGTTTACTCATCTCCACTATGCAACCCGAATCCT
365▶  GluGlyProSerLysLysLeuCysThrPheValTyrSerSerProLeuCysAsnProAsnPro
5631  GGTACACGGGGAGAAAACCCATCTGATATTTAGATGTAAATAGCCAATACCACAGATCGTTCGCCTGTA
386▶  GlyThrArgGlyGluAsnProSerAspIle•••
5700  TACTTGATCCCCATTTATGTTAAAATAAAGTATTTTTAATGTAATATATGTGTAGTTTCGTTTATTCATAAACG
5774  CTAGTTAGATATCTCCACCCACATTTTTCTGGTATTTGTAATAAAAATTGAGCCAGGCGAAAGAAAGTCAGTAA
                                                                        SacI
5848  GTCGCCAGCCAGACTTCGGGTATGGCCACCGATGACTGTACGTCTCCAACTAATGCAGCTGGGAGC
                                     1▶MetAlaThrAspAspCysThrSerProThrAsnAlaAlaGlySer
5914  TCAACAACCAACAATAACGGTCTCGCTCCAGAAGGGATATCGGATATAACACTACCCTCATTT
16▶   SerThrThrAsnAsnAsnGlyLeuAlaProGluGlyIleSerAspIleThrLeuProSerPhe
5977  ACTGTGAGGAACTGCTCGGGATCGAGGACTGGATGTATCGCATGTGTGTACACGGCAACTAAA
37▶   ThrValArgAsnCysSerGlySerArgThrGlyCysIleAlaCysValTyrThrAlaThrLys
6040  GCGTTATGTTATATAGGGGTCCAATCTGGAATTTTAACAGCATCGATCGCTCTCATTTGGCTC
58▶   AlaLeuCysTyrIleGlyValGlnSerGlyIleLeuThrAlaSerIleAlaLeuIleTrpLeu
6103  CTAACACGTACAACAACATATGCAGCCGGAATCCTTATATTTATAAGTCTAATATCCACAATG
79▶   LeuThrArgThrThrThrTyrAlaAlaGlyIleLeuIlePheIleSerLeuIleSerThrMet
6166  AGGCTCTCTATGGTAAAAACTGAACGTATCACAACTATATGCCGCTTTACTCAGACCCTCTGT
100▶  ArgLeuSerMetValLysThrGluArgIleThrThrIleCysArgPheThrGlnThrLeuCys
6229  GTGGCCATAGCGGCAGTTGGATGGGCGTGTGATGATTTGTTACAACCAGTTGGATTTACCCCT
121▶  ValAlaIleAlaAlaValGlyTrpAlaCysAspAspLeuLeuGlnProValGlyPheThrPro
6292  CTTCTACTCCTATGTCTAGCAGGAATCGCTGTATGTGCTGCGATCATACATGTGTTTTACTTC
142▶  LeuLeuLeuLeuCysLeuAlaGlyIleAlaValCysAlaAlaIleIleHisValPheTyrPhe
6355  ATCTGCACAGCCAATGGATCGGGAACACATTTTCGTATGGCCATCGTTACCATGACCCTCGGT
163▶  IleCysThrAlaAsnGlySerGlyThrHisPheArgMetAlaIleValThrMetThrLeuGly
6418  GCGCTGTTGGGAGTATCGAGTATCGCCGTGACTGTGAAATCTGAAATTCTCATCGGCCTCGGT
184▶  AlaLeuLeuGlyValSerSerIleAlaValThrValLysSerGluIleLeuIleGlyLeuGly
6481  ATTGCATGCTCGATTATTGTCTCCCAGCGAGACTTTGGAATGATACTTAGAGACACATGTCAT
205▶  IleAlaCysSerIleIleValSerGlnArgAspPheGlyMetIleLeuArgAspThrCysHis
6544  TACAGATTAGGTCGTTATTCGTTAATGCGCACTTTTACGGATTTGGGGCGTGGTGCTAACCAT
226▶  TyrArgLeuGlyArgTyrSerLeuMetArgThrPheThrAspLeuGlyArgGlyAlaAsnHis
      SalI
6607  AATCCAGTCGACTTTATCGTACCCAACATCGAGGATGTCTACGAGGACAAGATTAGCAGCGTT
247▶  AsnProValAspPheIleValProAsnIleGluAspValTyrGluAspLysIleSerSerVal
6670  AAAATTTTTCGAGAACACCCCACTTTGATTATGGCCCCGTTGATAGGGCTAACCCTCACCCCT
268▶  LysIlePheArgGluHisProThrLeuIleMetAlaProLeuIleGlyLeuThrLeuThrPro
```

| | FIG. 1A |
|---|---|
| | FIG. 1B |
| | FIG. 1C |
| FIG. 1D FIG. 1 | FIG. 1D |
| | FIG. 1E |
| | FIG. 1F |
| | FIG. 1G |

```
6733 CCGATATGGGGTTATTGTCACATCACTAAATATGGCCATGATTTTCAGACGCCCTTAACAGTT
 289▶ProIleTrpGlyTyrCysHisIleThrLysTyrGlyHisAspPheGlnThrProLeuThrVal
6796 GTGATTTGTGTTATCGTTGGACATTGTTTGGCATTTTGCCTGGAACCTTTGATGGTCTACCGA
 310▶ValIleCysValIleValGlyHisCysLeuAlaPheCysLeuGluProLeuMetValTyrArg
6859 AGAATGTATATACCTGAGGTCCTCGTGAGTTTCCATGGCATGGCTGAAATAACCGGGATAGTC
 331▶ArgMetTyrIleProGluValLeuValSerPheHisGlyMetAlaGluIleThrGlyIleVal
6922 TTGGCACTGCTTGGTGTAAATTTTGGCACGCCGCTGGTTTTGACTCTGGCTATATCTGAGACT
 352▶LeuAlaLeuLeuGlyValAsnPheGlyThrProLeuValLeuThrLeuAlaIleSerGluThr
6985 CTAACTTGCCTACTCCATCTACGAAAAATCATCCTCGGCGCGAAACGCCTGGCTGCTACCTAC
 373▶LeuThrCysLeuLeuHisLeuArgLysIleIleLeuGlyAlaLysArgLeuAlaAlaThrTyr
7048 CTATGCAGGGGTCTACACACGGGCATGTATGTTACTGCTGGAATGTGTTATTTGTACAGTCAT
 394▶LeuCysArgGlyLeuHisThrGlyMetTyrValThrAlaGlyMetCysTyrLeuTyrSerHis
7111 ATGTAATGTACCACTCAACACGATATATTTATATCGCGGTTGTGTCTAATAACTGTTTTTAAATAAAGAGATA
 415▶Met•••
7184 AGTCGAAATCACAGGCAGTGAAATGCCTTAAAAATGGGTCTCCTGTCTATGTTAGGAATCTCTTATTTTAAGTA
                        SmaI
7258 GTCCCGCGAGACGATTTACATCCCGGGATCACCAACAATCTGCGATGAGACGATATAGGATGGGACGCGGAATC
                                                            SalI
7332 TACCTTCTCTATATCTGTCTGTTATATACATATCTCCAGTTTGGTACTTCGTCGACAACCGCGGTCAGTATTGA
7406 AAATAGTGATAATAGTACTGCGGAGATGTTATCATCTACCAGCATGTCCGCTACCACCCCGATATCCCAG
                                                       1▶MetSerAlaThrThrProIleSerGln
7476 CCAACATCTCCATTCACTACTCCAACTAGAAGATCTACAAATATAGCTACAAGTTCGAGTACC
 10▶ProThrSerProPheThrThrProThrArgArgSerThrAsnIleAlaThrSerSerSerThr
7539 ACCCAGGCATCCCAGCCAACATCTACATTAACTACTCTAACTAGAAGCTCGACAACTATAGCT
 31▶ThrGlnAlaSerGlnProThrSerThrLeuThrThrLeuThrArgSerSerThrThrIleAla
7602 ACAAGTCCGAGTACCACCCAGGCAGCCACATTCATAGGATCATCTACCGATTCCAATACCACT
 52▶ThrSerProSerThrThrGlnAlaAlaThrPheIleGlySerSerThrAspSerAsnThrThr
7665 TTACTCAAAACAACAAAAAAACCAAAGCGTAAAAAGAATAAGAATAACGGGGCCAGATTTAAA
 73▶LeuLeuLysThrThrLysLysProLysArgLysLysAsnLysAsnAsnGlyAlaArgPheLys
7728 TTAGATTGTGGATATAAGGGGGTTATCTACAGACCGTATTTTAGCCCTCTTCAGCTAAACTGT
 94▶LeuAspCysGlyTyrLysGlyValIleTyrArgProTyrPheSerProLeuGlnLeuAsnCys
7791 ACTCTACCCACAGAACCTCATATTACCAACCCTATTGACTTCGAGATCTGGTTTAAACCACGC
 115▶ThrLeuProThrGluProHisIleThrAsnProIleAspPheGluIleTrpPheLysProArg
7854 ACCAGATTTGGGGATTTTCTTGGGGATAAAGAAGACTTCGTAGGGAATCATACCCGCACCAGC
 136▶ThrArgPheGlyAspPheLeuGlyAspLysGluAspPheValGlyAsnHisThrArgThrSer
7917 ATATTACTATTTAGCAGCCGTAATGGGAGTGTTAATTCCATGGATCTTGGGGACGCGACACTC
 157▶IleLeuLeuPheSerSerArgAsnGlySerValAsnSerMetAspLeuGlyAspAlaThrLeu
7980 GGGATCCTACAATCTAGGATACCAGATTACACATTATATAATATTCCCATACAACATACCGAA
 178▶GlyIleLeuGlnSerArgIleProAspTyrThrLeuTyrAsnIleProIleGlnHisThrGlu
8043 GCGATGTCATTGGGAATCAAATCTGTGGAATCTGCCACGTCCGGTGTTTATACATGGCGGGTC
 199▶AlaMetSerLeuGlyIleLysSerValGluSerAlaThrSerGlyValTyrThrTrpArgVal
8106 TATGGTGGAGATGGACTAAATAAAACAGTGCTAGGACAGGTAAATGTATCTGTAGTGGCATAT
 220▶TyrGlyGlyAspGlyLeuAsnLysThrValLeuGlyGlnValAsnValSerValValAlaTyr
8169 CACCCCCCGAGCGTAAATCTTACACCACGCGCCAGTCTATTTAATAAGACCTTTGAGGCGGTA
 241▶HisProProSerValAsnLeuThrProArgAlaSerLeuPheAsnLysThrPheGluAlaVal
8232 TGTGCAGTGGCGAATTACTTCCCGCGATCCACGAAACTAACATGGTATCTTGACGGGAAGCCA
 262▶CysAlaValAlaAsnTyrPheProArgSerThrLysLeuThrTrpTyrLeuAspGlyLysPro
8295 ATAGAAAGGCAATACATTTCAGATACGGCAAGTGTATGGATAGATGGACTCATCACCAGAAGT
 283▶IleGluArgGlnTyrIleSerAspThrAlaSerValTrpIleAspGlyLeuIleThrArgSer
8358 TCTGTGTTGGCTATTCCGACAACTGAAACAGATTCCGAGAAACCAGATATACGATGTGATTTG
 304▶SerValLeuAlaIleProThrThrGluThrAspSerGluLysProAspIleArgCysAspLeu
8421 GAATGGCATGAAAGTCCTGTGTCCTATAAGAGATTCACGAAAAGTGTAGCCCCGGACGTCTAT
 325▶GluTrpHisGluSerProValSerTyrLysArgPheThrLysSerValAlaProAspValTyr
8484 TACCCACCTACTGTGTCTGTTACCTTCGCTGATACACGGGCTATATGTGATGTTAAATGTGTA
 346▶TyrProProThrValSerValThrPheAlaAspThrArgAlaIleCysAspValLysCysVal
```

```
8547 CCACGGGACGGGATATCCTTGATGTGGAAAATTGGTAACTACCATCTACCAAAAGCAATGAGT
367▶ProArgAspGlyIleSerLeuMetTrpLysIleGlyAsnTyrHisLeuProLysAlaMetSer
8610 GCTGATATACTGATCACAGGTCCGTGTATAGAACGTCCAGGTTTGGTCAACATTCAGAGTATG
388▶AlaAspIleLeuIleThrGlyProCysIleGluArgProGlyLeuValAsnIleGlnSerMet
8673 TGTGATATATCAGAAACGGATGGACCCGTGAGTTATACCTGTCAGACCATCGGATACCCACCA
409▶CysAspIleSerGluThrAspGlyProValSerTyrThrCysGlnThrIleGlyTyrProPro
8736 ATTCTACCGGGATTTTACGACACACAAGTCTACGACGCGTCCCCTGAAATCGTCAGTGAATCA
430▶IleLeuProGlyPheTyrAspThrGlnValTyrAspAlaSerProGluIleValSerGluSer
8799 ATGTTGGTTAGTGTCGTTGCTGTAATACTAGGAGCTGTTCTCATCACAGTCTTTATCTTTATT
451▶MetLeuValSerValValAlaValIleLeuGlyAlaValLeuIleThrValPheIlePheIle
8862 ACGGCATTATGTTTATATTATTCTCATCCCCGGCGATTATAACTCTTATAGTTCGTATAAATTACTT
472▶ThrAlaLeuCysLeuTyrTyrSerHisProArgArgLeu•••
8929 ATCATAACCGTGTTTCAGCGGTTATATTTTTATAACAGTTAATTGTTTACTAATAGTTTACAAAGTCCATCGTT
9003 TATAAAAAACAAGCCCAGTGGTATTATAATCATTCGTATGGATATAAACCGACTCCAATCCGTGATCTTTGGTA
                                                           SpeI
9077 ACCCGCGACGTAATTACTCTCACACATTTTAACTAGTCTACGATCACCCAGATATAATAAAAAGATTCGCGTGG
9151 ACATGCAAGGTATGAGGTCTACGTCACAGCCGTTGGTCGAGATACCACTGGTAGATATGGAACC
  1▶MetGlnGlyMetArgSerThrSerGlnProLeuValGluIleProLeuValAspMetGluPr
9215 ACAGCCATCTATACACTCCAACGAGCCTAACCCACCGAATAAAATGTTGACGACAGCTATTTC
 21▶oGlnProSerIleHisSerAsnGluProAsnProProAsnLysMetLeuThrThrAlaIleSe
9278 ATCGCGTAGGAGTGGAATTTTTTATTTTCTCTGGGTATGTTTTTTTTCGGAGTTATCCTAAC
 42▶rSerArgArgSerGlyIlePheLeuPheSerLeuGlyMetPhePhePheGlyValIleLeuTh
9341 AGCTACTATTATAGTATGTACATTCATATTTACAATACCAGTGGATATGCTCCAGATGCCACG
 63▶rAlaThrIleIleValCysThrPheIlePheThrIleProValAspMetLeuGlnMetProAr
9404 CTGCCCTGAGGAAACGGTGGGTATCAAAAACTGTTGTATCCGACCGATTAGACGCCATGTTAA
 84▶gCysProGluGluThrValGlyIleLysAsnCysCysIleArgProIleArgArgHisValLy
9467 ATCACACCAAGATCTAGTTGCCACATGTGCCGAATACATGGAACAACCCGCCACCGCATCTGC
105▶sSerHisGlnAspLeuValAlaThrCysAlaGluTyrMetGluGlnProAlaThrAlaSerAl
9530 TGTTGGAGCGCTTATACCATTATTGGACATCTTCAATGGAGATGGATATCTACAAACGACTC
126▶aValGlyAlaLeuIleProLeuLeuAspIlePheAsnGlyAspGlyIleSerThrAsnAspSe
9593 TCTTTACGATTGTATTCTCTCTGATGAAAAAAATCGTGTAATACATCAATGGCCGTATGTCA
147▶rLeuTyrAspCysIleLeuSerAspGluLysLysSerCysAsnThrSerMetAlaValCysGl
9656 ATCAACATATCTTCCAAATCCCCTAAGTGACTTTATTATGCGCGTTAGGCAGATATTTTCTGG
168▶nSerThrTyrLeuProAsnProLeuSerAspPheIleMetArgValArgGlnIlePheSerGl
9719 AATCCTAAATCATTAATCCATTTACTAAATAAATAAACAATACCGTTTAGGTAATTAAACATGATTCTAGT
189▶yIleLeuAsnHis•••
9790 GTTTATTGTCGTATGTACGGGCGATGGGTGGATAACAACTCGACAATGATCAATTATATTGATTAACCTTGTAA
9864 TAAATTCGTCGGATTATTGGATATATCGAGATGATATCACATTATTTTCTAATAGCGTGTGTTTGAAAG
                                        299◀•••LysArgIleAlaHisThrGlnPheA
      SpeI
9933 TCCACCCTACTAGTGCCATGTGCGCGTTTGATCGAAGAGGCATTTAATGTTGCCAGAGTTTCA
289◀spValArgSerThrGlyHisAlaArgLysIleSerSerAlaAsnLeuThrAlaLeuThrGluI
9996 ATTCCGTATGTATCGTCGAGTAATCTAGACCGTGGGCGAAATCTTTCTACTACTTCTTCAATC
268◀leGlyTyrThrAspAspLeuLeuArgSerArgProArgPheArgGluValValGluGluIleG
10059 CCAGGCGAGGATGATCGTCTGCGTGGGAGGTTTTTCTTTACATCACCACATTCGTTATATAAT
247◀lyProSerSerSerArgArgArgProLeuAsnLysLysValAspGlyCysGluAsnTyrLeuG
                                                    SmaI
10122 TCGGGATAATCACCTTTAGGTCCCCCGGGCTTGGAACATTGACACTTTTTATGACAAATCGGT
226◀luProTyrAspGlyLysProGlyGlyProLysSerCysGlnCysLysLysHisCysIleProT
10185 GTCTGGTAATGCTCCGTATATTGGAGCTGTGAGGTAGTTCCAGACGCGGACGATCCTCTGGAC
205◀hrGlnTyrHisGluThrTyrGlnLeuGlnSerThrThrGlySerAlaSerSerGlyArgSerG
                                                         XhoI
10248 TGCGCGGTATCTTCAGGGGAAATACAACGAGGGTGTTGGTAATGAGTCTGGTATGCATCTCGA
184◀lnAlaThrAspGluProSerIleCysArgProHisGlnTyrHisThrGlnTyrAlaAspArgP
```

```
10311 GGTTCATCTCCATTACTGAGATTCGAGGAATTAAAAGTTTCAGTGAGACCGTAGGACGGATTA
  163◄roGluAspGlyAsnSerLeuAsnSerSerAsnPheThrGluThrLeuGlyTyrSerProAsnA
10374 TTAATATGATCTTCCGACTCTTCGGGTCGGATGTCATCTAAACTGGTATAGGGTGTTCCGTCA
  142◄snIleHisAspGluSerGluGluProArgIleAspAspLeuSerThrTyrProThrGlyAspC
10437 CAGTCCGAGGAATCAAAACGATCATCGAGTTGTTTTGTGCGCGCATCCGATCTCAAGGGCGTT
  121◄ysAspSerSerAspPheArgAspAspLeuGlnLysThrArgAlaAspSerArgLeuProThrA
10500 CTATGGAAGCACCCCTCTACCCCGTCTGGGGTATTAGAAGGGTGGTCTCCAAGACCTGGGGAG
  100◄rgHisPheCysGlyGluValGlyAspProThrAsnSerProHisAspGlyLeuGlyProSerS
10563 GATATATCCCGAGGGGTTAGTGGGGAGGCTAAGAGTGATGCCATACCCATATATGGGTTTGGG
   79◄erIleAspArgProThrLeuProSerAlaLeuLeuSerAlaMetGlyMetTyrProAsnProP
10626 GGGGTGATGACAGCTGGTGGGTAGGTAACATCATGATGAGCGTGTGGAGTGGGTGGGGATGGT
   58◄roThrIleValAlaProProTyrThrValAspHisHisAlaHisProThrProProSerProL
10689 AGTGGGAGGCTCTGCCGATCTATGTGTGTCATCATCTGTGATACACACCGCCTCTCAGTTTTC
   37◄euProLeuSerGlnArgAspIleHisThrMetMetGlnSerValCysArgArgGluThrLysA
                                                              EcoRI
10752 GCCCTCTCCCGGGTGGATCTCCGTCTTCCACGTTCTATCGAACCAAGAATTC
   16◄laArgGluArgThrSerArgArgArgGlyArgGluIleSerGlyLeuIle
```

| | FIG. 1A |
|---|---|
| | FIG. 1B |
| | FIG. 1C |
| FIG. 1G | FIG. 1 | FIG. 1D |
| | FIG. 1E |
| | FIG. 1F |
| | FIG. 1G |

SEQUENCE LISTING

<160> NUMBER OF SEQ ID NOS: 33

<210> SEQ ID NO 1
<211> LENGTH: 10803
<212> TYPE: DNA
<213> ORGANISM: Feline herpesvirus 1

<400> SEQUENCE: 1

```
ctgcagaatt tcaacaaaaa actgtctaag gaatgtacaa agggtgtgct tcccctttg      60
aagctactcg atcccatgac aatagccatc aacagcgaca cagaccgtcc cactggtgta    120
tgtatatacg tagaaccctg gcatgccgat atcagatcga tattaaatat gcggggaatg    180
ctcgcatcgg atgaaaactc cagatgtgat aatatattta gctgtttatg gaccccggac    240
ctattcttcg ataggtatca acggcaccta ggcggagagg taaatgtcat ttggactcta    300
tttgatgatg ccgcatccca tctttcgaag ctttatggaa aggaatttaa tgaggaatat    360
gaacgtctgg aggcggctgg tatgggtgtt gacagcctgc ctattcaaga gatggcctat    420
cttattgtga gaagtgcaat aatgaccggg agtcccttct taatgttcaa ggacgcgtgt    480
aacgtgcact atcacttcga tacacgtggg gatgcgctca aacatcaaa  cctatgtact    540
gaaatcattc agaaggctac agacactaaa catggcgttt gtaacttgat aagtataaat    600
ctaccgcaat gtttacgcgc atcggctcat gatcagagct tgtatttcag tatcccatta    660
ctcattcgcg cagcatatac cgctacgata tttgtcaacg caatgatgcg tgctggaaat    720
ttccccacag aagcggccat gcggggtgta aagaaaatc gctctcttgg attgggtata    780
cagggggctcc ataccacgtt tttggcccta gagatggata tggtttctta tgaagcccgt    840
cgcttaaacc gccaaatttt agagagtctg ctcctgggag caatccacgc tagcacatcc    900
ctatgcaagc ttggtatgac accatttaaa aacttcagag agagtatcta tggacgtggt    960
ttattaccct ttgatgcata cccaaacacc cccttatac attttaaaaa atggcagcaa   1020
ttgagagtag ttatgatgaa atacggactt tacaattctc aatttgtagc attaatgcca   1080
acggtgtcct cgtcccaggt cactgagagt agcgaggggt tctctccaat ttttactaat   1140
ctgtttagta aagtcactag taccggggag atcttacgac caaacttaca gttgatgcgg   1200
acgatacgac gcctatttcc cagggaatgc gcgcgtctct ctgttatatc aaccctggaa   1260
gctgcccaat ggtccatacg tggtgcattc ggggatctcg gggattatca ccccctagca   1320
aaattcaaaa ccgcattcga atatgatcaa cgacagttga tagatatgtg tgcggacagg   1380
gcccccttg  tagatcaaag ccagtccatg tctctgttta tctctgaacc ggctgatggc   1440
aaattacccg cctctaggat tatgaacctc cttgtacatg catataatg  tggactgaag   1500
accggtatgt attattgtaa gctcaaaaag gctaccaaca gtggtgtctt ctccggaggc   1560
gaactcattt gtactagttg ccacctttaa acgattgtat atcatgtctg ctaacggatc   1620
taccccaat  accggtctcc actccaatac caaatgccg  gtatccatag actctgattg   1680
tagcgcctcg cgatactttt acaccctgga atgtccagat ataaacatgt tgcggtctct   1740
cagtatcgcg aataggtggt tagaaaccga tttgccaatc ggtgatgata taaggacat   1800
tactacacta tccgaatcgg agttggactt ttatcgtttt ctatttacat ttctatctgc   1860
```

-continued

```
cgcggacgat ctggttaacc tgaatctcgg caatctatct gagctcttca cccaaaaaga   1920
tattttacat tattacattg aacaggaatg tatagaggtc gtccattcgc gtgaatatag   1980
cgcaatacaa ctcctccttt ttaaatgtga tgcggaggcg cgtacggcct atgtggattc   2040
tatgattaca aagccggagc ttgcgaggaa ggttgaatgc gtccgcacgc gaattggtga   2100
atgtgaatcc atagccgaga aggatattct catgatctta atagaaggta tcttttttgt   2160
tgcatccttc gctgctatag cttatctgag aacccacaac atattcatcg taacttgtca   2220
aaccaacgat cttatcagcc gcgatgaggc catacataca aacgcatcct gctgtatcta   2280
caacaactac ctcccggctc aaattaaacc atccacggag aggattcact cgttatttcg   2340
agaggctgtg gaacttgagt gtgagtttat ctcaacatgc gctccgcgct gcagtaatct   2400
actcaacgtg gcggatattt gtaattatgt tcggtatagt gcggaccggt tgctcggtat   2460
tatcaaagtg gctcctattt tcaacgtccc gcctcctcat cccgattttc ccttagcctt   2520
tatggtaatt gaaaacata ccatttttt cgagagacat agcactacat acagtggcac   2580
tgttatcaat gatctataaa caatgtctta ataataaatt taatttaagc taacgtgtat   2640
ctggattcgt cccttttttt caaaaataac tacacatgag tcattagtag cgttcaaccg   2700 gtctgttttcc cgatacatcc actggttctt tagttataac gccgtcgcga atcacaatca   2760
tcccaatagg taaccagaac aacataatag tcgggcgggg ttgagatatg cttccagaat   2820
aagttagtta tatgttttggc attggcggca tcccctataa aatgttttag tgtttcgaac   2880
accaggttaa aattagcctt ctcttggagg atgggaacgc gctttaatat tgataagcga   2940 cccccttgtct ccggggtcat tctagcgata aggtgtttga taaatttccg ctcgaggacc   3000
atcatgtttt gtctgtggcg ggggtaaaaa tgagagagtc tgtgacgcgg tttcattatc   3060
ggtgggtatc gagatgtgta ttttagagtc agactctgct cttctatcat ggtcagctgt   3120
ttagacgatc cacgaatttg agatgggctg atcctatatg tgtctgtgga catacattca   3180
atatcccgtt cttctgacga tgaagcatca ctgctggtat cccggcatat actagtagag   3240
gattttagat taattacctt ttcttttacc ttagttttgc tctgatgtcg ttgattagat   3300
cgtagatttt gtacggattt taatataggt gtctggtgta gatctgtatg acagcgaaca   3360
aatcgcgcca cgaattccga gtatgtcaga ttaagcgacg caaggacgtc cctacatcgt   3420
attgttggtg ggaaaagtgg aattatatct aatataatat cacaccccat taatataaga   3480
tcggtatcgg ttgtatagat ctgcgcgacc gtatttgtat gatatagatt agcacataca   3540
tcatcagcct ccatatcact gacatttaca tatgggtacc ctagatagcg gatgaggttt   3600
acacataatc tataacataa acgtggggta taagctaatg aactccatct cgctgatata   3660
cgttcttgga tatctacttt gcaatctttc gggtttccac catctggttc cgaagtatct   3720
tcacacggcc ctccatgtgg aatggaaaat tccccaagc gtccagatcc accctgtaaa   3780
cacatcgtct gtgtcactat agccttggct ccatatttta cctgtccatc accatagata   3840
cctctatccg aaacgaagat cggaaagtat gatcgcttct gtaacagttt aagaagcgaa   3900
aagaaacact cggcagtcac cgttgcatta tcacttgtat atctttctct ggaaagaatt   3960
tctcccataa gtgtgtacat aacattccat aaatctatag cgatgggtgt ataaatacca   4020
ggtggtgtag tgatggcatc atgtttttacc aaacggttgc agtaggcgta ttttaacatc   4080
ccaaataagc ccattctgac actattgatt atatctcgtt tcctagagca gagtcgtatt   4140
aattggcgag gtaaacaatc gctccggtga aggcagttcc ccaactagat taacccctag   4200
```

```
ttgattatgg acattataat gcgctgggtg gcggaatcat cgccgcaccc aactcaaagc    4260
acgaccaaat atgagcgggt ctgtggaacc tcaaaatcct attggtgatc atgaacaata    4320
aaaatgaaac caaatacat ggtagataat taatcctctc ccccactctg gcgtcatagc    4380
gcggcggtga agcctataaa gaatacaggt gcgaggaaat tgtcttactt ttccctttgt    4440
gagttttaat ttgtgtgtaa aactagctct ctacgatggc atttccaccg tcagattag    4500 aggttggaat aaataaagct attaaccatc cggcacaagt tgtccacgcg ggacctcttc    4560
ccggtggtgt cgaatctaac actatcttcg gaaacgctgt cctcgaagaa gacaagctac    4620
gcgaggtaat gaccatattg acaccgatat cgaccagtct taaaaactca ttttggtttt    4680
ttagtgccga tgggatgttg attcatacga gtgtatgtca cgaacagata tataccaa    4740 tatcaaagaa tcagttttca tcatatagat ggacatatgg acagcctgcg gtatttttag    4800
cgaatatgca cggacgtcgt agcttgttgg acgtatttaa aactactggg agaaaaagtg    4860
caaccaagaa ggtaattttc gagataacta atgttcatcc gggtagaatg ttaaaccaag    4920
tagtttttaa cttagacctc gatggtggac tatcttcttc acaacttata aaatcagaat    4980
ttaataatta ttgtgttatg ttacccacga gagtacccga tttgacgctt gagttttcaa    5040
aacctcaact aaacaaaata ttggaccttg gaaaacgcat aaaatctaca ctagtgtttg    5100
aatctacggt gagagaaacc atcaatatta tatccgacgt cgggagagta acatttacca    5160
cgactcatga atcggctgat ggaaatcaag atagccgctg tattttacgc agtctcccaa    5220
ggtcccacat acttggtaat gtatcatcaa ccgttaattt ctctggggtt ttgaaaccct    5280
tccgcctagc tttggaatcc cccgtaaact tttttcaact tcttcgtaaa ttgaaactta    5340
cacataccga cgtcagcctc aatttcttct tcactccaag tactcacccc atgttaagtc    5400
tgactaccag aaaacccgtt ggtgtaatga tgtttttctt ctgtaccacg aatgtctag    5460 gatcatccga gtcaattaaa accggggata tggatgatcc ctcgacaacc gaggaggaaa    5520
gtatccccag gttaaagcgg cgagtgttag aagagttccg tgattctgaa ggacccagta    5580
aaaaactttg tacttttgtt tactcatctc cactatgcaa cccgaatcct ggtacacggg    5640
gagaaaaccc atctgatatt tagatgtaaa tagccaatac cacagatcgt tcgcctgtat    5700
acttgatccc catttatgtt aaaataaagt attttttaatg taatatatgt gtagtttcgt    5760
ttattcataa acgctagtta gatatctcca cccacatttt tctggtattt gtaataaaaa    5820
ttgagccagc cgaaagaaag tcagtaagtc gccagccaga cttcgggtat ggccaccgat    5880
gactgtacgt ctccaactaa tgcagctggg agctcaacaa ccaacaataa cggtctcgct    5940
ccagaaggga tatcggatat aacactaccc tcatttactg tgaggaactg ctcgggatcg    6000
aggactggat gtatcgcatg tgtgtacacg gcaactaaag cgttatgtta tatagggtc    6060 caatctggaa ttttaacagc atcgatcgct ctcatttggc tcctaacacg tacaacaaca    6120
tatgcagccg gaatccttat atttataagt ctaatatcca caatgaggct ctctatggta    6180
aaaactgaac gtatcacaac tatatgccgc tttactcaga ccctctgtgt ggccatagcg    6240
gcagttggat gggcgtgtga tgatttgtta caaccagttg gatttacccc tcttctactc    6300
ctatgtctag caggaatcgc tgtatgtgct gcgatcatac atgtgtttta cttcatctgc    6360
acagccaatg gatcgggaac acattttcgt atggccatcg ttaccatgac cctcggtgcg    6420
ctgttgggag tatcgagtat cgccgtgact gtgaaatctg aaattctcat cggcctcggt    6480
attgcatgct cgattattgt ctcccagcga actttggaa tgatacttag agacacatgt    6540
cattacagat taggtcgtta ttcgttaatg cgcacttttta cggatttggg gcgtggtgct    6600
```

```
aaccataatc cagtcgactt tatcgtaccc aacatcgagg atgtctacga ggacaagatt    6660
agcagcgtta aaattttcg agaacacccc actttgatta tggccccgtt gatagggcta     6720
accctcaccc ctccgatatg gggttattgt cacatcacta aatatggcca tgattttcag    6780
acgcccttaa cagttgtgat ttgtgttatc gttggacatt gtttggcatt ttgcctggaa    6840
cctttgatgg tctaccgaag aatgtatata cctgaggtcc tcgtgagttt ccatggcatg    6900
gctgaaataa ccgggatagt cttggcactg cttggtgtaa attttggcac gccgctggtt    6960
ttgactctgg ctatatctga gactctaact tgcctactcc atctacgaaa atcatcctc     7020 ggcgcgaaac gcctggctgc tacctaccta tgcagggtc tacacacggg catgtatgtt     7080
actgctggaa tgtgttattt gtacagtcat atgtaatgta ccactcaaca cgatatattt    7140
atatcgcggt tgtgtctaat aactgttttt aaataaagag ataagtcgaa atcacaggca    7200
gtgaaatgcc ttaaaaatgg gtctcctgtc tatgttagga atctcttatt ttaagtagtc    7260
ccgcgagacg atttacatcc cgggatcacc aacaatctgc gatgagacga tataggatgg    7320
gacgcggaat ctaccttctc tatatctgtc tgttatatac atatctccag tttggtactt    7380
cgtcgacaac cgcggtcagt attgaaaata gtgataatag tactgcggag atgttatcat    7440
ctaccagcat gtccgctacc accccgatat cccagccaac atctccattc actactccaa    7500
ctagaagatc tacaaatata gctacaagtt cgagtaccac ccaggcatcc cagccaacat    7560
ctacattaac tactctaact agaagctcga caactatagc tacaagtccg agtaccaccc    7620
aggcagccac attcatagga tcatctaccg attccaatac cactttactc aaaacaacaa    7680
aaaaaccaaa gcgtaaaaag aataagaata acggggccag atttaaatta gattgtggat    7740 ataaggggt tatctacaga ccgtattta gccctcttca gctaaactgt actctaccca      7800
cagaacctca tattaccaac cctattgact tcgagatctg gtttaaacca cgcaccagat    7860
ttggggattt tcttggggat aaagaagact tcgtagggaa tcatacccgc accagcatat    7920
tactatttag cagccgtaat gggagtgtta attccatgga tcttggggac gcgacactcg    7980
ggatcctaca atctaggata ccagattaca cattatataa tattcccata caacataccg    8040
aagcgatgtc attgggaatc aaatctgtgg aatctgccac gtccggtgtt tatacatggc    8100
gggtctatgg tggagatgga ctaaataaaa cagtgctagg acaggtaaat gtatctgtag    8160
tggcatatca ccccccgagc gtaaatctta caccacgcgc cagtctattt aataagacct    8220
ttgaggcggt atgtgcagtg gcgaattact tcccgcgatc cacgaaacta acatggtatc    8280
ttgacgggaa gccaatagaa aggcaataca tttcagatac ggcaagtgta tggatagatg    8340
gactcatcac cagaagttct gtgttggcta ttccgacaac tgaaacagat tccgagaaac    8400
cagatatacg atgtgatttg gaatggcatg aaagtcctgt gtcctataag agattcacga    8460
aaagtgtagc cccggacgtc tattacccac ctactgtgtc tgttaccttc gctgatacac    8520
gggctatatg tgatgttaaa tgtgtaccac gggacgggat atccttgatg tggaaaattg    8580
gtaactacca tctaccaaaa gcaatgagtg ctgatatact gatcacaggt ccgtgtatag    8640
aacgtccagg tttggtcaac attcagagta tgtgtgatat atcagaaacg gatggacccg    8700
tgagttatac ctgtcagacc atcggatacc caccaattct accgggattt tacgacacac    8760
aagtctacga cgcgtcccct gaaatcgtca gtgaatcaat gttggttagt gtcgttgctg    8820
taatactagg agctgttctc atcacagtct ttatctttat tacggcatta tgtttatatt    8880
attctcatcc ccggcgatta taactcttat agttcgtata aattacttat cataaccgtg    8940
```

-continued

```
tttcagcggt tatatttta taacagttaa ttgtttacta atagtttaca aagtccatcg    9000
tttataaaaa acaagcccag tggtattata atcattcgta tggatataaa ccgactccaa   9060
tccgtgatct ttggtaaccc gcgacgtaat tactctcaca catttaact agtctacgat    9120
cacccagata taataaaaag attcgcgtgg acatgcaagg tatgaggtct acgtcacagc   9180
cgttggtcga gataccactg gtagatatgg aaccacagcc atctatacac tccaacgagc   9240
ctaacccacc gaataaaatg ttgacgacag ctatttcatc gcgtaggagt ggaattttt    9300
tattttctct gggtatgttt ttttcggag ttatcctaac agctactatt atagtatgta    9360
cattcatatt tacaatacca gtggatatgc tccagatgcc acgctgccct gaggaaacgg   9420
tgggtatcaa aaactgttgt atccgaccga ttagacgcca tgttaaatca caccaagatc   9480
tagttgccac atgtgccgaa tacatggaac aacccgccac cgcatctgct gttggagcgc   9540
ttataccatt attggacatc ttcaatggag atgggatatc tacaaacgac tctctttacg   9600
attgtattct ctctgatgaa aaaaaatcgt gtaatacatc aatggccgta tgtcaatcaa    9660
catatcttcc aaatcccta agtgacttta ttatgcgcgt taggcagata ttttctggaa    9720
tcctaaatca ttaatccatt tactaaataa ataaacaata ccgtttaggt aattaaacat    9780
gattctagtg tttattgtcg tatgtacggg cgatgggtgg ataacaactc gacaatgatc   9840
aattatattg attaaccttg taataaattc gtcggattat tggatatatc gagatgatat   9900
cacattattt tctaatagcg tgtgtttgaa agtccaccct actagtgcca tgtgcgcgtt   9960
tgatcgaaga ggcatttaat gttgccgaga tttcaattcc gtatgtatcg tcgagtaatc   10020
tagaccgtgg gcgaaatctt tctactactt cttcaatccc aggcgaggat gatcgtctgc   10080
gtgggaggtt tttcttaca tcaccacatt cgttatataa ttcgggataa tcacctttag    10140
gtcccccggg cttggaacat tgacactttt tatgacaaat cggtgtctgg taatgctccg   10200
tatattggag ctgtgaggta gttccagacg cggacgatcc tctggactgc gcggtatctt   10260
cagggggaaat acaacgaggg tgttggtaat gagtctggta tgcatctcga ggttcatctc   10320
cattactgag attcgaggaa ttaaaagttt cagtgagacc gtaggacgga ttattaatat   10380
gatcttccga ctcttcgggt cggatgtcat ctaaactggt ataggtgtt ccgtcacagt     10440
ccgaggaatc aaaacgatca tcgagttgtt ttgtgcgcgc atccgatctc aagggcgttc   10500
tatggaagca cccctctacc ccgtctgggg tattagaagg gtggtctcca agacctgggg   10560
aggatatatc ccgagggggtt agtggggagg ctaagagtga tgccataccc atatatgggg   10620
ttgggggggt gatgacagct ggtgggtagg taacatcatg atgagcgtgt ggagtgggtg   10680
gggatggtag tgggaggctc tgccgatcta tgtgtgtcat catctgtgat acacaccgcc   10740
tctcagtttt cgccctctcc cgggtggatc tccgtcttcc acgttctatc gaaccaagaa   10800
ttc                                                                 10803
```

<210> SEQ ID NO 2
<211> LENGTH: 529
<212> TYPE: PRT
<213> ORGANISM: Feline herpesvirus 1

<400> SEQUENCE: 2

Leu Gln Asn Phe Asn Lys Lys Leu Ser Lys Glu Cys Thr Lys Gly Val
1               5                   10                  15

Leu Pro Leu Leu Lys Leu Leu Asp Pro Met Thr Ile Ala Ile Asn Ser
            20                  25                  30

Asp Thr Asp Arg Pro Thr Gly Val Cys Ile Tyr Val Glu Pro Trp His

-continued

```
                35                  40                  45
Ala Asp Ile Arg Ser Ile Leu Asn Met Arg Gly Met Leu Ala Ser Asp
         50                  55                  60
Glu Asn Ser Arg Cys Asp Asn Ile Phe Ser Cys Leu Trp Thr Pro Asp
 65                  70                  75                  80
Leu Phe Phe Asp Arg Tyr Gln Arg His Leu Gly Gly Glu Val Asn Val
                 85                  90                  95
Ile Trp Thr Leu Phe Asp Asp Ala Ala Ser His Leu Ser Lys Leu Tyr
                100                 105                 110
Gly Lys Glu Phe Asn Glu Glu Tyr Glu Arg Leu Glu Ala Ala Gly Met
                115                 120                 125
Gly Val Asp Ser Leu Pro Ile Gln Glu Met Ala Tyr Leu Ile Val Arg
        130                 135                 140
Ser Ala Ile Met Thr Gly Ser Pro Phe Leu Met Phe Lys Asp Ala Cys
145                 150                 155                 160
Asn Val His Tyr His Phe Asp Thr Arg Gly Asp Ala Leu Thr Thr Ser
                165                 170                 175
Asn Leu Cys Thr Glu Ile Ile Gln Lys Ala Thr Asp Thr Lys His Gly
                180                 185                 190
Val Cys Asn Leu Ile Ser Ile Asn Leu Pro Gln Cys Leu Arg Ala Ser
            195                 200                 205
Ala His Asp Gln Ser Leu Tyr Phe Ser Ile Pro Leu Leu Ile Arg Ala
        210                 215                 220
Ala Tyr Thr Ala Thr Ile Phe Val Asn Ala Met Met Arg Ala Gly Asn
225                 230                 235                 240
Phe Pro Thr Glu Ala Ala Met Arg Gly Val Glu Glu Asn Arg Ser Leu
                245                 250                 255
Gly Leu Gly Ile Gln Gly Leu His Thr Thr Phe Leu Ala Leu Glu Met
            260                 265                 270
Asp Met Val Ser Tyr Glu Ala Arg Arg Leu Asn Arg Gln Ile Leu Glu
        275                 280                 285
Ser Leu Leu Gly Ala Ile His Ala Ser Thr Ser Leu Cys Lys Leu
        290                 295                 300
Gly Met Thr Pro Phe Lys Asn Phe Arg Glu Ser Ile Tyr Gly Arg Gly
305                 310                 315                 320
Leu Leu Pro Phe Asp Ala Tyr Pro Asn Thr Pro Leu Ile His Phe Lys
                325                 330                 335
Lys Trp Gln Gln Leu Arg Val Val Met Met Lys Tyr Gly Leu Tyr Asn
                340                 345                 350
Ser Gln Phe Val Ala Leu Met Pro Thr Val Ser Ser Gln Val Thr
        355                 360                 365
Glu Ser Ser Glu Gly Phe Ser Pro Ile Phe Thr Asn Leu Phe Ser Lys
        370                 375                 380
Val Thr Ser Thr Gly Glu Ile Leu Arg Pro Asn Leu Gln Leu Met Arg
385                 390                 395                 400
Thr Ile Arg Arg Leu Phe Pro Arg Glu Cys Ala Arg Leu Ser Val Ile
                405                 410                 415
Ser Thr Leu Glu Ala Ala Gln Trp Ser Ile Arg Gly Ala Phe Gly Asp
            420                 425                 430
Leu Gly Asp Tyr His Pro Leu Ala Lys Phe Lys Thr Ala Phe Glu Tyr
        435                 440                 445
Asp Gln Arg Gln Leu Ile Asp Met Cys Ala Asp Arg Ala Pro Phe Val
        450                 455                 460
```

-continued

Asp Gln Ser Gln Ser Met Ser Leu Phe Ile Ser Glu Pro Ala Asp Gly
465                 470                 475                 480

Lys Leu Pro Ala Ser Arg Ile Met Asn Leu Leu Val His Ala Tyr Lys
            485                 490                 495

Cys Gly Leu Lys Thr Gly Met Tyr Tyr Cys Lys Leu Lys Lys Ala Thr
            500                 505                 510

Asn Ser Gly Val Phe Ser Gly Gly Glu Leu Ile Cys Thr Ser Cys His
            515                 520                 525

Leu

<210> SEQ ID NO 3
<211> LENGTH: 314
<212> TYPE: PRT
<213> ORGANISM: Feline herpesvirus 1

<400> SEQUENCE: 3

Met Pro Val Ser Ile Asp Ser Asp Cys Ser Ala Ser Arg Tyr Phe Tyr
 1               5                  10                  15

Thr Leu Glu Cys Pro Asp Ile Asn Met Leu Arg Ser Leu Ser Ile Ala
            20                  25                  30

Asn Arg Trp Leu Glu Thr Asp Leu Pro Ile Gly Asp Asp Ile Lys Asp
        35                  40                  45

Ile Thr Thr Leu Ser Glu Ser Glu Leu Asp Phe Tyr Arg Phe Leu Phe
    50                  55                  60

Thr Phe Leu Ser Ala Ala Asp Asp Leu Val Asn Leu Asn Leu Gly Asn
65                  70                  75                  80

Leu Ser Glu Leu Phe Thr Gln Lys Asp Ile Leu His Tyr Tyr Ile Glu
                85                  90                  95

Gln Glu Cys Ile Glu Val Val His Ser Arg Glu Tyr Ser Ala Ile Gln
            100                 105                 110

Leu Leu Leu Phe Lys Cys Asp Ala Glu Ala Arg Thr Ala Tyr Val Asp
        115                 120                 125

Ser Met Ile Thr Lys Pro Glu Leu Ala Arg Lys Val Glu Cys Val Arg
    130                 135                 140

Thr Arg Ile Gly Glu Cys Glu Ser Ile Ala Glu Lys Asp Ile Leu Met
145                 150                 155                 160

Ile Leu Ile Glu Gly Ile Phe Phe Val Ala Ser Phe Ala Ala Ile Ala
                165                 170                 175

Tyr Leu Arg Thr His Asn Ile Phe Ile Val Thr Cys Gln Thr Asn Asp
            180                 185                 190

Leu Ile Ser Arg Asp Glu Ala Ile His Thr Asn Ala Ser Cys Cys Ile
        195                 200                 205

Tyr Asn Asn Tyr Leu Pro Ala Gln Ile Lys Pro Ser Thr Glu Arg Ile
    210                 215                 220

His Ser Leu Phe Arg Glu Ala Val Glu Leu Glu Cys Glu Phe Ile Ser
225                 230                 235                 240

Thr Cys Ala Pro Arg Cys Ser Asn Leu Leu Asn Val Ala Asp Ile Cys
                245                 250                 255

Asn Tyr Val Arg Tyr Ser Ala Asp Arg Leu Leu Gly Ile Ile Lys Val
            260                 265                 270

Ala Pro Ile Phe Asn Val Pro Pro His Pro Asp Phe Pro Leu Ala
        275                 280                 285

Phe Met Val Ile Glu Lys His Thr Asn Phe Phe Glu Arg His Ser Thr
    290                 295                 300

Thr Tyr Ser Gly Thr Val Ile Asn Asp Leu
305                 310

<210> SEQ ID NO 4
<211> LENGTH: 454
<212> TYPE: PRT
<213> ORGANISM: Feline herpesvirus 1

<400> SEQUENCE: 4

Met Gly Leu Phe Gly Met Leu Lys Tyr Ala Tyr Cys Asn Arg Leu Val
 1               5                  10                  15

Lys His Asp Ala Ile Thr Thr Pro Pro Gly Ile Tyr Thr Pro Ile Ala
                20                  25                  30

Ile Asp Leu Trp Asn Val Met Tyr Thr Leu Met Gly Glu Ile Leu Ser
            35                  40                  45

Arg Glu Arg Tyr Thr Ser Asp Asn Ala Thr Val Thr Ala Glu Cys Phe
    50                  55                  60

Phe Ser Leu Leu Lys Leu Leu Gln Lys Arg Ser Tyr Phe Pro Ile Phe
65                  70                  75                  80

Val Ser Asp Arg Gly Ile Tyr Gly Asp Gly Asn Val Lys Tyr Gly Ala
                85                  90                  95

Lys Ala Ile Val Thr Gln Thr Met Cys Leu Gln Gly Gly Ser Gly Arg
                100                 105                 110

Leu Gly Glu Phe Ser Ile Pro His Gly Gly Pro Cys Glu Asp Thr Ser
            115                 120                 125

Glu Pro Asp Gly Gly Asn Pro Lys Asp Cys Lys Val Asp Ile Gln Glu
    130                 135                 140

Arg Ile Ser Ala Asp Trp Ser Ser Leu Ala Tyr Thr Pro Arg Leu Cys
145                 150                 155                 160

Tyr Arg Leu Cys Val Asn Leu Ile Arg Tyr Leu Gly Tyr Pro Tyr Val
                165                 170                 175

Asn Val Ser Asp Met Glu Ala Asp Val Cys Ala Asn Leu Tyr His
                180                 185                 190

Thr Asn Thr Val Ala Gln Ile Tyr Thr Thr Asp Thr Asp Leu Ile Leu
            195                 200                 205

Met Gly Cys Asp Ile Ile Leu Asp Ile Ile Pro Leu Phe Pro Pro Thr
    210                 215                 220

Ile Arg Cys Arg Asp Val Leu Ala Ser Leu Asn Leu Thr Tyr Ser Glu
225                 230                 235                 240

Phe Val Ala Arg Phe Val Arg Cys His Thr Asp Leu His Gln Thr Pro
                245                 250                 255

Ile Leu Lys Ser Val Gln Asn Leu Arg Ser Asn Gln Arg His Gln Ser
            260                 265                 270

Lys Thr Lys Val Lys Glu Lys Val Ile Asn Leu Lys Ser Ser Thr Ser
    275                 280                 285

Ile Cys Arg Asp Thr Ser Ser Asp Ala Ser Ser Glu Glu Arg Asp
290                 295                 300

Ile Glu Cys Met Ser Thr Asp Thr Tyr Arg Ile Ser Pro Ser Gln Ile
305                 310                 315                 320

Arg Gly Ser Ser Lys Gln Leu Thr Met Ile Glu Glu Gln Ser Leu Thr
                325                 330                 335

Leu Lys Tyr Thr Ser Arg Tyr Pro Pro Ile Met Lys Pro Arg His Arg
            340                 345                 350

Leu Ser His Phe Tyr Pro Arg His Arg Gln Asn Met Met Val Leu Glu

-continued

```
                355                 360                 365
Arg Lys Phe Ile Lys His Leu Ile Ala Arg Met Thr Pro Glu Thr Arg
            370                 375                 380

Gly Arg Leu Ser Ile Leu Lys Arg Val Pro Ile Leu Gln Glu Lys Ala
385                 390                 395                 400

Asn Phe Asn Leu Val Phe Glu Thr Leu Lys His Phe Ile Gly Asp Ala
                405                 410                 415

Ala Asn Ala Lys His Ile Thr Asn Leu Phe Trp Lys His Ile Ser Thr
            420                 425                 430

Pro Pro Asp Tyr Tyr Val Val Leu Val Thr Tyr Trp Asp Asp Cys Asp
                435                 440                 445

Ser Arg Arg Arg Tyr Asn
            450

<210> SEQ ID NO 5
<211> LENGTH: 395
<212> TYPE: PRT
<213> ORGANISM: Feline herpesvirus 1

<400> SEQUENCE: 5

Met Ala Phe Pro Pro Ser Arg Leu Glu Val Gly Ile Asn Lys Ala Ile
  1               5                  10                  15

Asn His Pro Ala Gln Val Val His Ala Gly Pro Leu Pro Gly Gly Val
                 20                  25                  30

Glu Ser Asn Thr Ile Phe Gly Asn Ala Val Leu Glu Glu Asp Lys Leu
             35                  40                  45

Arg Glu Val Met Thr Ile Leu Thr Pro Ile Ser Thr Ser Leu Lys Asn
     50                  55                  60

Ser Phe Leu Val Phe Ser Ala Asp Gly Met Leu Ile His Thr Ser Val
 65                  70                  75                  80

Cys His Glu Gln Ile Tyr Ile Pro Ile Ser Leu Asn Gln Phe Ser Ser
                 85                  90                  95

Tyr Arg Trp Thr Tyr Gly Gln Pro Ala Val Phe Leu Ala Asn Met His
                100                 105                 110

Gly Arg Arg Ser Leu Leu Asp Val Phe Lys Thr Thr Gly Arg Lys Ser
            115                 120                 125

Ala Thr Lys Lys Val Ile Phe Glu Ile Thr Asn Val His Pro Gly Arg
130                 135                 140

Met Leu Asn Gln Val Val Phe Asn Leu Asp Leu Asp Gly Gly Leu Ser
145                 150                 155                 160

Ser Ser Gln Leu Ile Lys Ser Glu Phe Asn Asn Tyr Cys Val Met Leu
                165                 170                 175

Pro Thr Arg Val Pro Asp Leu Thr Leu Glu Phe Ser Lys Pro Gln Leu
            180                 185                 190

Asn Lys Ile Leu Asp Leu Gly Lys Arg Ile Lys Ser Thr Leu Val Phe
        195                 200                 205

Glu Ser Thr Val Arg Glu Thr Ile Asn Ile Ile Ser Asp Val Gly Arg
    210                 215                 220

Val Thr Phe Thr Thr Thr His Glu Ser Ala Asp Gly Asn Gln Asp Ser
225                 230                 235                 240

Arg Cys Ile Leu Arg Ser Leu Pro Arg Ser His Ile Leu Gly Asn Val
                245                 250                 255

Ser Ser Thr Val Asn Phe Ser Gly Val Leu Lys Pro Phe Arg Leu Ala
            260                 265                 270
```

```
Leu Glu Ser Pro Val Asn Phe Phe Gln Leu Leu Arg Lys Leu Lys Val
            275                 280                 285

Thr His Thr Asp Val Ser Leu Asn Phe Phe Thr Pro Ser Thr Thr
    290                 295                 300

Pro Met Leu Ser Leu Thr Thr Arg Lys Pro Val Gly Val Met Met Phe
305                 310                 315                 320

Phe Phe Cys Thr Thr Gly Cys Leu Gly Ser Ser Glu Ser Ile Lys Thr
                325                 330                 335

Gly Asp Met Asp Asp Pro Ser Thr Thr Glu Glu Ser Ile Pro Arg
                340                 345                 350

Leu Lys Arg Arg Val Leu Glu Glu Phe Arg Asp Ser Glu Gly Pro Ser
            355                 360                 365

Lys Lys Leu Cys Thr Phe Val Tyr Ser Ser Pro Leu Cys Asn Pro Asn
    370                 375                 380

Pro Gly Thr Arg Gly Glu Asn Pro Ser Asp Ile
385                 390                 395

<210> SEQ ID NO 6
<211> LENGTH: 415
<212> TYPE: PRT
<213> ORGANISM: Feline herpesvirus 1

<400> SEQUENCE: 6

Met Ala Thr Asp Asp Cys Thr Ser Pro Thr Asn Ala Ala Gly Ser Ser
 1               5                  10                  15

Thr Thr Asn Asn Asn Gly Leu Ala Pro Glu Gly Ile Ser Asp Ile Thr
            20                  25                  30

Leu Pro Ser Phe Thr Val Arg Asn Cys Ser Gly Ser Arg Thr Gly Cys
        35                  40                  45

Ile Ala Cys Val Tyr Thr Ala Thr Lys Ala Leu Cys Tyr Ile Gly Val
    50                  55                  60

Gln Ser Gly Ile Leu Thr Ala Ser Ile Ala Leu Ile Trp Leu Leu Thr
65                  70                  75                  80

Arg Thr Thr Thr Tyr Ala Ala Gly Ile Leu Ile Phe Ile Ser Leu Ile
                85                  90                  95

Ser Thr Met Arg Leu Ser Met Val Lys Thr Glu Arg Ile Thr Thr Ile
            100                 105                 110

Cys Arg Phe Thr Gln Thr Leu Cys Val Ala Ile Ala Ala Val Gly Trp
        115                 120                 125

Ala Cys Asp Asp Leu Leu Gln Pro Val Gly Phe Thr Pro Leu Leu Leu
130                 135                 140

Leu Cys Leu Ala Gly Ile Ala Val Cys Ala Ala Ile Ile His Val Phe
145                 150                 155                 160

Tyr Phe Ile Cys Thr Ala Asn Gly Ser Gly Thr His Phe Arg Met Ala
                165                 170                 175

Ile Val Thr Met Thr Leu Gly Ala Leu Leu Gly Val Ser Ser Ile Ala
            180                 185                 190

Val Thr Val Lys Ser Glu Ile Leu Ile Gly Leu Gly Ile Ala Cys Ser
        195                 200                 205

Ile Ile Val Ser Gln Arg Asp Phe Gly Met Ile Leu Arg Asp Thr Cys
    210                 215                 220

His Tyr Arg Leu Gly Arg Tyr Ser Leu Met Arg Thr Phe Thr Asp Leu
225                 230                 235                 240

Gly Arg Gly Ala Asn His Asn Pro Val Asp Phe Ile Val Pro Asn Ile
                245                 250                 255
```

```
Glu Asp Val Tyr Glu Asp Lys Ile Ser Ser Val Lys Ile Phe Arg Glu
            260                 265                 270

His Pro Thr Leu Ile Met Ala Pro Leu Ile Gly Leu Thr Leu Thr Pro
            275                 280                 285

Pro Ile Trp Gly Tyr Cys His Ile Thr Lys Tyr Gly His Asp Phe Gln
            290                 295                 300

Thr Pro Leu Thr Val Val Ile Cys Val Ile Val Gly His Cys Leu Ala
305                 310                 315                 320

Phe Cys Leu Glu Pro Leu Met Val Tyr Arg Arg Met Tyr Ile Pro Glu
            325                 330                 335

Val Leu Val Ser Phe His Gly Met Ala Glu Ile Thr Gly Ile Val Leu
            340                 345                 350

Ala Leu Leu Gly Val Asn Phe Gly Thr Pro Leu Val Leu Thr Leu Ala
            355                 360                 365

Ile Ser Glu Thr Leu Thr Cys Leu Leu His Leu Arg Lys Ile Ile Leu
            370                 375                 380

Gly Ala Lys Arg Leu Ala Ala Thr Tyr Leu Cys Arg Gly Leu His Thr
385                 390                 395                 400

Gly Met Tyr Val Thr Ala Gly Met Cys Tyr Leu Tyr Ser His Met
            405                 410                 415

<210> SEQ ID NO 7
<211> LENGTH: 484
<212> TYPE: PRT
<213> ORGANISM: Feline herpesvirus 1

<400> SEQUENCE: 7

Met Ser Ala Thr Thr Pro Ile Ser Gln Pro Thr Ser Pro Phe Thr Thr
  1               5                  10                  15

Pro Thr Arg Arg Ser Thr Asn Ile Ala Thr Ser Ser Ser Thr Thr Gln
             20                  25                  30

Ala Ser Gln Pro Thr Ser Thr Leu Thr Thr Leu Thr Arg Ser Ser Thr
         35                  40                  45

Thr Ile Ala Thr Ser Pro Ser Thr Thr Gln Ala Ala Thr Phe Ile Gly
     50                  55                  60

Ser Ser Thr Asp Ser Asn Thr Thr Leu Leu Lys Thr Thr Lys Lys Pro
 65                  70                  75                  80

Lys Arg Lys Lys Asn Lys Asn Asn Gly Ala Arg Phe Lys Leu Asp Cys
             85                  90                  95

Gly Tyr Lys Gly Val Ile Tyr Arg Pro Tyr Phe Ser Pro Leu Gln Leu
            100                 105                 110

Asn Cys Thr Leu Pro Thr Glu Pro His Ile Thr Asn Pro Ile Asp Phe
            115                 120                 125

Glu Ile Trp Phe Lys Pro Arg Thr Arg Phe Gly Asp Phe Leu Gly Asp
            130                 135                 140

Lys Glu Asp Phe Val Gly Asn His Thr Arg Thr Ser Ile Leu Leu Phe
145                 150                 155                 160

Ser Ser Arg Asn Gly Ser Val Asn Ser Met Asp Leu Gly Asp Ala Thr
            165                 170                 175

Leu Gly Ile Leu Gln Ser Arg Ile Pro Asp Tyr Thr Leu Tyr Asn Ile
            180                 185                 190

Pro Ile Gln His Thr Glu Ala Met Ser Leu Gly Ile Lys Ser Val Glu
            195                 200                 205

Ser Ala Thr Ser Gly Val Tyr Thr Trp Arg Val Tyr Gly Gly Asp Gly
```

-continued

```
                 210                 215                 220
Leu Asn Lys Thr Val Leu Gly Gln Val Asn Val Ser Val Val Ala Tyr
225                 230                 235                 240

His Pro Pro Ser Val Asn Leu Thr Pro Arg Ala Ser Leu Phe Asn Lys
                245                 250                 255

Thr Phe Glu Ala Val Cys Ala Val Ala Asn Tyr Phe Pro Arg Ser Thr
                260                 265                 270

Lys Leu Thr Trp Tyr Leu Asp Gly Lys Pro Ile Glu Arg Gln Tyr Ile
                275                 280                 285

Ser Asp Thr Ala Ser Val Trp Ile Asp Gly Leu Ile Thr Arg Ser Ser
290                 295                 300

Val Leu Ala Ile Pro Thr Thr Glu Thr Asp Ser Glu Lys Pro Asp Ile
305                 310                 315                 320

Arg Cys Asp Leu Glu Trp His Glu Ser Pro Val Ser Tyr Lys Arg Phe
                325                 330                 335

Thr Lys Ser Val Ala Pro Asp Val Tyr Tyr Pro Pro Thr Val Ser Val
                340                 345                 350

Thr Phe Ala Asp Thr Arg Ala Ile Cys Asp Val Lys Cys Val Pro Arg
                355                 360                 365

Asp Gly Ile Ser Leu Met Trp Lys Ile Gly Asn Tyr His Leu Pro Lys
                370                 375                 380

Ala Met Ser Ala Asp Ile Leu Ile Thr Gly Pro Cys Ile Glu Arg Pro
385                 390                 395                 400

Gly Leu Val Asn Ile Gln Ser Met Cys Asp Ile Ser Glu Thr Asp Gly
                405                 410                 415

Pro Val Ser Tyr Thr Cys Gln Thr Ile Gly Tyr Pro Pro Ile Leu Pro
                420                 425                 430

Gly Phe Tyr Asp Thr Gln Val Tyr Asp Ala Ser Pro Glu Ile Val Ser
                435                 440                 445

Glu Ser Met Leu Val Ser Val Val Ala Val Ile Leu Gly Ala Val Leu
                450                 455                 460

Ile Thr Val Phe Ile Phe Ile Thr Ala Leu Cys Leu Tyr Tyr Ser His
465                 470                 475                 480

Pro Arg Arg Leu

<210> SEQ ID NO 8
<211> LENGTH: 193
<212> TYPE: PRT
<213> ORGANISM: Feline herpesvirus 1

<400> SEQUENCE: 8

Met Gln Gly Met Arg Ser Thr Ser Gln Pro Leu Val Glu Ile Pro Leu
 1               5                  10                  15

Val Asp Met Glu Pro Gln Pro Ser Ile His Ser Asn Glu Pro Asn Pro
                20                  25                  30

Pro Asn Lys Met Leu Thr Thr Ala Ile Ser Ser Arg Arg Ser Gly Ile
            35                  40                  45

Phe Leu Phe Ser Leu Gly Met Phe Phe Gly Val Ile Leu Thr Ala
        50                  55                  60

Thr Ile Ile Val Cys Thr Phe Ile Phe Thr Ile Pro Val Asp Met Leu
65                  70                  75                  80

Gln Met Pro Arg Cys Pro Gly Gly Thr Val Gly Ile Lys Asn Cys Cys
                85                  90                  95

Ile Arg Pro Ile Arg Arg His Val Lys Ser His Gln Asp Leu Val Ala
```

```
            100             105             110
Thr Cys Ala Glu Tyr Met Glu Gln Pro Ala Thr Ala Ser Ala Val Gly
            115             120             125

Ala Leu Ile Pro Leu Leu Asp Ile Phe Asn Gly Asp Gly Ile Ser Thr
        130             135             140

Asn Asp Ser Leu Tyr Asp Cys Ile Leu Ser Asp Glu Lys Lys Ser Cys
145             150             155             160

Asn Thr Ser Met Ala Val Cys Gln Ser Thr Tyr Leu Pro Asn Pro Leu
            165             170             175

Ser Asp Phe Ile Met Arg Val Arg Gln Ile Phe Ser Gly Ile Leu Asn
            180             185             190

His

<210> SEQ ID NO 9
<211> LENGTH: 298
<212> TYPE: PRT
<213> ORGANISM: Feline herpesvirus 1

<400> SEQUENCE: 9

Ile Leu Gly Ser Ile Glu Arg Gly Arg Arg Ser Thr Arg Glu Arg
1               5               10              15

Ala Lys Thr Glu Arg Arg Cys Val Ser Gln Met Met Thr His Ile Asp
            20              25              30

Arg Gln Ser Leu Pro Leu Pro Ser Pro Pro Thr Pro His Ala His His
        35              40              45

Asp Val Thr Tyr Pro Pro Ala Val Ile Thr Pro Pro Asn Pro Tyr Met
    50              55              60

Gly Met Ala Ser Leu Leu Ala Ser Pro Leu Thr Pro Arg Asp Ile Ser
65              70              75              80

Ser Pro Gly Leu Gly Asp His Pro Ser Asn Thr Pro Asp Gly Val Glu
            85              90              95

Gly Cys Phe His Arg Thr Pro Leu Arg Ser Asp Ala Arg Thr Lys Gln
            100             105             110

Leu Asp Asp Arg Phe Asp Ser Ser Asp Cys Asp Gly Thr Pro Tyr Thr
        115             120             125

Ser Leu Asp Asp Ile Arg Pro Glu Glu Ser Glu Asp His Ile Asn Asn
    130             135             140

Pro Ser Tyr Gly Leu Thr Glu Thr Phe Asn Ser Ser Asn Leu Ser Asn
145             150             155             160

Gly Asp Glu Pro Arg Asp Ala Tyr Asn Thr His Tyr Gln His Pro Arg
            165             170             175

Cys Ile Ser Pro Glu Asp Thr Ala Gln Ser Arg Gly Ser Ser Ala Ser
            180             185             190

Gly Thr Thr Ser Gln Leu Gln Tyr Thr Glu His Tyr Gln Thr Pro Ile
        195             200             205

Cys His Lys Lys Cys Gln Cys Ser Lys Pro Gly Gly Pro Lys Gly Asp
    210             215             220

Tyr Pro Glu Leu Tyr Asn Glu Cys Gly Asp Val Lys Lys Asn Leu Pro
225             230             235             240

Arg Arg Arg Ser Ser Pro Gly Ile Glu Glu Val Val Glu Arg Phe
            245             250             255

Arg Pro Arg Ser Arg Leu Leu Asp Asp Thr Tyr Gly Ile Glu Thr Leu
        260             265             270

Ala Thr Leu Asn Ala Ser Ser Ile Lys Arg Ala His Gly Thr Ser Arg
```

```
                    275                 280                 285
Val Asp Phe Gln Thr His Ala Ile Arg Lys
    290                 295

<210> SEQ ID NO 10
<211> LENGTH: 24
<212> TYPE: DNA
<213> ORGANISM: Feline herpesvirus 1

<400> SEQUENCE: 10
cttgccgggg tttaaaccgg ttcg                                          24

<210> SEQ ID NO 11
<211> LENGTH: 32
<212> TYPE: DNA
<213> ORGANISM: Feline herpesvirus 1

<400> SEQUENCE: 11
aattcgaacc ggtttaaacc ccggcaaggt ac                                 32

<210> SEQ ID NO 12
<211> LENGTH: 32
<212> TYPE: DNA
<213> ORGANISM: Feline herpesvirus 1

<400> SEQUENCE: 12
tgcaaagctt atcgatcccg gggcccggtg ca                                 32

<210> SEQ ID NO 13
<211> LENGTH: 32
<212> TYPE: DNA
<213> ORGANISM: Feline herpesvirus 1

<400> SEQUENCE: 13
ccgggccccg ggatcgataa gctttgcatg ca                                 32

<210> SEQ ID NO 14
<211> LENGTH: 21
<212> TYPE: DNA
<213> ORGANISM: Feline herpesvirus 1

<400> SEQUENCE: 14 ggggccgtt taaaccggta c                                              21

<210> SEQ ID NO 15
<211> LENGTH: 17
<212> TYPE: DNA
<213> ORGANISM: Feline herpesvirus 1

<400> SEQUENCE: 15
cggtttaaac ggccccc                                                  17

<210> SEQ ID NO 16
<211> LENGTH: 28
<212> TYPE: DNA
<213> ORGANISM: Feline herpesvirus 1

<400> SEQUENCE: 16
tcgagaaagc ttatcgatcc cgggcccg                                      28

<210> SEQ ID NO 17
<211> LENGTH: 28
<212> TYPE: DNA
```

-continued

```
<213> ORGANISM: Feline herpesvirus 1

<400> SEQUENCE: 17
tcgacgggcc cgggatcgat aagctttc                                    28

<210> SEQ ID NO 18
<211> LENGTH: 40
<212> TYPE: DNA
<213> ORGANISM: Feline herpesvirus 1

<400> SEQUENCE: 18
tttgagctcg cggccgcatg aagtaatttt gctaatactc                       40

<210> SEQ ID NO 19
<211> LENGTH: 27
<212> TYPE: DNA
<213> ORGANISM: Feline herpesvirus 1

<400> SEQUENCE: 19
tttggtaccg tttagttaca ccatatg                                     27

<210> SEQ ID NO 20
<211> LENGTH: 30
<212> TYPE: DNA
<213> ORGANISM: Feline herpesvirus 1

<400> SEQUENCE: 20
ttgggtaccg cctcgactct aggcggccgc                                  30

<210> SEQ ID NO 21
<211> LENGTH: 32
<212> TYPE: DNA
<213> ORGANISM: Feline herpesvirus 1

<400> SEQUENCE: 21
ttgggtaccg gatccgaaaa aacctcccac ac                               32

<210> SEQ ID NO 22
<211> LENGTH: 39
<212> TYPE: DNA
<213> ORGANISM: Feline herpesvirus 1

<400> SEQUENCE: 22
tttgagctcg cggccgcatg attgtgctcg taacttgcc                        39

<210> SEQ ID NO 23
<211> LENGTH: 38
<212> TYPE: DNA
<213> ORGANISM: Feline herpesvirus 1

<400> SEQUENCE: 23
tttggtaccg tttagtggac atgcactttt tcaattgg                         38

<210> SEQ ID NO 24
<211> LENGTH: 95
<212> TYPE: DNA
<213> ORGANISM: Feline herpesvirus 1

<400> SEQUENCE: 24
atgaagctta gtggttatgg tcaacccata gcctcgacac taagtaacat cacactacca  60
atgcaggata acaatactgt tgtgtactgt attcg                             95
```

-continued

```
<210> SEQ ID NO 25
<211> LENGTH: 88
<212> TYPE: DNA
<213> ORGANISM: Feline herpesvirus 1

<400> SEQUENCE: 25
aaaaatattg taccataaag aactttgca agtggaatga acataaactg agaattggtt    60
agaacgaata cagtacacaa cagtattg                                      88

<210> SEQ ID NO 26
<211> LENGTH: 20
<212> TYPE: DNA
<213> ORGANISM: Feline herpesvirus 1

<400> SEQUENCE: 26
atgaagctta gtggttatgg                                               20

<210> SEQ ID NO 27
<211> LENGTH: 20
<212> TYPE: DNA
<213> ORGANISM: Feline herpesvirus 1

<400> SEQUENCE: 27
aaaaatattg taccataaag                                               20

<210> SEQ ID NO 28
<211> LENGTH: 20
<212> TYPE: DNA
<213> ORGANISM: Feline herpesvirus 1

<400> SEQUENCE: 28
ggacaatatt tttaatcaag                                               20

<210> SEQ ID NO 29
<211> LENGTH: 36
<212> TYPE: DNA
<213> ORGANISM: Feline herpesvirus 1

<400> SEQUENCE: 29
tttaacaacc tgctcattgg ttcctgtacg tgcagc                             36

<210> SEQ ID NO 30
<211> LENGTH: 36
<212> TYPE: DNA
<213> ORGANISM: Feline herpesvirus 1

<400> SEQUENCE: 30
aagttttatg ttgctgcacg tacaggaacc aatgag                             36

<210> SEQ ID NO 31
<211> LENGTH: 20
<212> TYPE: DNA
<213> ORGANISM: Feline herpesvirus 1

<400> SEQUENCE: 31
atcactaaca tttttaaagc                                               20

<210> SEQ ID NO 32
<211> LENGTH: 37
<212> TYPE: DNA
<213> ORGANISM: Feline herpesvirus 1

<400> SEQUENCE: 32
```

-continued

```
tttgagctcg cggccgcatg gccacacagg gacaacg                                37
```

<210> SEQ ID NO 33
<211> LENGTH: 33
<212> TYPE: DNA
<213> ORGANISM: Feline herpesvirus 1

<400> SEQUENCE: 33

```
tttggtaccg tttagttcgt aacctcatca atc                                    33
```

RECOMBINANT VACCINE CONTAINING FELINE HERPES VIRUS TYPE 1 PARTICULARLY FOR TREATING FELINE INFECTIOUS PERITONITIS

This application is a division of allowed U.S. application Ser. No. 09/080,044, filed May 15, 1998, now U.S. Pat. No. 6,074,649, as a continuation of PCT/FR96/01830, filed Nov. 19, 1996, designating the U.S. and claiming priority from French application No. 95/14450, filed Nov. 30, 1995.

The present invention relates to vaccines, preferably for cats, produced from recombinant feline herpesviruses, and to the methods for obtaining and preparing these recombinant viruses. In particular, the present invention relates more particularly to the feline herpesvirus recombinants comprising an expression cassette for one or more foreign genes.

Feline infectious rhinotracheitis is caused by feline herpesvirus type 1 (FHV-1). Feline herpesvirus (FHV-1) is classified in the Alphaherpesviridae family. Feline infectious rhinotracheitis is a disease which is very widespread in cats and, in practice, all medicated cats are vaccinated against this viral condition. There are currently several vaccines for preventing infectious rhinotracheitis. These vaccines are either of the attenuated live type, or of the inactivated type (whole virus or purified subunits). The attenuation of the live vaccines currently used has been obtained by repeated passages on cells, and the cause of their attenuation is not known. Furthermore, these vaccines exhibit, in general, a residual virulence and are for this reason administered via the parenteral (subcutaneous or intramuscular) route rather than via the intranasal route (which would nevertheless be the preferred route given the local replication of this virus). Inactivated vaccines exhibit good safety, but their weak immunogenicity requires multiple injections in order to induce a satisfactory protection.

Moreover, domestic cats are exposed to numerous other diseases, and the development of a vaccinal vector which can express various antigens of feline pathogenic agents would make it possible to simplify and improve the efficacy of vaccination programmes.

Finally, among the diseases affecting domestic cats, some are still resistant to conventional vaccinal approaches. The most well known case is that of feline infectious peritonitis caused by a coronavirus (feline infectious peritonitis (FIP) virus or FIPV).

An FHV-1 vector, whose attenuation would be such that it can be administered via the oronasal route in cats without causing local and/or general pathology, and which would allow the induction of a protective immune response both against feline infectious rhinotracheitis and against other feline pathogenic agents would constitute a significant advance in the field of vaccination of domestic feline populations.

A number of FHV genes have already been proposed as insertion sites: Patent Application EP-A-0,447,303 proposed insertion into the RR2 site of alphaherpesviruses, including FHV. The application gives the means for carrying out the insertion into the RR2 site of the turkey herpesvirus (HVT virus). Patent Application WO-A-90 01547 proposes FHV TK-vectors for the expression of heterologous genes. Likewise, Patent Application WO-A-93 09238 proposes a vaccine against feline leukaemia formed of an FHV vector in which an FHV gene has been inserted into the TK gene of the FHV virus. See also along the same lines the articles by R. C. Wardley et al. in J. Gen. Virol. 1992. 73. 1811–1818 and by G. E. Cole et al. in J. Virol. 1990. 64. 4930–4938. Patent Application WO-A-94 03621 proposes insertion into the gI, gE, US9, US10 and US11 genes. Patent Application WO-A-95 00172 proposes inserting a DNA serving as marker into the region of the genome comprising the gI and gE genes. Patent Application EP-A-0,576,092 proposes the open reading frame (ORF) situated between the gC gene and the homologous gene of the HSV-1 UL46 gene as preferential site for insertion into the FHV genome. See also M. J. Willemse et al. in J. Gen. Virol. 1994. 75. 3107–3116.

Various promoters, including those generally commercially available, have been used in the various constructs described in the prior art, among which are the HCMV IE (human CMV immediate early) promoter, the promoter sequence of the LTR region of the RSV virus (Rous Sarcoma Virus), and the SV40 virus early promoter.

The aim of the present invention is to provide a live FHV vaccine, which is attenuated but which has conserved a good capacity for replication in vivo, for immunizing cats against infectious rhinotracheitis.

Another aim of the invention is to provide a recombinant live vaccine based on FHV which is effective against other feline pathogenic agents. In particular, because of the numerous failures observed in vaccination against feline infectious peritonitis with inactivated or attenuated live vaccines, mainly because of the phenomenon of "facilitation" (exacerbation of the disease), the need still exists for a vaccine which is really effective against FIP. Such a vaccine based on a recombinant FHV-1 vector which would be really effective against feline infectious peritonitis, a disease for which no one has yet marketed a satisfactory vaccine, could, in addition, pave the way for highly effective vaccines against other cat diseases such as, for example, and inter alia, feline leukaemia, feline immunodeficiency syndrome due to FIV, or feline panleukopenia.

Yet another aim of the invention is to allow an effective vaccination of cats using the oronasal route.

The applicant has characterized a new part of the FHV genome, in which it has characterized new regions of the FHV virus genome, regions called hereinafter (see Example 3) FHV ORF2 and FHV ORF5, which have proved utilizable for the insertion of foreign genes under conditions which make it possible to meet the objectives set out above.

The subject of the present invention is therefore a recombinant live vaccine using, as vector, a feline herpesvirus comprising, and expressing, at least one nucleotide sequence encoding a polypeptide, this sequence being inserted into the ORF5 site and/or ORF2 site.

Preferably, the inserted sequence encodes an antigenic polypeptide and, preferentially, an antigenic polypeptide of a feline pathogenic agent. Sequences encoding immunomodulatory proteins such as cytokines may also be inserted. According to an advantageous feature, it is possible to combine a sequence encoding a cytokine, and the like, with a sequence encoding an antigen. If necessary, several cytokine sequences may be combined with each other, optionally in combination with one or more sequences encoding antigens.

Insertion into the two sites newly characterized is carried out by simple insertion (without deletion) or after partial or total deletion of the ORFs used as insertion sites.

According to a particularly preferred feature of the invention, insertions and/or deletions are carried out in the two sites described. This feature is particularly adapted to the use of virulent wild-type strains of the FHV-1 virus for obtaining recombinants. It is therefore possible to insert at least one nucleotide sequence into each of the sites, or alternatively to insert into only one site, preferably ORF5, and to delete all or part of the other site.

According to another feature, which applies more to the attenuated vaccinal strains, without being limited thereto, the insertion is carried out in only one of the two sites, preferably the ORF5 site.

The feline herpesviruses according to the invention are preferably FHV viruses type 1.

It is possible to use, in particular, the FHV-1 CO strain in which the sequence of the genomic region (ORF1 to ORF8) is indicated in the sequence listing under the reference SEQ ID No. 1 (see also Table 1 Example 3). The ORF2 site is situated between nucleotides 1655 and 2596. The ORF5 site is situated between nucleotides 5869 and 7113.

For the expression of the foreign genes inserted into the FHV-1 genome according to the present invention, a strong eukaryotic promoter such as, preferentially, a CMV immediate early (IE) promoter will be preferably used. A CMV IE promoter is understood to mean especially a fragment as given in the example as well as its subunits such conserve the same promoter activity. The CMV IE promoter may be the human promoter (HCMV IE) or the murine promoter (MCMV IE), or alternatively a CMV IE promoter of another origin, for example from rats, guinea pigs or pigs.

It will be possible to insert at least two nucleotide sequences into one of the ORF2 or ORF5 sites under the control of different promoters. These may be especially CMV IE promoters of different origins.

According to an advantageous development of the invention, another promoter is combined with the CMV IE promoter according to a tandem arrangement, such as the 5' ends of both promoters are adjacent therebetween and the transcriptions from these promoters go in opposite directions, which makes it possible to insert, into the region of insertion, two nucleotide sequences, one under the control of the CMV IE promoter, the other under that of the associated promoter. This construct is remarkable in that the presence of the CMV IE promoter, and especially of its enhancer part, may enhance the transcription induced by the associated promoter. As associated promoter, there may be mentioned, for example, a CMV promoter from a species different from the first promoter. It is also possible to envisage other promoters such as the RNA1.8 promoter from the Marek's disease virus (MDV) (G. Bradley et al. J. Virol. 1989. 63. 2534–2542).

The nucleotide sequence inserted into the FHV vector so as to be expressed may be any sequence encoding an antigenic polypeptide of a feline pathogenic agent capable, once expressed under the favourable conditions offered by the invention, of providing immunization leading to an effective protection of the vaccinated animal against the pathogenic agent. It is therefore possible to insert, under the conditions described by the present invention, the nucleotide sequences encoding the antigens of interest for a given disease.

The typical case of the invention is the insertion of at least one nucleotide sequence suitably encoding a polypeptide of the feline infectious peritonitis virus (FIP or FIPV) and, preferably, the FIPV M poly-peptide or the modified FIPV S polypeptide. A recombinant live vaccine is thus obtained which provides, in addition to protection against feline infectious rhinotracheitis, protection against feline infectious peritonitis. If desired, a sequence encoding another antigen of the FIP virus, such as the N protein, the 7b protein and/or the polypeptides encoded by the polymerase (polB) gene of the FIP virus can also be inserted in addition or instead.

Other preferred cases of the invention are the insertion of nucleotide sequences encoding antigens or fragments of antigens of the feline leukaemia virus (FeLV), in particular env, gag and pol genes (Osterhaus A. et al. J. Immunol., 1985. 135. 591–596; Lutz H. Vet. Microbiol. 1990. 23. 131–146; Clark N. et al. JAVMA, 1991. 199. 1433–1443; Thomsen D. et al. J. Gen. Virol., 1992. 73. 1819–1824), of the feline immunodeficiency virus (FIV) (Jarrett O. et al. AIDS, 1990, 4 (suppl. 1): S163–S165; Miyazawa T. et al. Arch. Virol; 1994, 134, 221–234; de Rhonde A. et al. Virology, 1994. 198. 257–264), in particular env, gag and pol genes, of the feline panleukopenia virus (FPV) (Carlson J. et al. J. Virol. 1985. 55. 574–582; Martyn J. et al. J. Gen. Virol. 1990. 71, 2747–2753), in particular the VP2 capsid gene, of the feline calicivirus (FCV) (Neill J. et al. J. Virol. 1991. 65. 5440–5447; Carter M. et al. Virology. 1992. 190 443–448), in particular the capsid gene.

A typical case of the invention is a vaccine comprising a nucleotide sequence encoding an antigen of the FIP virus under the control of CMV IE and a nucleotide sequence encoding an antigen of another feline viral disease, especially those mentioned above, under the control of another promoter.

The subject of the present invention is also a polyvalent vaccine formula comprising, in the form of a mixture or to be mixed, at least two recombinant live vaccines as defined above, these vaccines comprising different inserted sequences, especially from different pathogens.

The subject of the present invention is also the FHV viruses modified in one or both ORF2 and ORF5 sites as indicated above.

Its subject is also a method of vaccination, in particular of cats, in which an effective quantity of a vaccine as defined above is administered by any parenteral or local route, but preferably by the oronasal route. The vaccinal dose will be between $10^2$ CCID$_{50}$ and $10^7$ CCID$_{50}$. As defined, the vaccine is effective in general after only one administration by the oronasal route. However, repeated administrations may be necessary.

The subject of the present invention is also the DNA fragments comprising all or part of the sequence defined by positions 1 to 8193 on SEQ ID No. 1, especially all or part of the ORF2 and ORF5 sites defined and/or of the flanking sequences located upstream and downstream of these sites, which fragments will be useful as flanking arms for the techniques of homologous recombination with the genome of the parenteral FHV virus. Of course, the invention also relates to the variants of these fragments which correspond to the equivalent sequences of the other FHV strains. The specialist is quite free to choose the regions serving as flanking arms in conjunction with the type of insertion (with or without deletion) or deletion (partial or total) chosen. In general, the flanking arms can thus have from 100 to 800 base pairs.

BRIEF DESCRIPTION OF THE DRAWINGS

The invention will now be described in greater detail with the aid of nonlimiting exemplary embodiments, taken with reference to the drawing, in which:

FIG. 1: sequence of the FHV-1 region (10803 base pairs) and translation of the different open reading frames (ORF) present in this sequence (ORF1 to ORF8).

Figure 2:
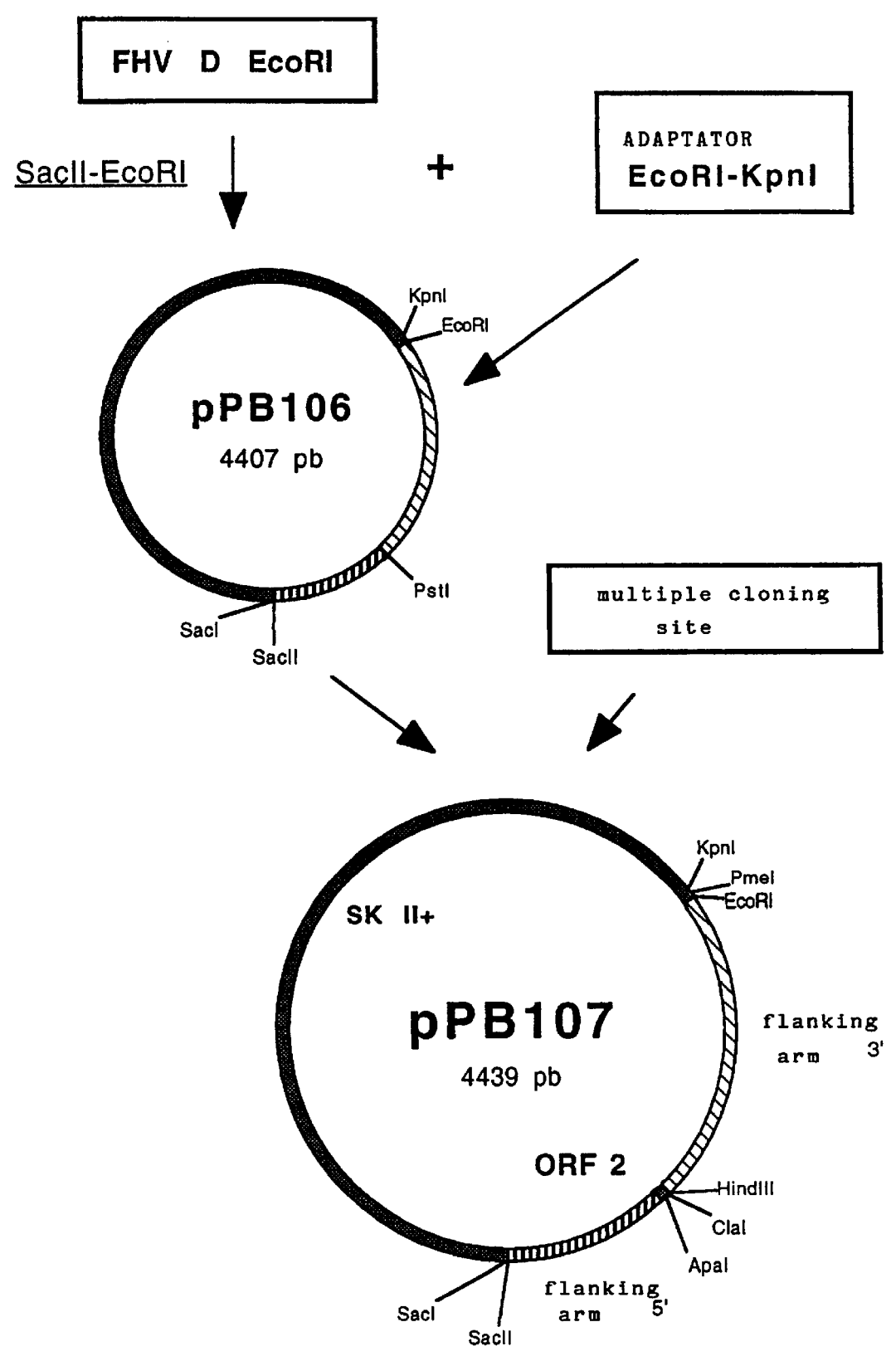

FIG. 2: Construction of the plasmid pPB107 (donor plasmid for the insertion of expression cassettes into the FHV-1 ORF2 site)

Figure 3:
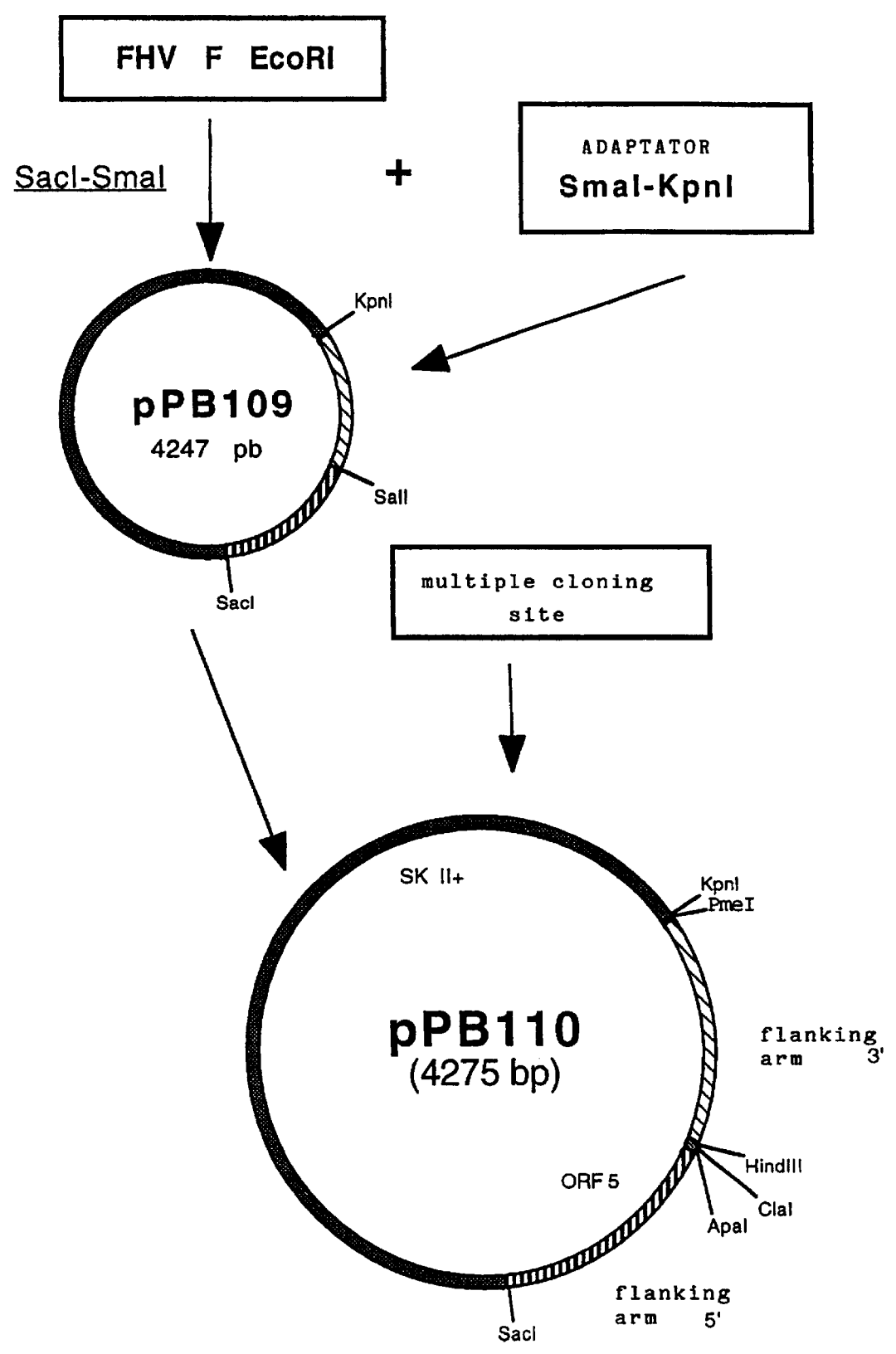

FIG. 3: Construction of the plasmid pPB110 (donor plasmid for the insertion of expression cassettes in the FHV-1 ORF5 site)

Figure 4:
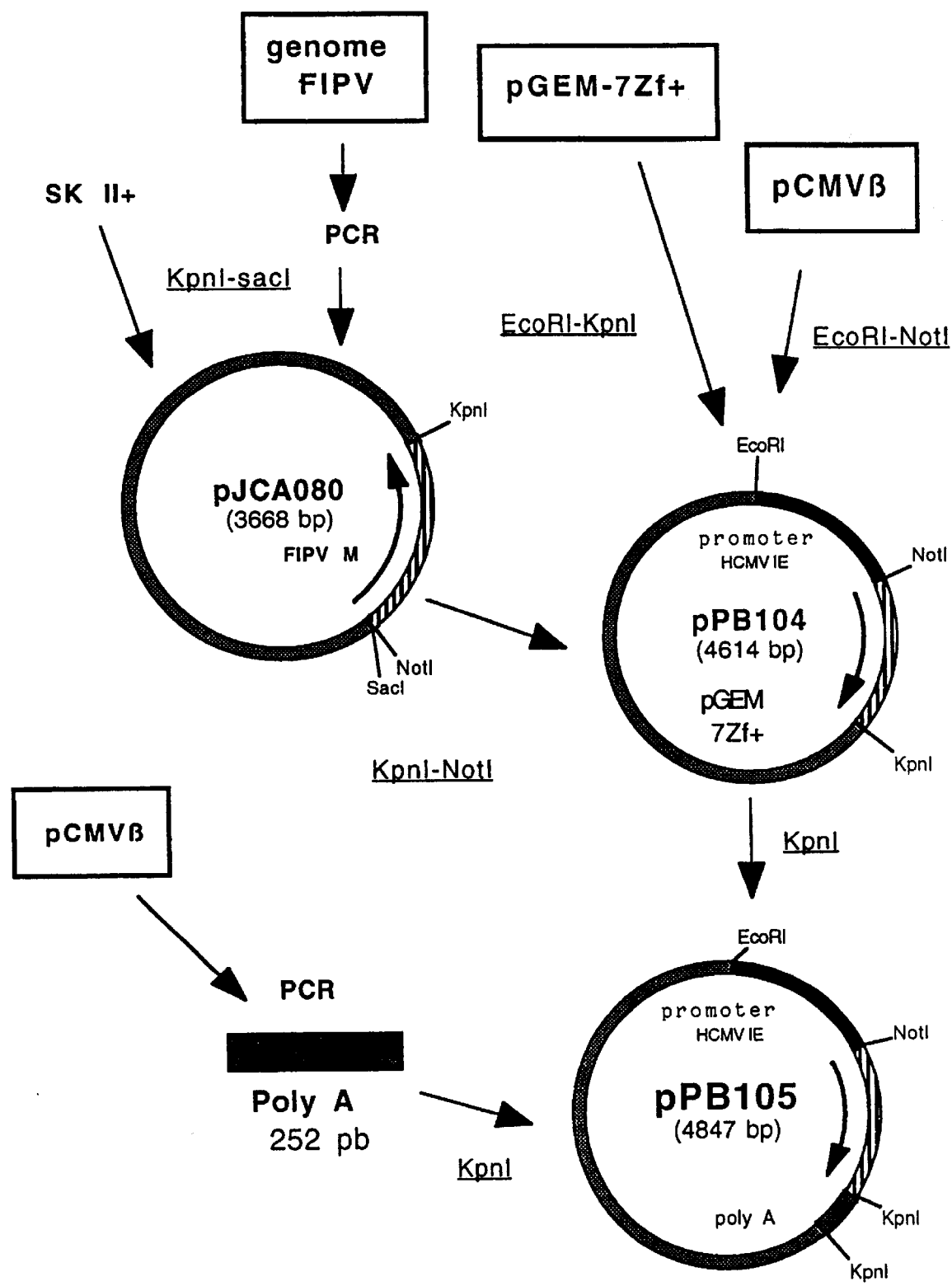
FIG. 4: Construction of the expression cassette for the FIPV M gene (plasmid pPB105)
Figure 5:
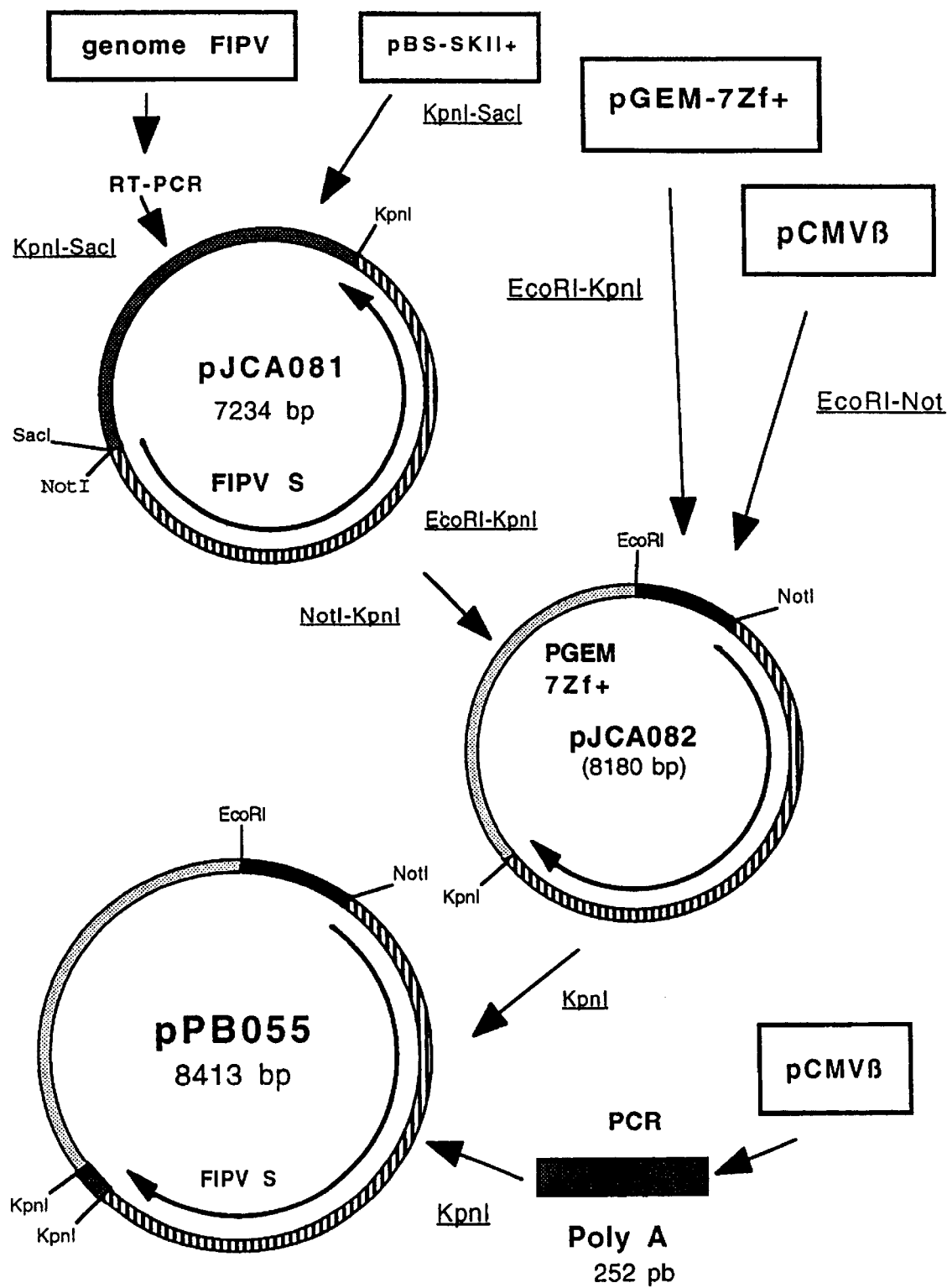
FIG. 5: Construction of the expression cassette for the FIPV S gene (plasmid pPB055)
Figure 6:
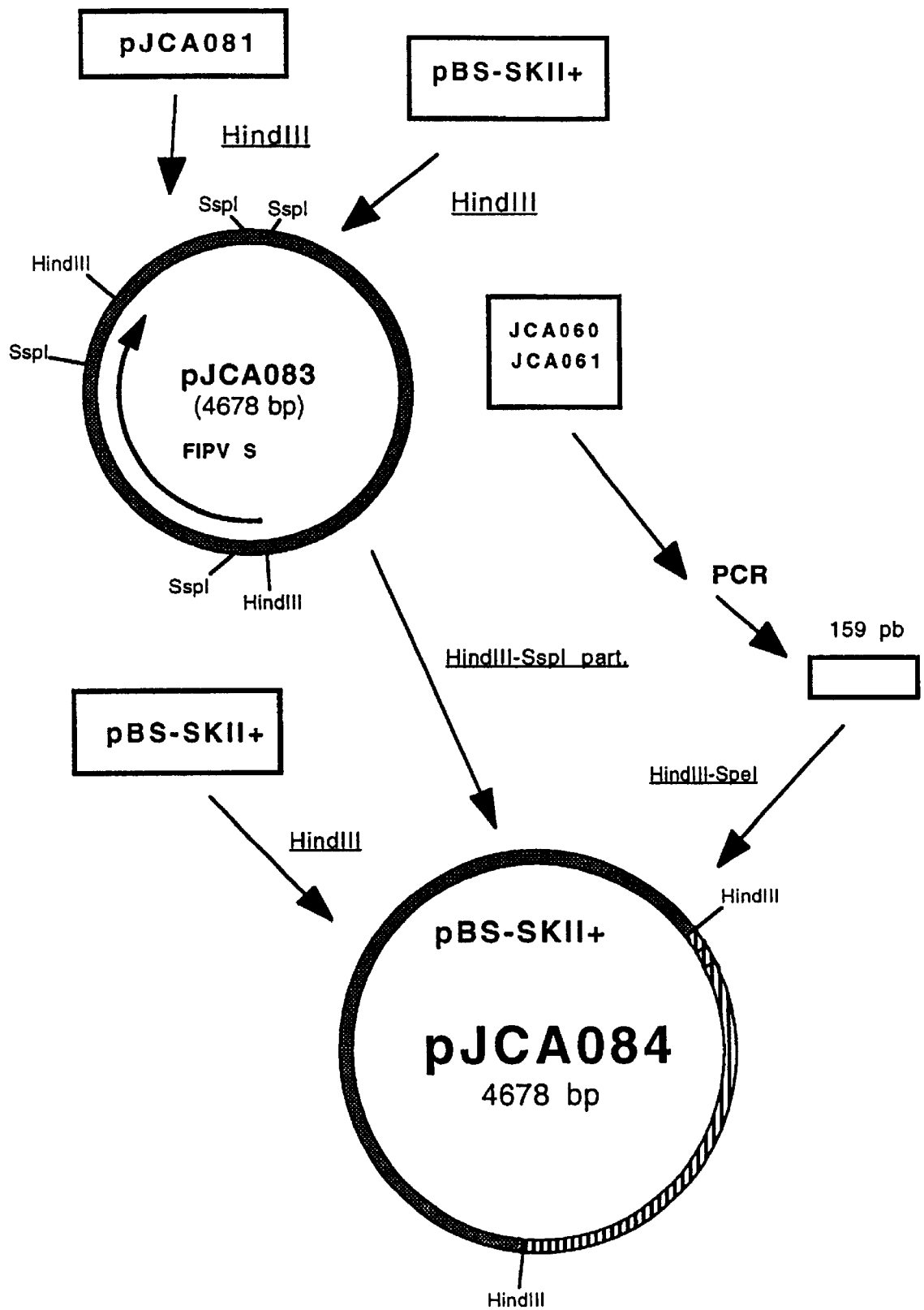
FIG. 6: Mutagenesis of the A1 site of the FIPV S gene (plasmid pJCA084)
Figure 7:
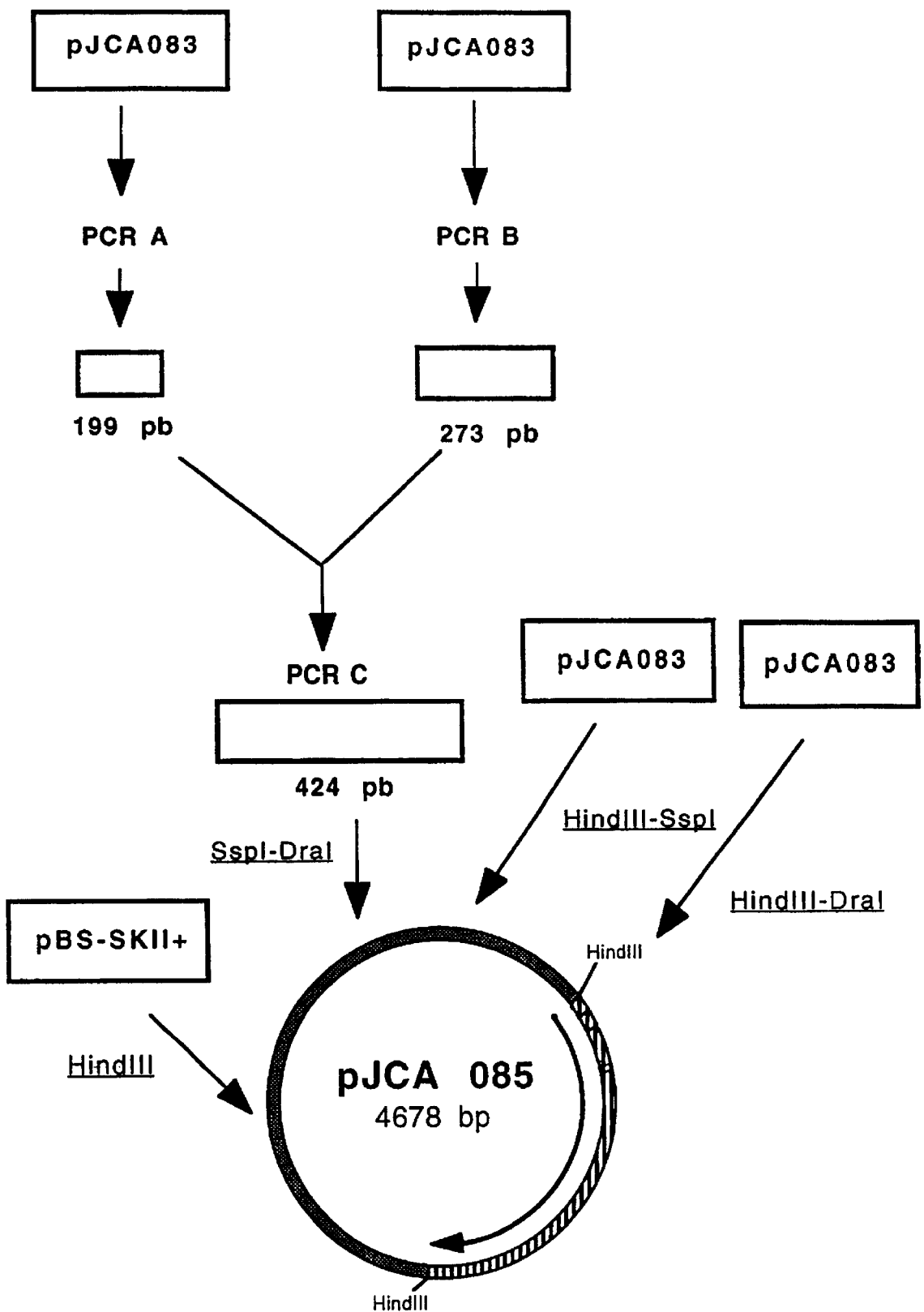
FIG. 7: Mutagenesis of the A2 site of the FIPV S gene (plasmid pJCA085)
Figure 8:
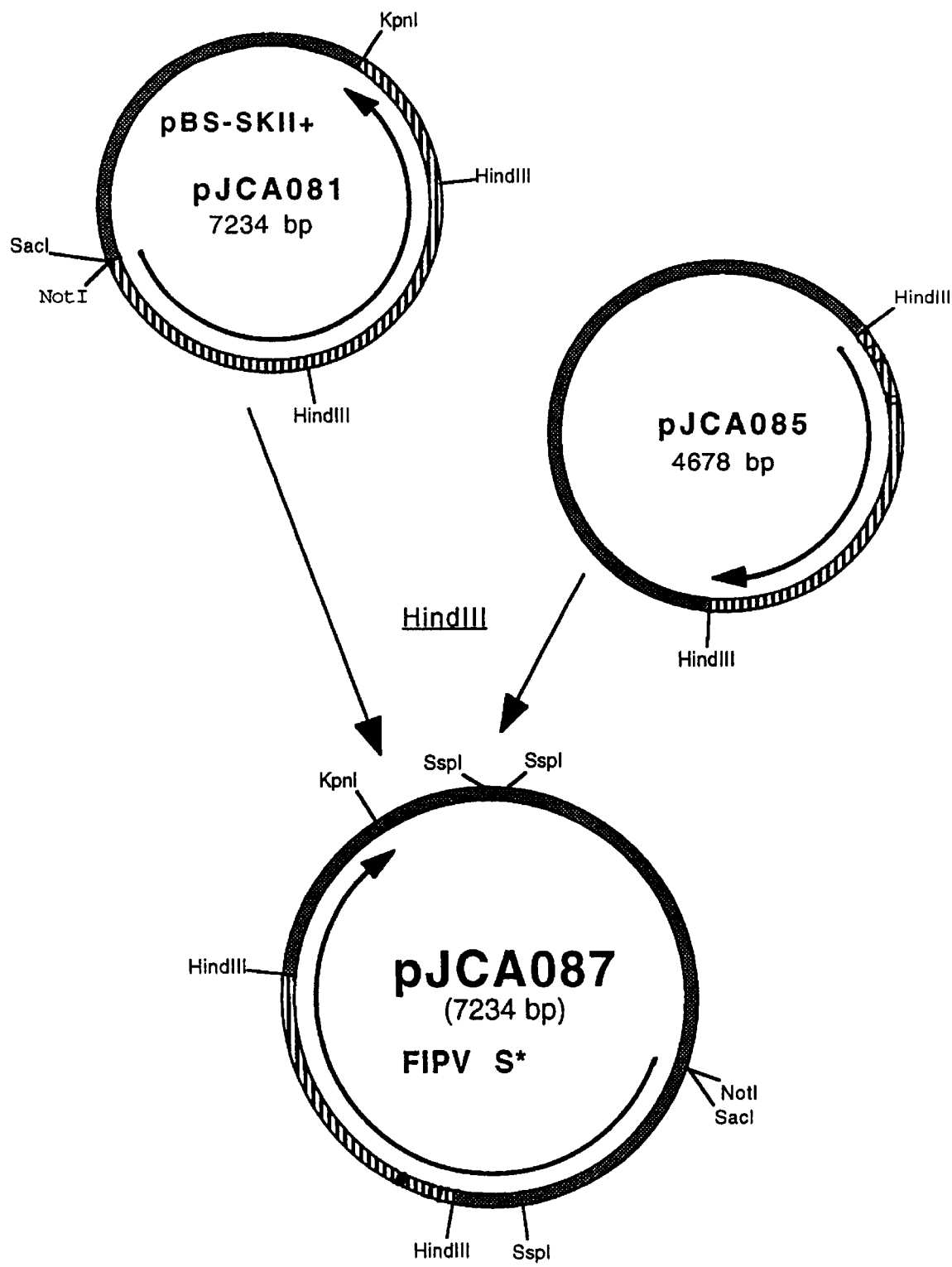
FIG. 8: Mutagenesis of the A1+A2 sites of the FIPV S gene (=FIPV S*) (plasmid pJCA087)
Figure 9:
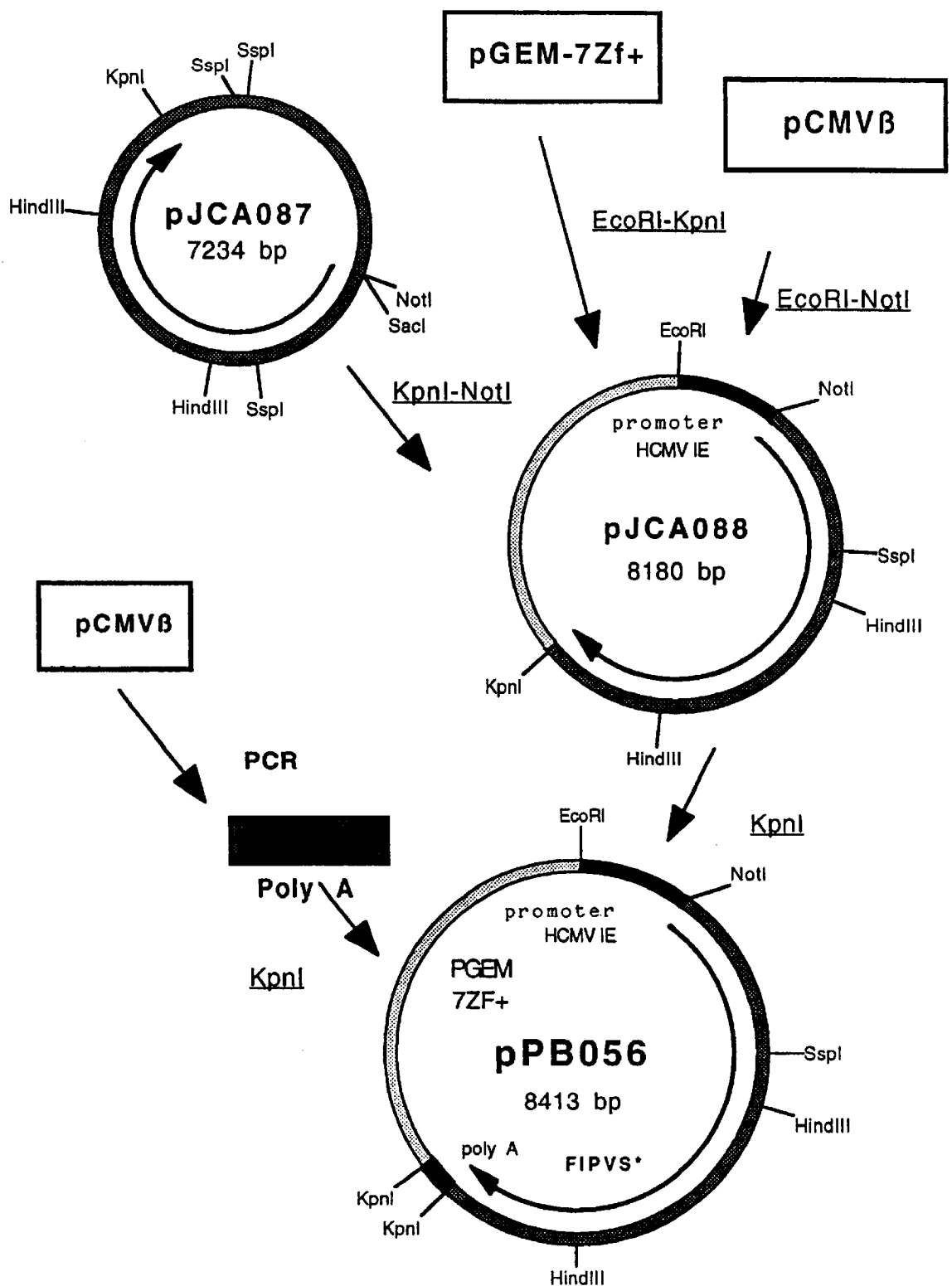
FIG. 9: Construction of the expression cassette for the modified FIPV S* gene (mutations in the A1 and A2 sites) (plasmid pPB056)
Figure 10:
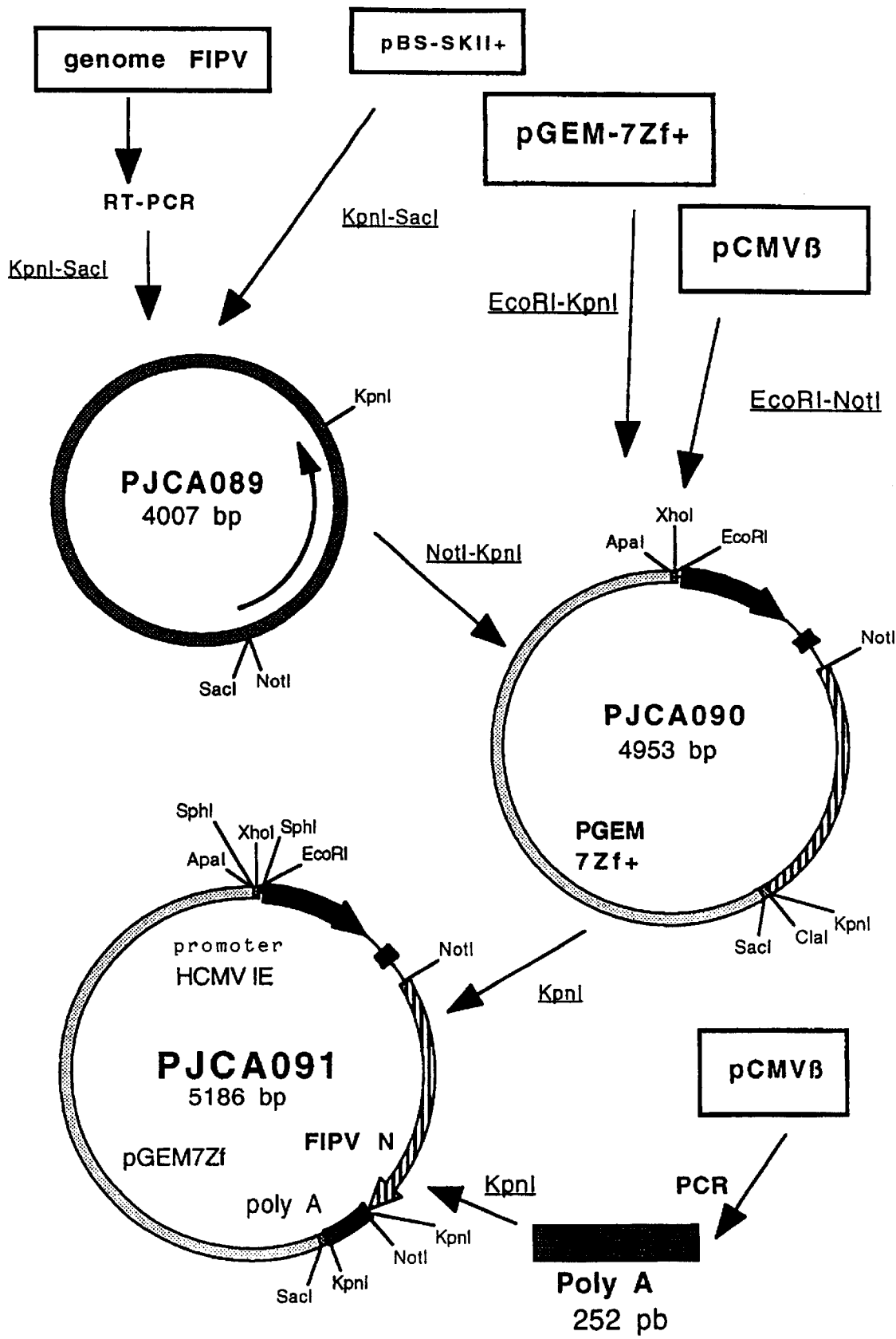
FIG. 10: Construction of the expression cassette for the FIPV N gene (plasmid pJCA091)
Figure 11:
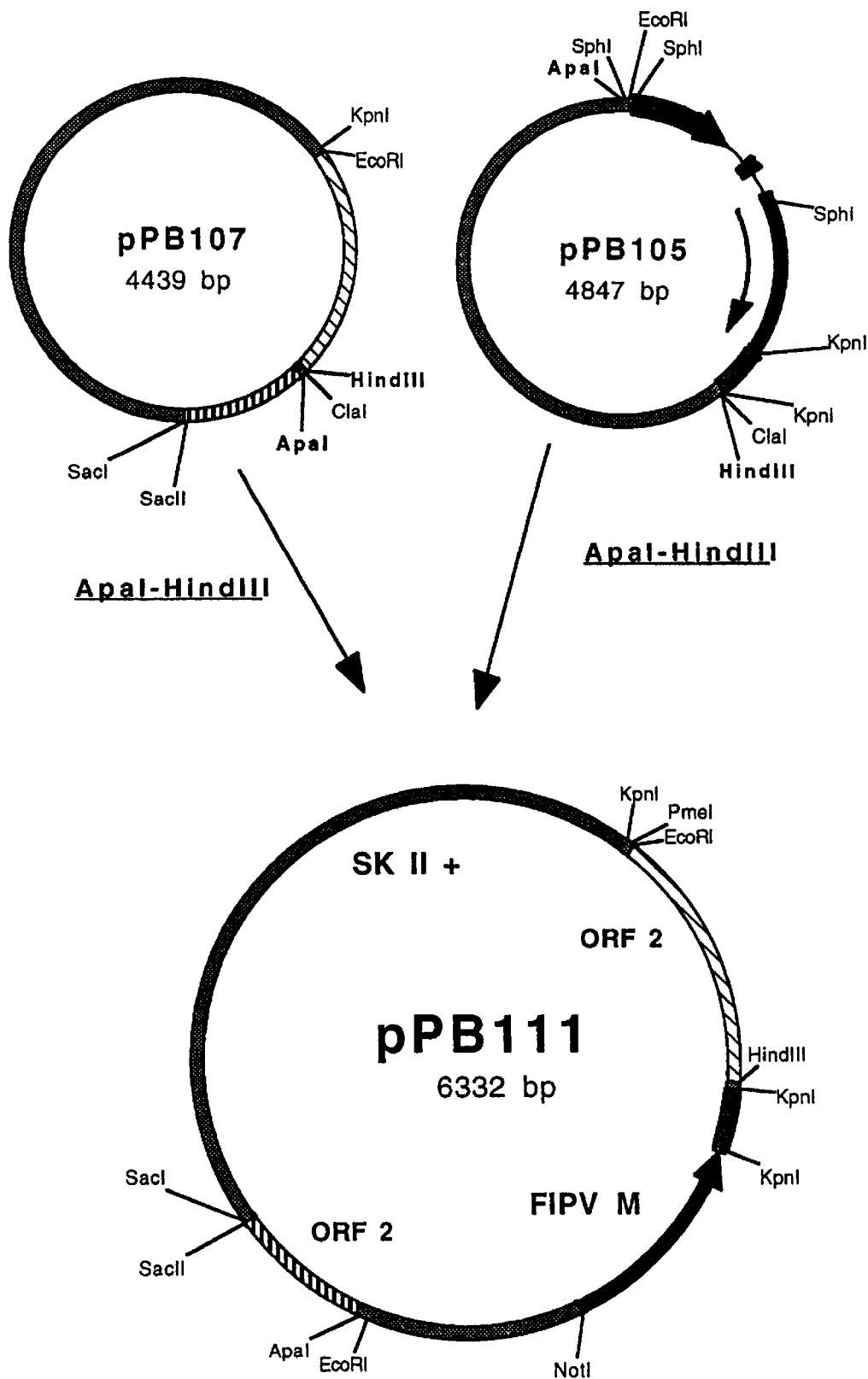
FIG. 11: Construction of the donor plasmid for the insertion of the FIPV M gene expression cassette into the FHV-1 ORF2 site (pPB111)
Figure 12:
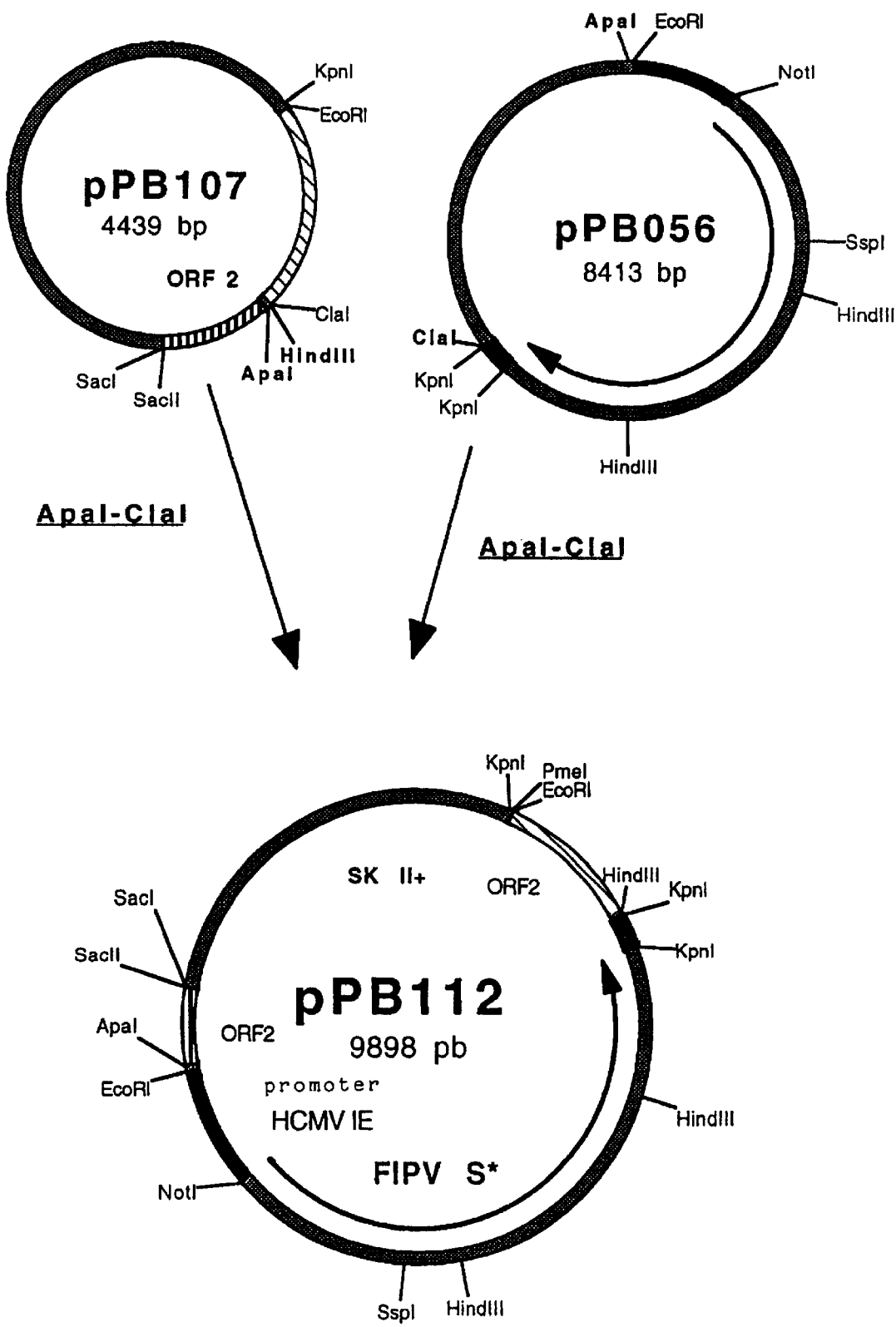
FIG. 12: Construction of the donor plasmid for the insertion of the FIPV S* gene expression cassette into the FHV-1 ORF2 site (pPB112)
Figure 13:
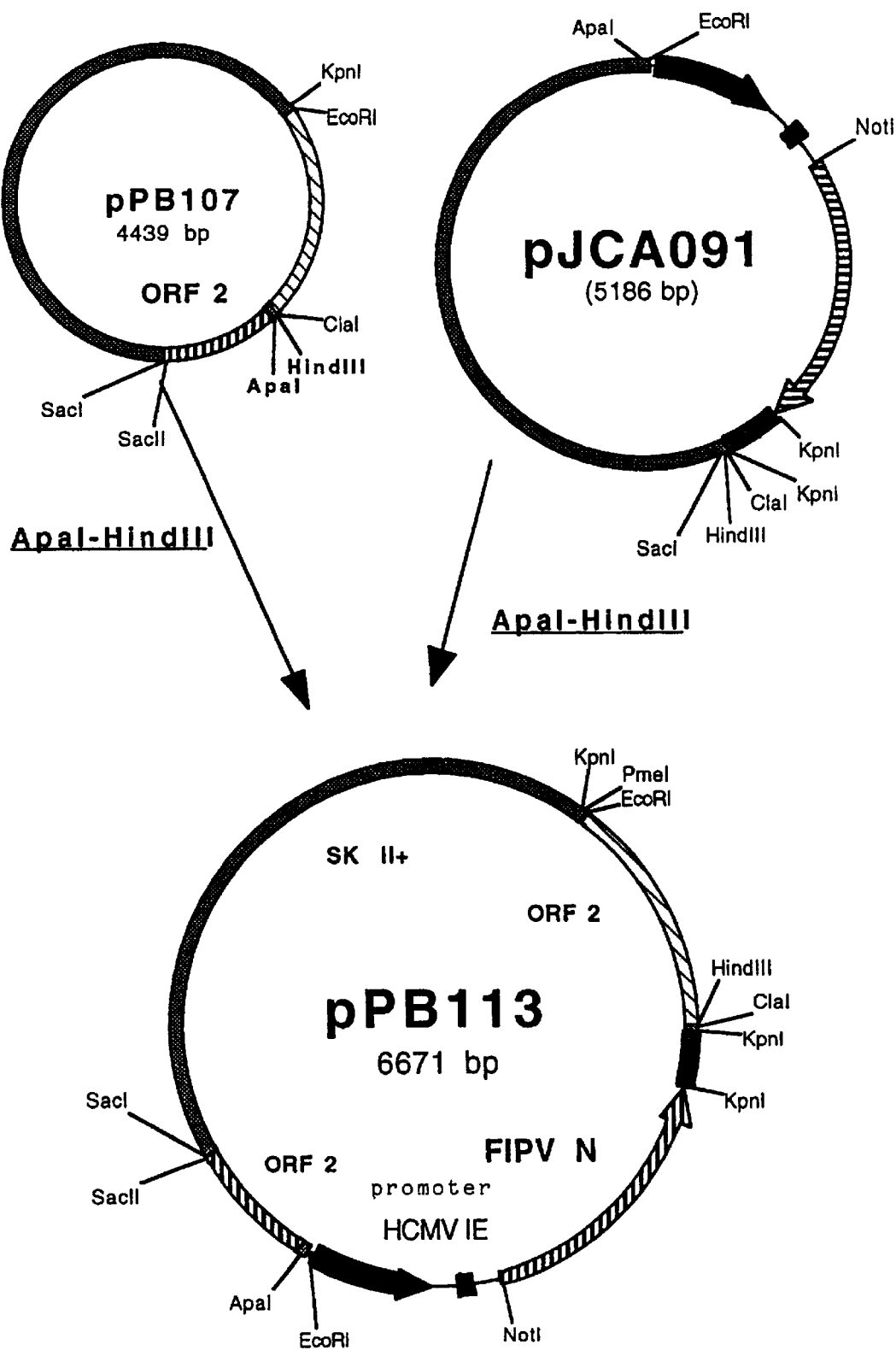
FIG. 13: Construction of the donor plasmid for the insertion of the FIPV N gene expression cassette into the FHV-1 ORF2 site (pPB113)
Figure 14:
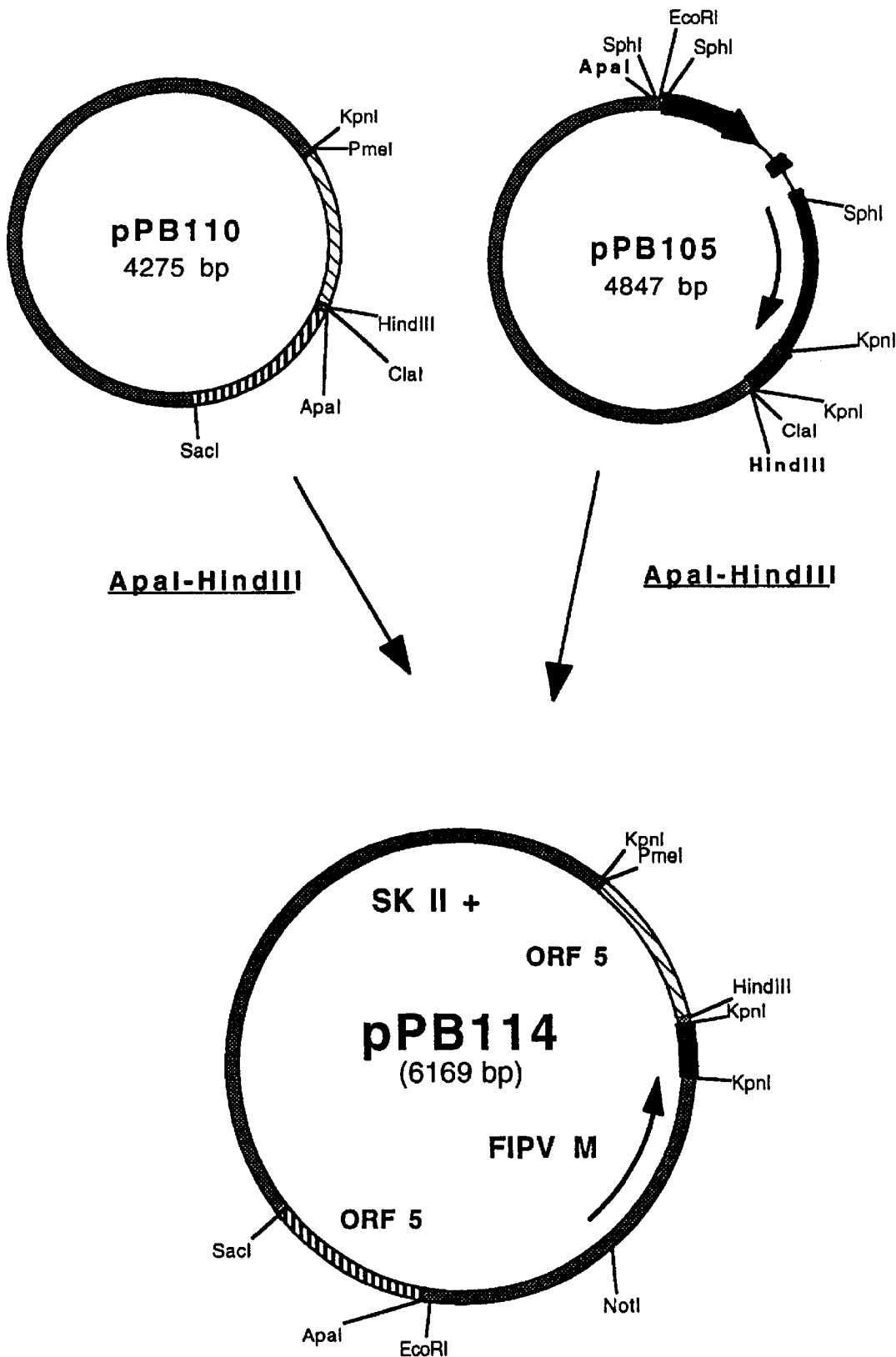
FIG. 14: Construction of the donor plasmid for the insertion of the FIPV M gene expression cassette into the FHV-1 ORF5 site (pPB114)
Figure 15:
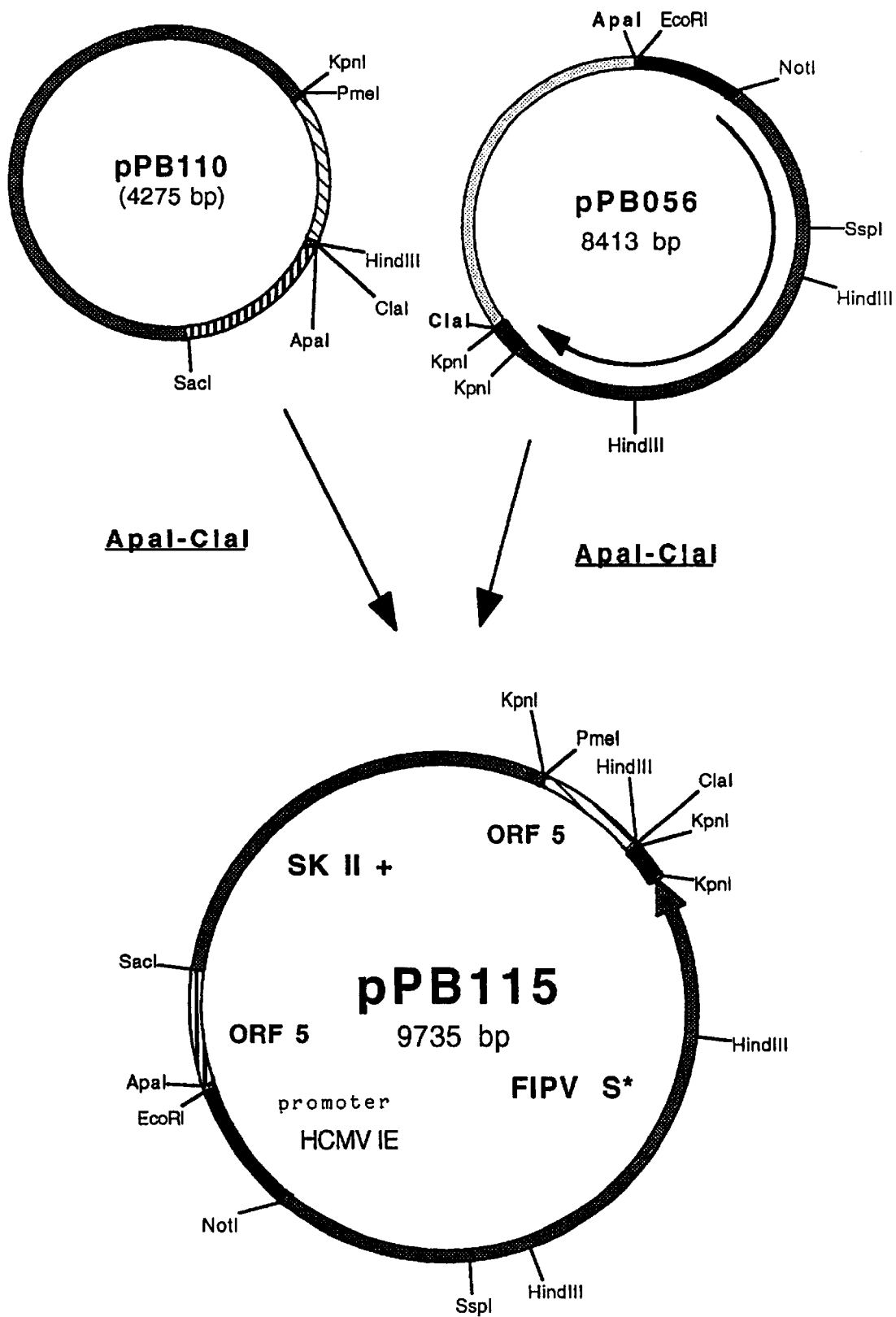
FIG. 15: Construction of the donor plasmid for the insertion of the FIPV S* gene expression cassette into the FHV-1 ORF5 site (pPB115)
Figure 16:
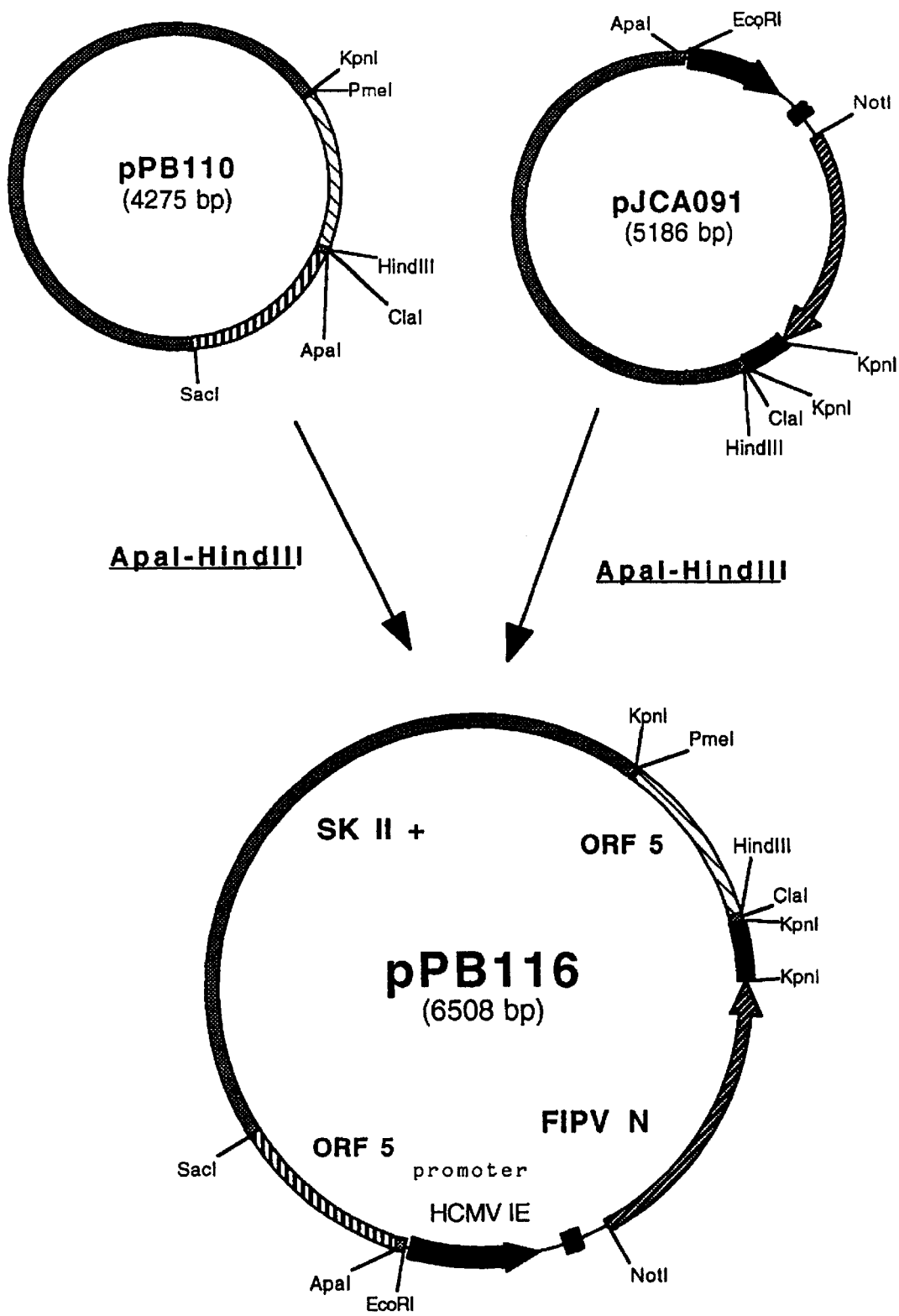
FIG. 16: Construction of the donor plasmid for the insertion of the FIPV N gene expression cassette into the FHV-1 ORF5 site (pPB116)

The sequence listing SEQ ID for the constructs in the ORF2 and ORF5 sites

SEQ ID No. 1 Complete sequence of the FHV-1 ORF1-->ORF8 region represented in FIG. 1
SEQ ID No. 2 Partial amino acid sequence ORF FHV-1 ORF1 of FIG. 1
SEQ ID No. 3 Amino acid sequence ORF FHV-1 ORF2 of FIG. 1
SEQ ID No. 4 Amino acid sequence ORF FHV-1 ORF3 of FIG. 1
SEQ ID No. 5 Amino acid sequence ORF FHV-1 ORF4 of FIG. 1
SEQ ID No. 6 Amino acid sequence ORF FHV-1 ORF5 of FIG. 1
SEQ ID No. 7 Amino acid sequence ORF FHV-1 ORF6 of FIG. 1
SEQ ID No. 8 Amino acid sequence ORF FHV-1 ORF7 of FIG. 1
SEQ ID No. 9 Partial amino acid sequence ORF FHV-1 ORF8 of FIG. 1
SEQ ID No. 10 Oligonucleotide JCA054
SEQ ID No. 11 Oligonucleotide JCA055
SEQ ID No. 12 Oligonucleotide PB080
SEQ ID No. 13 Oligonucleotide PB081
SEQ ID No. 14 Oligonucleotide PB082
SEQ ID No. 15 Oligonucleotide PB083
SEQ ID No. 16 Oligonucleotide PB084
SEQ ID No. 17 Oligonucleotide PB085
SEQ ID No. 18 Oligonucleotide JCA056
SEQ ID No. 19 Oligonucleotide JCA057
SEQ ID No. 20 Oligonucleotide PB088
SEQ ID No. 21 Oligonucleotide PB089
SEQ ID No. 22 Oligonucleotide JCA058
SEQ ID No. 23 Oligonucleotide JCA059
SEQ ID No. 24 Oligonucleotide JCA060
SEQ ID No. 25 Oligonucleotide JCA061
SEQ ID No. 26 Oligonucleotide JCA062
SEQ ID No. 27 Oligonucleotide JCA063
SEQ ID No. 28 Oligonucleotide JCA064
SEQ ID No. 29 Oligonucleotide JCA065
SEQ ID No. 30 Oligonucleotide JCA066
SEQ ID No. 31 Oligonucleotide JCA067
SEQ ID No. 32 Oligonucleotide JCA068
SEQ ID No. 33 Oligonucleotide JCA069

EXAMPLES

All the constructions of plasmids were carried out using the standard molecular biology techniques described by Sambrook J. et al. (*Molecular Cloning: A Laboratory Manual*. 2nd Edition. Cold Spring Harbor Laboratory. Cold Harbor. New York. 1989). All the restriction fragments used for the present invention were isolated using the "Geneclean" kit (BIO101 Inc. La Jolla, Calif.).

The virus used as parental virus is the CO strain of the feline herpesvirus type 1 (FHV-1). This virus was isolated from renal cells from a newborn kitten whose mother had infectious rhinotracheitis (C. Benoit Jeannin, Doctorat de 3ème cycle thesis, University of Lyon, 1983). The conditions for culturing this virus have already been described (Fargeaud D. et al. Arch. Virol. 1984. 80. 69–82). Briefly, CRFK cells (Crandell Rees Feline Kidney cells) cultured in Eagle's minimum essential minimum (MEM medium) are inoculated with the FHV-1 CO strain using a multiplicity of infection of 1. The infected cells are then incubated at 37° C. for about 36 hours, until a complete cytopathic effect appears.

Example 1

Extraction of the DNA from the Feline Herpesvirus Type 1

After culturing, the supernatant and the lysed cells are harvested and the whole viral suspension is centrifuged at 1000 g for 10 minutes at +4° C. in order to remove the cellular debris. The viral particles are then harvested by ultracentrifugation at 400,000 g for 1 hour at +4° C. The pellet is taken up in a minimum volume of buffer (10 mM Tris, 1 mM EDTA). This concentrated viral suspension is treated with proteinase K (100 µg/ml final) in the presence of sodium dodecyl sulphate (SDS) (0.5% final) for 2 hours at 37° C. The viral DNA is then extracted with a phenol/chloroform mixture and then precipitated with 2 volumes of absolute ethanol. After leaving overnight at −20° C., the DNA is centrifuged at 10,000 g for 15 minutes at +4° C. The DNA pellet is dried and then taken up in a minimum volume of sterile ultra-pure water.

Example 2

Isolation of the Genomic RNA from the FIPV 79-1146 Strain and Cloning of the Complementary DNA The FIPV 79-1146 strain was cultured on CRFK cells in DMEM medium (Gibco). The genomic viral RNA was isolated using the guanidium thiocyanate/phenol/chloroform extraction technique (Chomczynski P. and Sacchi N., Anal. Biochem. 1987. 162. 156–159). Specific oligonucleotides (comprising, at their 5' ends, restriction sites to facilitate the cloning of the amplified fragments) were synthesized such that they completely cover the coding regions of the genes which should be amplified (M, S and N respectively). The reverse transcription (RT) reaction and the polymerase chain reaction (PCR) were carried out according to standard techniques (Sambrook J. et al. 1989). Each RT-PCR reaction was performed with a pair of specific amplimers and by taking, as template, the viral genomic RNA extracted. The amplified complementary DNA was extracted with phenol/chloroform/isoamyl alcohol (25:24:1) before being digested with the restriction enzymes.

Example 3

Cloning and Characterization of the FHV-1 ORF1–ORF7 Region (EcoRI D and EcoRI F Fragments)

The genomic DNA purified from the CO strain of the FHV-1 virus was digested with EcoRI and the D (about 9200 bp) and F (7600 bp) fragments were cloned into the vector pBlueScript SKII+ in order to give the plasmids pFHVEcoRID and pFHVEcoRIF respectively. The plasmid pFHVEcoRID was digested with EcoRI and PstI and the EcoRI-PstI fragment of 979 bp was isolated and ligated with the vector pBS-SKII+, previously digested with EcoRI and PstI to give the plasmid pPB050. The plasmid pFHVEcoRID was digested with PstI and the 2388 bp PstI-PstI fragment was isolated and ligated with the vector pBS-SKII+, previously digested with PstI to give the plasmid pPB051. The inserts contained in the plasmids pFHVEcoRIF, pPB050 and pPB051 were completely sequenced on both strands to give the sequence of FIG. 1 (SEQ ID No. 1).

Several open reading frames of more than 65 amino acids in size were identified on this sequence (FIG. 1).

The first reading frame (ORF1) (positions 1–1587) is incomplete and encodes a truncated protein of 529 amino acids (SEQ ID No. 2).

The second reading frame (ORF2) (positions 1655–2596) encodes a polypeptide of 314 amino acids (SEQ ID No. 3).

The third reading frame (ORF3) (positions 2733–4094) is situated on the complementary strand and encodes a polypeptide of 454 amino acids (SEQ ID No. 4).

The fourth reading frame (ORF4) (positions 4476–5660) encodes a polypeptide of 395 amino acids (SEQ ID No. 5).

The fifth reading frame (ORF5) (positions 5869–7113) encodes a polypeptide of 415 amino acids (SEQ ID No. 6).

The sixth reading frame (ORF6) (positions 7449–8900) encodes a polypeptide of 484 amino acids (SEQ ID No. 7).

The seventh reading frame identified on the sequence of FIG. 1 (ORF7) (positions 9153–9731) encodes a protein of 193 amino acids (SEQ ID No. 8).

The eighth and last reading frame identified on the sequence of FIG. 1 (ORF8) (positions 9908–10803) is incomplete. It is situated on the complementary strand and encodes a truncated protein of 298 amino acids (SEQ ID No. 9).

The different open reading frames are assembled in the table below: (Table 1)

| Open reading frame | Beginning–End (positions in FIG. 1) | Size in amino acids |
| --- | --- | --- |
| ORF 1 | 1–1587 | 529 aa |
| ORF 2 | 1655–2596 | 314 aa |
| ORF 3 | 4094–2733 | 454 aa |
| ORF 4 | 4476–5600 | 395 aa |
| ORF 5 | 5869–7113 | 415 aa |
| ORF 6 | 7449–8900 | 484 aa |
| ORF 7 | 9153–9731 | 193 aa |
| ORF 8 | 10803–9908 | 298 aa |

It is thought that the open reading frame FHV ORF2 newly characterized is homologous to the HSV-1 UL40 (RR2) gene.

Example 4

Construction of the Donor Plasmid for the FHV-1 ORF2 Site (pPB107) (FIG. No. 2)

The plasmid pFHVEcoRID was digested with EcoRI and SacII in order to isolate the EcoRI-SacII fragment of 1509 bp. A KpnI-EcoRI adaptor containing the PmeI site was obtained by hybridization of the following 2 synthetic oligonucleotides:
JCA054 (24 mer) (SEQ ID No. 10):
  5' CTTGCCGGGGTTTAAACCGGTTCG 3'
and JCA055 (32 mer) (SEQ ID No. 11):
  5' AATTCGAACCGGTTTAAACCCCGGCAAGGTAC 3'

The EcoRI-SacII fragment and the double-stranded oligonucleotide were ligated into the vector pBS-SKII+, previously digested with KpnI and SacII, to give the plasmid pPB106 (4407 bp). A double-stranded synthetic oligonucleotide comprising the cloning sites HindIII, ClaI and ApaI was obtained by hybridization of the following 2 oligonucleotides:
PB080 (32 mer) (SEQ ID No. 12):
  5' TGCAAAGCTTATCGATCCCGGGGCCCGGTGCA 3'
and PB081 (32 mer) (SEQ ID No. 13):
  5'CCGGGCCCCGGGATCGATAAGCTTTGCATGCA 3'

The oligonucleotide thus obtained was ligated with the plasmid pPB106, previously digested with PstI (unique site on pPB106) and treated with alkaline phosphatase, to give the plasmid pPB107 (4439 bp) (FIG. No. 2). This plasmid contains the 5' (SacII-PstI 530 bp) and 3' (PstI-EcoRI 979 bp) flanking arms of the FHV-1 ORF2 site as well as a multiple cloning site allowing the insertion of an expression cassette.

Example 5

Construction of the Donor Placid for the FHV-1 ORF5 Site (pPB110) (FIG. No. 3)

The plasmid pFHVEcoRIF (see Example 3) was digested with SacI and SmaI in order to isolate the SacI-SmaI fragment of 1367 bp. A SalI-KpnI adaptor containing the PmeI site was obtained by hybridization of the following 2 oligonucleotides:
PB082 (21 mer) (SEQ ID No. 14):
  5' GGGGGCCGTTTAAACCGGTAC 3'
PB083 (17 mer) (SEQ ID No. 15);
  5' CGGTTTAAACGGCCCCC 3'

The double-stranded oligonucleotide thus obtained and the 1367 bp SacI-SmaI fragment were ligated with the plasmid pBS-SKII+, previously digested with KpnI and SacI, to give the plasmid pPB109 (4247 bp). A multiple cloning site was obtained by hybridization of the following 2 synthetic oligonucleotides:
PB084 (28 mer) (SEQ ID No. 16):
  5' TCGAGAAAGCTTATCGATCCCGGGCCCG 3'
PB085 (28 mer) (SEQ ID No. 17):
  5' TCGACGGGCCCGGGATCGATAAGCTTTC 3'

The double-stranded oligonucleotide thus obtained was ligated with the plasmid pPB109, previously digested with SalI and treated with alkaline phosphatase, to give the plasmid pPB110 (4275 bp) (FIG. No. 3).

This plasmid contains the 5' (SacI-SalI 699 bp) and 3' (SalI-SmaI 668 bp) flanking arms of the FHV-1 ORF5 site as well as a multiple cloning site allowing the insertion of an expression cassette.

Example 6

Construction of the Expression Cassette for the FIPV M Gene (FIG. No. 4)

An RT-PCR reaction was carried out with the genomic RNA from the FIPV 79-1146 strain and with the following oligonucleotides:

JCA056 (40 mer) (SEQ ID No. 18)

5' TTTGAGCTCGCGGCCGCATGAAG-TAATTTTGCTAATACTC 3'

JC057 (27 mer) (SEQ ID No. 19)

5' TTTGGTACCGTTTAGTTACACCATATG 3' in order to isolate precisely the gene encoding the membrane glycoprotein (FIPV M) in the form of a SacI-KpnI cassette. After purification the RT-PCR product of 823 bp was digested with KpnI and SacI in order to isolate a KpnI-SacI fragment of 813 bp. This fragment was ligated with the vector pBS-SKII+, previously digested with KpnI and SacI, to give the vector pJCA080 (3668 bp). The sequence of the M gene was checked by sequencing and was found to be identical to that previously published (Vennema H. et al. Virology. 1991. 181. 327–335), which sequence is incorporated into the present application by reference.

The plasmid pCMVβ (CLONTECH) was digested with EcoRI and NotI in order to isolate the EcoRI-NotI fragment of 819 bp containing the promoter region of the human cytomegalovirus immediate early gene (fragment A). The plasmid pJCA080 was digested with KpnI and NotI in order to isolate the NotI-KpnI fragment (FIPV M gene) of 804 bp (fragment B). The A and B fragments were then ligated with the vector pGEM-7Zf+ (Promega), previously digested with EcoRI and KpnI, to give the plasmid pPB104 (4614 bp).

A PCR reaction was carried out with the following oligonucleotides:

PB088 (30 mer) (SEQ ID No. 20)

5' TTGGGTACCGCCTCGACTCTAGGCGGCCGC 3'

PB089 (32 mer) (SEQ ID No. 21)

5' TTGGGTACCGGATCCGAAAAAACCTCCCACAC 3' and the template pCMVβ in order to produce a 252 bp fragment containing the polyadenylation signal of the SV40 virus early gene. This fragment was digested with KpnI in order to isolate the KpnI-KpnI fragment of 233 bp (fragment B). This fragment was then ligated with the plasmid pPB104, previously digested with KpnI and treated with alkaline phosphatase, to give the plasmid pPB105 (4847 bp) (FIG. No. 4). This plasmid contains an expression cassette HCMV-IE promoter—FIPV M gene—SV40 polyA which can be mobilized by ApaI-ClaI or ApaI-HindIII digestion.

Example 7

Construction of the Expression Cassette for the FIPV S Gene (FIG. No. 5)

An RT-PCR reaction was carried out with the genomic RNA from the FIPV 79-1146 strain and with the following oligonucleotides:

JCA058 (39 mer) (SEQ ID No. 22)

5' TTTGAGCTCGCGGCCGCATGATTGT-GCTCGTAACTTGCC 3'

JCA059 (38 mer) (SEQ ID No. 23)

5' TTTGGTACCGTTTAGTGGACATG-CACTTTTTCAATTGG 3' in order to isolate precisely the gene encoding the spike glycoprotein or also called hereinafter "S" (FIPV S). After purification, the RT-PCR product of 4387 bp was digested with KpnI and SacI in order to isolate a KpnI-SacI fragment of 4375 bp. This fragment was ligated with the vector pBS-SKII+, previously digested with KpnI and SacI, to give the vector JCA081 (7234 bp). The sequence of the S gene was checked by sequencing and was found to be identical to that previously published (de Groot R. et al. J. Gen. Virol. 1987. 68. 2639–2646), which sequence is incorporated into the present application by reference.

The plasmid pCMVβ was digested with EcoRI and NotI in order to isolate the EcoRI-NotI fragment of 819 bp containing the promoter region of the human cytomegalovirus immediate early gene (fragment A). The plasmid JCA081 was digested with KpnI and NotI in order to isolate the NotI-KpnI fragment (FIPV S gene) of 4372 bp (fragment B). The A and B fragments were then ligated with the vector pGEM-7Zf+, previously digested with EcoRI and KpnI, to give the plasmid pJCA082 (8180 bp).

A PCR reaction was carried out with the following oligonucleotides: PB088 (SEQ ID No. 20) and PB089 (SEQ ID No. 21) (see Example 6) and the template pCMV in order to produce a 252 bp fragment containing the polyadenylation signal of the SV40 virus early gene. This fragment was digested with KpnI in order to isolate the KpnI-KpnI fragment of 233 bp (fragment B).

This fragment was ligated with the plasmid pJCA082, previously digested with KpnI and treated with alkaline phosphatase, to give the plasmid pPB055 (8413 bp) (FIG. No. 5). This plasmid contains an expression cassette HCMV-IE promoter—FIPV S gene—SV40 polyA which can be mobilized by ApaI-ClaI digestion.

Example 8

Construction of the Modified Spike Gene (FIPV S*)

The sequence of the FIPV S gene was subjected to mutagenesis so as to modify the regions responsible for the induction of facilitating antibodies, without changing the functions of the S glycoprotein. This modification has already been described in Patent Application FR-94 10379 (publication No. 2,724,385, incorporated herein by reference), and was carried out in the following manner:

8.1.: Mutagenesis of the A1 Site (FIG. No. 6)

The HindIII-HindIII FIPV S gene central fragment of 1723 bp (nucleotides 1696 to 3418) was cloned into the vector pBS-SKII+, previously digested with HindIII and treated with alkaline phosphatase, to give the plasmid pJCA083 (4678 bp). The A1 site is situated on the HindIII-SspI subfragment (positions 1696 to 1845) of this fragment.

The A1 site was subjected to mutagenesis by PCR using the following strategy:

The following nucleotides were synthesized:

JCA060 (95 mer) (SEQ ID No. 24)

5' ATGAAGCTTAGTGGTTATGGTCAAC-CCATAGCCTCGACACTAAGTAACATCA-CACTACCAATGCAGGATAACAATACTGT-TGTGTACTGTATTCG 3'

JCA061 (88 mer) (SEQ ID No. 25)

5' AAAAATATTGTACCATAAAGAACTTTTG-CAAGTGGAATGAACATAAACTGAGAAT-TGGTTAGAACGAATACAGTACACAACAG-TATTG 3'

JCA062 (20 mer) (SEQ ID No. 26)

5' ATGAAGCTTAGTGGTTATGG 3'

JCA063 (20 mer) (SEQ ID No. 27)

5' AAAAATATTGTACCATAAAG 3'

The oligonucleotides JCA060 and JCA061 were hybridized with each other by means of their common complementary sequence of 23 base pairs. The hybrid thus obtained was used, after extension of its 3' ends, as template for a PCR reaction using the oligonucleotides JCA062 and JCA063. This PCR amplification reaction made it possible to obtain a 159 bp fragment. This fragment was digested with HindIII and SspI in order to produce a HindIII-SspI fragment of 149 bp (fragment A). This fragment contains the A1 site modified at two positions (Val instead of Asp at position 568 and Tyr instead of Asp at position 591). The plasmid pJCA083 was digested with HindIII and partially digested with SspI in order to isolate the SspI-HindIII fragment of 1569 bp (fragment B) by Geneclean (BIO101 Inc., La Jolla. Calif.).

The vector pBS-SKII+ was digested with HindIII and treated with alkaline phosphatase in order to produce the C fragment (2960 bp).

The A, B and C fragments were then ligated together in order to produce the plasmid pJCA084 (4678 bp) (FIG. No. 6). This plasmid contains the HindIII-HindIII fragment of the FIPV S gene modified for two amino acids of the A1 site. The FIPV S gene can then be reconstituted by replacing the natural HindIII-HindIII fragment (positions 1696 to 3418) with the HindIII-HindIII fragment contained in the plasmid pJCA084. The complete FIPV S gene modified at the A1 site can then be used for constructions of expression plasmids or of recombinant viruses.

8.2.: Mutagenesis of the A2 Site (FIG. No. 7)

The following oligonucleotides were synthesized:

JCA064 (20 mer) (SEQ ID No. 28)

5 GGACAATATTTTTAATCAAG 3'

JCA065 (36 mer) (SEQ ID No. 29)

5' TTTAACAACCTGCTCATTGGTTCCTG-TACGTGCAGC 3'

JCA066 (36 mer) (SEQ ID No. 30)

5' AAGTTTTATGTTGCTGCACGTACAG-GAACCAATGAG 3'

JCA067 (20 mer) (SEQ ID No. 31)

5' ATCACTAACATTTTTAAAGC 3'

A PCR reaction (PCR A) was carried out with the oligonucleotides JCA064 and JCA065 and with the plasmid pJCA083 as template in order to synthesize a PCR fragment of 199 bp (fragment A).

A PCR reaction (PCR B) was carried out with the oligonucleotides JCA066 and JCA067 and with the plasmid pJCA083 as template in order to give a PCR fragment of 273 bp (fragment B).

The PCR A and B fragments were hybridized with each other by means of their complementary region of 46 bp and the product of this hybridization, after extension of the 3' ends, was amplified by a PCR reaction (PCR C) with the oligonucleotides JCA064 and JCA067 in order to give a PCR fragment of 424 bp. This PCR fragment was digested with SspI and DraI in order to give the SspI-DraI restriction fragment of 402 bp (fragment C).

The plasmid pJCA083 was digested with HindIII and SspI in order to isolate the HindIII-SspI fragment of 149 bp (fragment D).

The plasmid pJCA083 was digested with HindIII and DraI in order to isolate the DraI-HindIII restriction fragment of 1170 bp (fragment E).

The vector pBS-SKII+ was digested with HindIII and treated with alkaline phosphatase to give the fragment F (2960 bp).

The C, D, E and F fragments were then ligated together in order to give the plasmid pJCA085 (4678 bp) (FIG. No. 7). The HindIII-HindIII central fragment of 1723 bp of the FIPV S gene contained in pJCA085 has an A2 site modified at the level of 3 amino acids (Tyr instead of Asp at position 643, Gly instead of Arg at position 649, and Lys instead of Arg at position 656).

The FIPV S gene may then be reconstituted by replacing the natural HindIII-HindIII fragment (positions 1696 to 3418) with the HindIII-HindIII fragment contained in the plasmid pJCA085. The complete FIPV S gene modified at the A2 site may then be used for constructions of expression plasmids or of recombinant viruses.

8.3.: Mutagenesis of the A1 and A2 Sites (FIG. No. 8)

Fragments A (Example 8.1), C and E (Example 8.2) were ligated with the vector pBS-SKII+, previously digested with HindIII and treated with alkaline phosphatase, to give the plasmid pJCA085. The HindIII-HindIII central fragment of 1723 bp of the FIPV S gene contained in pJCA085 exhibits 2 amino acid changes at the level of the A1 site (see Example 8.1) and 3 amino acid changes at the level of the A2 site (see Example 8.2).

The plasmid pJCA081 (Example 7) was digested with HindIII in order to isolate the HindIII-HindIII fragment of 5511 bp (fragment A). The plasmid PJCA085 was digested with HindIII in order to isolate the HindIII-HindIII fragment of 1723 bp (exhibiting 5 amino acid changes relative to the sequence of the strain FIPV 79-1146) (fragment B). The A and B fragments were ligated together in order to give the plasmid pJCA087 (7234 bp) (FIG. No. 8). This plasmid contains the FIPV S gene modified at the level of the A1 and A2 sites (=FIPV S* gene).

8.4.: Construction of the Expression Cassette for the FIPV S* Gene (FIG. No. 9)

The plasmid pCMVβ was digested with EcoRI and NotI in order to isolate the EcoRI-NotI fragment of 819 bp containing the promoter region of the human cytomegalovirus immediate early gene (fragment A). The plasmid pJCA087 (Example 8.3) was digested with KpnI and NotI in order to isolate the NotI-KpnI fragment (FIPV S gene) of 4372 bp (fragment B). The A and B fragments were then ligated with the vector pGEM-7Zf+, previously digested with EcoRI and KpnI, to give the plasmid pJCA088 (8180 bp).

A PCR reaction was carried out with the following oligonucleotides: PB088 (SEQ ID No. 20) and PB089 (SEQ ID No. 21) (see Example 6) and the template pCMVβ in order to produce a 252 bp fragment containing the polyadenylation signal of the SV40 virus early gene. This fragment was digested with KpnI in order to isolate the KpnI-KpnI fragment of 233 bp (fragment B).

This fragment was ligated with the plasmid pJCA088, previously digested with KpnI and treated with alkaline phosphatase, to give the plasmid pPB056 (8413 bp) (FIG. No. 9). This plasmid contains an expression cassette HCMV-IE promoter—FIPV S* gene—SV40 polyA which can be mobilized by ApaI-ClaI digestion.

Example 9

Construction of the Expression Cassette for the FIPV N Gene (FIG. No. 10)

An RT-PCR reaction was carried out with the genomic RNA from the strain FIPV 79-1146 and with the following oligonucleotides:

JCA068 (37 mer) (SEQ ID No. 32)

5' TTTGAGCTCGCGGCCGCATGGCCACACAGGGACAACG 3'

JCA069 (33 mer) (SEQ ID No. 33)

5' TTTGGTACCGTTTAGTTCGTAACCTCATCAATC 3' in order to isolate precisely the gene encoding the nucleocapsid protein "N" (FIPV N). After purification, the RT-PCR product of 1161 bp was digested with KpnI and SacI in order to isolate a SacI-KpnI fragment of 1148 bp. This fragment was ligated with the vector pBS-SKII+, previously digested with KpnI and SacI, in order to give the vector pJCA089 (4007 bp). The sequence of the N gene was checked by sequencing and was found to be identical to that previously published (Vennema H. et al. Virology 1991. 181. 327–335), which sequence is incorporated into the present application by reference.

The plasmid pCMVβ (CLONTECH) was digested with EcoRI and NotI in order to isolate the EcoRI-NotI fragment of 891 bp containing the promoter region of the human cytomegalovirus immediate early gene (fragment A). The plasmid pJCA089 was digested with KpnI and NotI in order to isolate the NotI-KpnI fragment (FIPV N gene) of 1137 bp (fragment B). The A and B fragments were ligated with the vector pGEM-7Zf+, previously digested with EcoRI and KpnI, to give the plasmid pJCA090 (4953 bp).

A PCR reaction was carried out with the following oligonucleotides: PB088 (SEQ ID No. 20) and PB089 (SEQ ID No. 21) (Example 6) and the template pCMVβ in order to produce a 252 bp fragment containing the polyadenylation signal of the SV40 virus early gene. This fragment was digested with KpnI in order to isolate the KpnI-KpnI fragment of 233 bp (fragment B). This fragment was then ligated with the plasmid pJCA090, previously digested with KpnI and treated with alkaline phosphatase, to give the plasmid pJCA091 (5186 bp) (FIG. No. 10). This plasmid contains an expression cassette HCMV-IE promoter—FIPV N gene—SV40 polyA which can be mobilized by ApaI-ClaI or ApaI-HindIII digestion.

Example 10

Construction of the Donor Plasmid pPB111 and Isolation of vFHV01 (FIG. No. 11)

The plasmid pPB105 (Example 6, FIG. No. 4) was digested with ApaI and HindIII in order to isolate the ApaI-HindIII fragment of 1925 bp (fragment A). The pPB107 plasmid (Example 4, FIG. No. 2) was digested with ApaI and HindIII in order to isolate the ApaI-HindIII fragment of 4419 bp (fragment B). The A and B fragments were ligated together in order to give the plasmid pPB111 (6332 bp) (FIG. No. 11). This plasmid contains the expression cassette HCMV-IE/FIPV M gene/SV40 polyA in the FHV ORF2 site.

The plasmid pPB111 was linearized by digestion with PmeI, extracted with a phenol-chloroform mixture, precipitated with absolute ethanol and then taken up in sterile water.

CRFK cells, forming a well-established cellular lawn in a Petri dish (Corning 4.5 cm in diameter), were then transfected with the following mixture: 1 μg of linearized plasmid pPB111+5 μg of viral DNA from FHV-1 in 300 μl of MEM medium and 100 μg of LipofectAMINE (Gibco-BRL Cat # 18324-012) diluted in 300 μl of medium (final volume of the mixture 600 μl). These 600 μl were then diluted in 3 ml (final volume) of MEM medium and plated on $3\times10^6$ CRFK cells. The mixture was left in contact with the cells for 5 hours and then removed and replaced with 5 ml of culture medium. The cells were then left in culture for 24 hours at +37° C. After 24 hours to 48 hours of culture, 1 ml of culture supernatant was harvested and several dilutions of this supernatant were used to infect new CRFK cells (cultured in a Corning Petri dish 4.5 cm in diameter) so as to obtain isolated plaques, each dish being infected with 1 ml of a dilution of the initial supernatant. After a contact of 1 hour at 37° C., the infection medium was removed and replaced with 5 ml of MEM medium containing 1% agarose, maintained superfused at 42° C. When the agarose had solidified, the dishes were incubated for 48 hours at 37° C. in a $CO_2$ oven until plaques appeared. The agarose layer was then removed and the viral plaques were transferred onto a sterile nitrocellulose membrane of the same diameter as the Petri dish which served for the culture. This membrane was itself transferred onto another nitrocellulose membrane so as to obtain a reverse "copy" of the first transfer. The plaques transferred onto the latter copy were then hybridized, according to the customary techniques known to a person skilled in the art, with a fragment of the FIPV M gene labelled with digoxigenin (DNA Labelling Kit, Boehringer Mannheim, CAT # 1175033). After hybridization, washes and bringing into contact with the revealing substrate, the nitrocellulose membrane was brought into contact with an autoradiographic film. The positive hybridization images on this membrane indicated which plaques contained recombinant FHV viruses which had inserted the FIPV M cassette. The plaques corresponding to these positive plaques were sterilely cut out from the first nitrocellulose membrane, placed in an Eppendorf tube containing 0.5 ml of MEM medium and sonicated in order to release the virions from the membrane. The medium contained in the Eppendorf tube was then diluted in MEM medium and the dilutions thus obtained served to infect new cultures of CRFK cells. A recombinant virus, containing the cassette HCMV-IE/FIPV M/polyA inserted into the ORF2 site, 100% pure, was thus isolated after 3 purification cycles and was called vFHV01. The homology of the recombination was checked by PCR using oligonucleotides situated on either side of the site of insertion. The absence of rearrangement on the genome of the recombinant virus vFHV01, elsewhere apart from the recombination region, was checked by the Southern blot technique.

Example 11

Construction of the Donor Plasmid pPB112 and Isolation of vFHV02 (FIG. No. 12)

The plasmid pPB056 (Example 8.4, FIG. No. 9) was digested with ApaI and ClaI in order to isolate the ApaI-ClaI fragment of 5466 bp (fragment A). The plasmid pPB107 (Example 4, FIG. No. 2) was digested with ApaI and ClaI in order to isolate the ApaI-ClaI fragment of 4426 bp (fragment B). The A and B fragments were ligated together in order to give the plasmid pPB112 (9898 bp) (FIG. No. 12). This plasmid contains the expression cassette (HCMV-IE/FIPV S* gene/SV40 polyA) in the FHV-1 ORF2 site.

CRFK cells were transfected with a mixture of plasmid pPB112 (linearized with PmeI) and of viral DNA from FHV-1 as described in Example 10. A positive viral plaque for the cassette HCMV-IE/FIPV S* gene was purified as described in Example 10, but using a homologous probe FIPV S*, and amplified in order to give the recombinant virus vFHV02.

Example 12

Construction of the Donor Plasmid pPB113 and Isolation of vFHV03 (FIG. No. 13)

The plasmid pJCA091 (Example 9, FIG. No. 10) was digested with ApaI and HindIII in order to isolate the ApaI-HindIII fragment of 2244 bp (fragment A). The plasmid pPB107 (Example 4, FIG. No. 2) was digested with ApaI and HindIII in order to isolate the ApaI-HindIII fragment of 4419 bp (fragment B). The A and B fragments were ligated together in order to give the plasmid pPB113 (6671 bp) (FIG. No. 13). This plasmid contains the expression cassette (HCMV-IE/FIPV N gene/SV40 polyA) in the FHV-1 ORF2 site.

CRFK cells were transfected with a mixture of plasmid pPB113 (linearized with PmeI) and of viral DNA from FHV-1 as described in Example 10. A positive viral plaque for the cassette HCMV-IE/FIPV N gene was purified as described in Example 10, but using a homologous probe FIPV N, and amplified in order to give the recombinant virus vFHV3.

Example 13

Construction of the Donor Plasmid pPB114 and Isolation of vFHV4 (FIG. No. 14)

The plasmid pPB105 (Example 6, FIG. No. 4) was digested with ApaI and HindIII in order to isolate the ApaI-HindIII fragment of 1925 bp (fragment A). The plasmid pPB110 (Example 5, FIG. No. 3) was digested with ApaI and HindIII in order to isolate the ApaI-HindIII fragment of 4256 bp (fragment B). The A and B fragments were ligated together in order to give the plasmid pPB114 (6169 bp) (FIG. No. 14). This plasmid contains the expression cassette (HCMV-IE/FIPV M gene/SV40 polyA) in the FHV-1 ORF5 site.

CRFK cells were transfected with a mixture of plasmid pPB114 (linearized with PmeI) and of viral DNA from FHV-1 as described in Example 10. A positive viral plaque for the cassette HCMV-IE/FIPV M gene was purified as described in Example 10 and amplified in order to give the recombinant virus vFHV4.

Example 14

Construction of the Donor Plasmid pPB115 and Isolation of vFHV05 (FIG. No. 15)

The plasmid pPB056 (Example 8.4, FIG. No. 9) was digested with ApaI and ClaI in order to isolate the ApaI-ClaI fragment of 5466 bp (fragment A). The plasmid pPB110 (Example 5, FIG. No. 3) was digested with ApaI and ClaI in order to isolate the ApaI-ClaI fragment of 4263 bp (fragment B). The A and B fragments were ligated together in order to give the plasmid pPB115 (9735 bp) (FIG. No. 5). This plasmid contains the expression cassette (HCMV-IE/FIPV S gene/SV40 polyA) in the FHV-1 ORF5 site.

CRFK cells were transfected with a mixture of plasmid pPB115 (linearized with PmeI) and of viral DNA from FHV-1 as described in Example 10. A positive viral plaque for the cassette HCMV-IE/FIPV S* gene was purified as described in Example 10, but using a homologous probe FIPV S*, and amplified in order to give the recombinant virus vFHV05.

Example 15

Construction of the Donor Plasmid pPB116 and Isolation of vFHV06 (FIG. No. 16)

The plasmid pJCA091 (Example 9, FIG. No. 10) was digested with ApaI and HindIII in order to isolate the ApaI-HindIII fragment of 2244 bp (fragment A). The plasmid pPB110 (Example 5, FIG. No. 3) was digested with ApaI and HindIII in order to isolate the ApaI-HindIII fragment of 4256 bp (fragment B). The A and B fragments were ligated together in order to give the plasmid pPB116 (6508 bp). This plasmid contains the expression cassette (HCMV-IE/FIPV N gene/SV40 polyA) in the FHV-1 ORF5 site.

CRFK cells were transfected with a mixture of plasmid pPB116 (linearized with PmeI) and of viral DNA from FHV-1 as described in Example 10. A positive viral plaque for the cassette HCMV-IE/FIPV N gene was purified as described in Example 10, but using a homologous probe FIPV N, and amplified in order to give the recombinant virus vFHV06.

Example 16

Construction of Donor Plasmids for the Insertion of Expression Cassettes into the ORF2 Site of FHV-1

According to the same strategy as that described above for the insertion of expression cassettes (genes placed under the control of the HCMV-IE or MCMV-IE promoters or double promoter MCMV-IE/RNA 1.8 kbp) into the ORF2 site, it is possible to construct recombinant feline herpesviruses expressing at a high level immunogens of the feline calicivirus (FCV), of the feline panleukopenia virus (FPV), of the feline leukaemia virus (FeLV), of the feline immunodeficiency virus (FIV), or of other feline pathogens, or alternatively of feline cytokines.

Example 17

Construction of Donor Plasmids for the Insertion of Expression Cassettes into the ORF5 Site of FHV-1

According to the same strategy as that described above for the insertion of expression cassettes (genes placed under the control of HCMV-IE or MCMV-IE promoters or double promoter MCMV-IE/RNA 1.8 kbp) into the ORF5 site, it is possible to construct recombinant feline herpesviruses expressing at a high level immunogens of the FCV, FPV, FeLV or FIV viruses or of other feline pathogens, or alternatively of feline cytokines.

Example 18

Production of Vaccines

To produce a vaccine, the recombinant viruses obtained according to the invention are cultured on CRFK cells. The recombinant virus is harvested when the cytopathic effect is complete. The lysed cells and the culture supernatant are harvested. After clarification of a cellular lysate in order to remove the cellular debris, the viral solution is titrated. The viral solution is then diluted in a stabilizing solution for freeze-drying, distributed at the rate of one vaccinal dose ($10^2$ CCID$_{50}$ to $10^7$ CCID$_{50}$) per vial, and finally freeze-dried.

What is claimed is:

1. A recombinant feline herpesvirus (FHV) comprising and expressing at least one nucleic acid molecule encoding a polypeptide, wherein the at least one nucleic acid molecule is inserted into the ORF5 and/or ORF2 site of FHV, which in the FHV-1 CO strain, have the nucleotide sequences 5869–7113 and 1665–2596, of SEQ ID NO: 1, respectively.

2. The FIV according to claim 1, wherein the at least one nucleic acid molecule is inserted into the ORF5 and ORF2 sites by simple insertion, or after total or partial deletion of these sites.

3. The FHV according to claim 1, wherein the at least one nucleic acid molecule is inserted into one of the ORF5 and ORF2 sites, and a deletion is carried out in the other site.

4. The FHV according to claim 1, wherein the recombinant FHV includes a strong eukaryotic promoter for expression of the at least one nucleic acid molecule.

5. The FHV according to claim 4, wherein the strong promoter is a CMV immediate early promoter.

6. The FHV according to claim 1, wherein the recombinant FHV comprises at least two nucleic acid molecules inserted into the ORF5 or ORF2 site under the control of different eukaryotic promoters.

7. The FHV according to claim 6, wherein the eukaryotic promoters are CMV immediate-early promoters of different animal origins.

8. The FHV according to claim 6, wherein the recombinant FHV comprises: a first nucleic acid molecule operably linked to a first promoter wherein the first promoter is the CMV immediate-early promoter; and a second nucleic acid molecule operably linked to a second promoter, and, the 5' end of the promoters are adjacent.

9. The FHV according to claim 1, wherein the recombinant FHV comprises a nucleic acid molecule encoding an antigenic polypeptide.

10. The FHV according to claim 9, wherein the nucleic acid molecule encodes an antigenic polypeptide of a feline pathogenic agent.

11. The FHV according to claim 10, wherein the nucleic acid molecule encodes an antigen selected from the group consisting of: the antigens of the feline infectious peritonitis virus, the antigens of feline leukemia virus, the antigens of feline immunodeficiency virus, the antigens of feline infectious panleukopenia virus and the antigens of feline calicivirus.

12. The FHV according to claim 10, wherein the nucleic acid molecule encodes a polypeptide from feline infectious peritonitis virus selected from the group consisting of M, modified S and N.

13. The FHV according to claim 10, wherein the at least one nucleic acid molecule comprises a nucleic acid molecule encoding an antigen selected from the group consisting of the env antigen of feline leukemia virus, the gag antigen of feline leukemia virus, the pol antigen of the feline leukemia virus, the env antigen of feline immunodeficiency virus, the gag antigen of feline immunodeficiency virus, the pol antigen of the feline immunodeficiency virus, the VP2 capsid antigen of the feline infectious panleukopenia virus, the capsid antigen of feline calicivirus, the M antigen of feline infectious peritonitis virus, the modified S antigen of feline infectious peritonitis virus, the N antigen of feline infectious peritonitis virus, the 7b antigen of feline infectious peritonitis virus, and the polymerase antigen of the feline infectious peritonitis virus.

14. The FHV according to claim 6, wherein the recombinant FHV comprises: a first nucleic acid molecule under the control of a first promoter comprising the CMV immediate-early promoter, and said first nucleic acid molecule encodes the M, N, or modified S polypeptide from feline infectious peritonitis virus; and a second nucleic acid molecule under the control of a promoter and the second nucleic acid molecule encodes an antigen for another feline disease.

15. The FHV according to claim 1, wherein the nucleic acid molecule encodes an immunomodulatory polypeptide.

16. The FHV according to claim 15, wherein the nucleic acid molecule encodes a cytokine.

17. A vaccine comprising a vector according to any one of claims 1–16.

18. A vaccine comprising a recombinant feline herpesvirus (FHV) comprising and expressing a nucleic acid molecule encoding the VP2 capsid antigen of feline infectious panleukopenia virus.

19. The vaccine according to claim 18, wherein the nucleic acid molecule is inserted into the ORF5 or the ORF2 site of FHV, which, in the FHV-1 CO strain, have the nucleotide sequences 5869–7113 and 1665–2596, of SEQ ID NO: 1, respectively.

20. A vaccine comprising a recombinant feline herpesvirus (FHV) comprising and expressing a nucleic acid molecule encoding the capsid antigen of feline calicivirus, wherein the nucleic acid molecule is inserted into the ORF5 or the ORF2 site of FHV, which, in the FHV-1 CO strain, have the nucleotide sequences 5869–7113 and 1665–2596, of SEQ ID NO: 1, respectively.

21. A vaccine comprising a recombinant feline herpesvirus (FHV) comprising and expressing a nucleic acid molecule encoding an antigen of feline infectious peritonitis virus, wherein the antigen is chosen from among the group consisting of M, modified S, N, 7b and polymerase and wherein the nucleic acid molecule is inserted into the ORF5 or the ORF2 site of FHV, which, in the FHV-1 CO strain, have the nucleotide sequences 5869–7113 and 1665–2596, of SEQ ID NO: 1, respectively.

22. A vaccine comprising a recombinant feline herpesvirus (FHV) comprising and expressing a nucleic acid molecule encoding an antigen of the feline immunodeficiency virus, wherein the antigen is chosen among the group consisting of env, gag and pol, and wherein the nucleic acid molecule is inserted into the ORF5 or the ORF2 site of FHV, which, in the FHV-1 CO strain, have the nucleotide sequences 5869–7113 and 1665–2596, of SEQ ID NO: 1, respectively.

23. A vaccine comprising a recombinant feline herpesvirus (FHV) comprising and expressing a nucleic acid molecule encoding an antigen of feline leukemia virus, wherein the antigen is chosen among the group consisting of env, gag and pol, and wherein the nucleic acid molecule is inserted into the ORF5 or the ORF2 site of FHV, which, in the FHV-1 CO strain, have the nucleotide sequences 5869–7113 and 1665–2596, of SEQ ID NO:1, respectively.

24. A vaccine comprising a recombinant feline herpesvirus (FHV) comprising and expressing at least one nucleic acid molecule encoding a polypeptide, wherein at least one acid nucleic molecule is inserted into the ORF5 and/or ORF2 site of FHV, which in the FHV-1 CO strain, have the nucleotide sequences 5869–7113 and 1665–2596, of SEQ ID NO: 1, respectively.

25. The vaccine according to claim 24, wherein the at least one nucleic acid molecule is inserted into the ORF5 and/or ORF2 sites by simple insertion, or after total or partial deletion of these sites.

26. The vaccine according to claim 24, wherein the at least one nucleic acid molecule is inserted into one of the ORF5 and ORF2 sites, and a deletion is carried out in the other site.

27. The vaccine according to claim 24, wherein the recombinant FHV includes a strong eukaryotic promoter for expression of the at least one nucleic acid molecule.

28. The vaccine according to claim 27, wherein the strong promoter is a CMV immediate early promoter.

29. The vaccine according to claim 24, wherein the recombinant FHV comprises at least two nucleic acid molecules inserted into the ORF5 or ORF2 site under the control of different eukaryotic promoters.

30. The vaccine according to claim 29, wherein the eukaryotic promoters are CMV immediate-early promoters of different animal origins.

31. The vaccine according to claim 29, wherein the recombinant FHV comprises: a first nucleic acid molecule operably linked to a first promoter wherein the first promoter is the CMV immediate-early promoter; and a second nucleic acid molecule operably linked to a second promoter, and, the 5' end of the promoters are adjacent.

32. The vaccine according to claim 24, wherein the recombinant FHV comprises a nucleic acid molecule encoding an antigenic polypeptide.

33. The vaccine according to claim 32, wherein the nucleic acid molecule encodes an antigenic polypeptide of a feline pathogenic agent.

34. The vaccine according to claim 33, wherein the nucleic acid molecule encodes an antigen selected from the group consisting of: the antigens of the feline infectious peritonitis virus, the antigens of feline leukemia virus, the antigens of feline immunodeficiency virus, the antigens of feline infectious panleukopenia virus and the antigens of feline calicivirus.

35. The vaccine according to claim 33, wherein the nucleic acid molecule encodes a polypeptide from feline infectious peritonitis virus selected from the group consisting of M, modified S and N.

36. The vaccine according to claim 33, wherein the at least one nucleic acid molecule comprises a nucleic acid molecule encoding an antigen selected from the group consisting of the env antigen of feline leukemia virus, the gag antigen of feline leukemia virus, the pol antigen of the feline leukemia virus, the env antigen of feline immunodeficiency virus, the gag antigen of feline immunodeficiency virus, the pol antigen of the feline immunodeficiency virus, the VP2 capsid antigen of the feline infectious panleukopenia virus, the capsid antigen of feline calicivirus, the M antigen of feline infectious peritonitis virus, the modified S antigen of feline infectious peritonitis virus, the N antigen of feline infectious peritonitis virus, the 7b antigen of feline infectious peritonitis virus, and the polymerase antigen of the feline infectious peritonitis virus.

37. The vaccine according to claim 29, wherein the recombinant FHV comprises: a first nucleic acid molecule under the control of a first promoter comprising the CMV immediate-early promoter, and said first nucleic acid molecule encodes the M, N, or modified S polypeptide from feline infectious peritonitis virus; and a second nucleic acid molecule under the control of a promoter and the second nucleic acid molecule encodes an antigen for another feline disease.

38. The vaccine according to claim 24, wherein the nucleic acid molecule encodes an immunomodulatory polypeptide.

39. The vaccine according to claim 38, wherein the nucleic acid molecule encodes a cytokine.

40. An immunogenic composition comprising a recombinant feline herpesvirus (FHV) comprising and expressing a nucleic acid molecule encoding the VP2 capsid antigen of feline infectious panleukopenia virus.

41. An immunogenic composition according to claim 40, wherein the nucleic acid molecule is inserted into the ORF5 or the ORF2 site of FHV, which, in the FHV-1 CO strain, have the nucleotide sequences 5869–7113 and 1665–2596, of SEQ ID NO: 1, respectively.

42. An immunogenic composition comprising a recombinant feline herpesvirus (FHV) comprising and expressing a nucleic acid molecule encoding the capsid antigen of feline calicivirus, wherein the nucleic acid molecule is inserted into the ORF5 or the ORF2 site of FHV, which, in the FHV-1 CO strain, have the nucleotide sequences 5869–7113 and 1665–2596, of SEQ ID NO: 1, respectively.

43. An immunogenic composition comprising a recombinant feline herpesvirus (FHV) comprising and expressing a nucleic acid molecule encoding an antigen of feline infectious peritonitis virus, wherein the antigen is chosen among the group consisting of M, modified S, N, 7b and polymerase and wherein the nucleic acid molecule is inserted into the ORF5 or the ORF2 site of FHV, which, in the FHV-1 CO strain, have the nucleotide sequences 5869–7113 and 1665–2596, of SEQ ID NO: 1, respectively.

44. An immunogenic composition comprising a recombinant feline herpesvirus (FHV) comprising and expressing a nucleic acid molecule encoding an antigen of the feline immunodeficiency virus, wherein the antigen is chosen among the group consisting of env, gag and pol, and wherein the nucleic acid molecule is inserted into the ORF5 or the ORF2 site of FHV, which, in the FHV-1 CO strain, have the nucleotide sequences 5869–7113 and 1665–2596, of SEQ ID NO: 1, respectively.

45. An immunogenic composition comprising a recombinant feline herpesvirus (FHV) comprising and expressing a nucleic acid molecule encoding an antigen of feline leukemia virus, wherein the antigen is chosen among the group consisting of env, gag and pol, and wherein the nucleic acid molecule is inserted into the ORF5 or the ORF2 site of FHV, which, in the FHV-1 CO strain, have the nucleotide sequences 5869–7113 and 1665–2596, of SEQ ID NO:1, respectively.

* * * * *

UNITED STATES PATENT AND TRADEMARK OFFICE
CERTIFICATE OF CORRECTION

PATENT NO.     : 6,387,376 B1
DATED          : May 14, 2002
INVENTOR(S)    : Jean-Christophe Francis Audonnet et al.

It is certified that error appears in the above-identified patent and that said Letters Patent is hereby corrected as shown below:

<u>Title page,</u>
Item [75], Inventors, change "Lyons" to -- Lyon --.
Item [73], Assignee, change "Lyons" to -- Lyon --.

Signed and Sealed this

Twenty-third Day of July, 2002

*Attest:*

JAMES E. ROGAN
*Attesting Officer*     *Director of the United States Patent and Trademark Office*